United States Patent
Hayashi et al.

(10) Patent No.: US 7,026,322 B2
(45) Date of Patent: Apr. 11, 2006

(54) PHENYLAHISTIN AND THE PHENYLAHISTIN ANALOGS, A NEW CLASS OF ANTI-TUMOR COMPOUNDS

(75) Inventors: Yoshio Hayashi, Kawasaki (JP); Michael A. Palladino, Jr., Olivenhain, CA (US); Jennifer Grodberg, Carlsbad, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 10/632,688

(22) Filed: Aug. 1, 2003

(65) Prior Publication Data

US 2004/0102454 A1 May 27, 2004

Related U.S. Application Data

(63) Continuation-in-part of application No. 09/995,851, filed on Nov. 27, 2001, now Pat. No. 6,713,480, which is a continuation of application No. 09/440,316, filed on Nov. 12, 1999, now Pat. No. 6,358,957.
(60) Provisional application No. 60/108,736, filed on Nov. 17, 1998, and provisional application No. 60/108,211, filed on Nov. 12, 1998.

(51) Int. Cl.
  C07D 241/06 (2006.01)
  C07D 241/08 (2006.01)
  A61K 31/496 (2006.01)
  A61K 31/00 (2006.01)

(52) U.S. Cl. .................................. 514/254.05; 544/366
(58) Field of Classification Search ............. 514/254.05
See application file for complete search history.

(56) References Cited

U.S. PATENT DOCUMENTS

| 6,069,146 A | 5/2000 | Fenical et al. |
| 6,358,957 B1 | 3/2002 | Fukumoto et al. |

FOREIGN PATENT DOCUMENTS

| EP | 1 264 831 | 12/2002 |
| GB | 2143823 | 2/1985 |
| JP | 5009164 | 1/1993 |
| JP | 10130266 | 5/1998 |
| WO | WO 2004/054498 | 7/2004 |

OTHER PUBLICATIONS

Ahmed, S.A. et al. "A new rapid and simple non–radioactive assay to monitor and determine the proliferation of lymphocytes: an alternative to [$^3$H]thymidine incorporation assay." *J. Immunol. Methods.* 170, 211–224 (1994).
Algaier, J. et al. "The effects of dimethyl sulfoxide on the kinetics of tubulin assembly." *Biochim. Biophys. Acta.* 954, 235–43 (1988).
Ali M. et al. "Toxicity of echinulin from *Aspergillus chevalieri* in rabbits." *Toxicology Letters.* 48, 235–41 (1989).

Bond, R., et al., "The Synthesis of Viridamine, a *Penicillium Viridicatum* Mycotoxin." *Synthetic Commun.* 19 (13&14), 2551–2566 (1989).
Borisy, G.G. "A Rapid Method for Quantitative Determination of Microtubule Protein using DEAE–Cellulose Filters."*Anal. Biochem.* 50, 373–385 (1972).
Cui, C. et al. "Novel Mammalian Cell Cycle Inhibitors, Tryprostatins A, B and Other Diketopiperazines Produced by *Aspergillus fumigatus.*" *J. Antibiotics.* 49, 534–40 (1996).
Cui, C. et al. "Novel Mammalian Cell Cycle Inhibitors, Tryprostatins A, B and Other Diketopiperazines Produced *Aspergillus fumigatus.*" *J. Antibiotics.* 49, 527–33 (1996).
Goldani, L.Z. & Sugar, A.M. "Treatment of murine pulmonary mucormycosis with SCH 42427, a broad–spectrum triazole antifungal drug." *J. Antimicrob Chemother.* 33, 369–372 (1994).

(Continued)

*Primary Examiner*—Venkataraman Balasurbramanian
(74) *Attorney, Agent, or Firm*—Knobbe, Martens, Olson & Bear, LLP

(57) ABSTRACT

Methods of using a compound, its pharmaceutically acceptable salts, and/or its pro-drug esters, in isolated form, to treat cancer, and methods for isolating, for formulating, and for administering the compound, salt, and/or pro-drug ester as an antitumor agent, wherein the compound, salt, or pro-drug ester has the following structure:

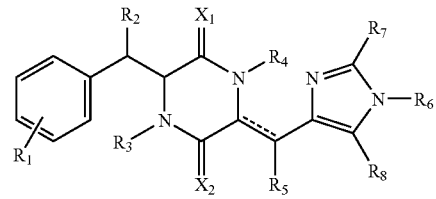

wherein:
  $R_1$, $R_2$, $R_5$, $R_7$, and $R_8$ are each separately selected from the group consisting of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups,
  $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups,
  $X_1$ and $X_2$ are separately selected from the group consisting of an oxygen atom, and a sulfur atom, and
  the dashed bond represents a bond selected from the group consisting of a carbon-carbon single bond and a carbon-carbon double bond. Most preferably, $R_3$ and $R_4$ are hydrogen, and each are involved in hydrogen bonds, and/or the dashed bond is a double bond, such that the chemical backbone of the compound substantially retains a substantially planar conformation.

10 Claims, 12 Drawing Sheets

OTHER PUBLICATIONS

Gordon, D., et al. "Reductive Alkylation on a Solid Phase: Synthesis of a Piperazinedione Combinatorial Library." *J. Bioorg. Med. Chem. Letters.* 5, 47–50 (1995).

Hamel, E. "Antimitotic Natural Products and Their Interactions with Tubulin." *Med. Res. Rev.* 16(2), 207–31 (1996).

Hartwell, L.H. et al. "Checkpoints: Controls that Ensure the Order of Cell Cycle Events." *Science.* 246, 629–34 (1989).

Horak R.M. et al. "Structure of the Austalides A–E, Five Novel Toxic Metabolites from *Aspergillus ustus.*" *J.C.S. Chem. Comm.* 1265–67 (1981).

Iwasaki, S. "Bioactive Natural Products Interfering with Microtubule Function." *Kagaku to Seibutsu.* 32(3), 153–159 (1994).

Iwasaki, S. "Antimitotic Agents: Chemistry and Recognition of Tubulin Molecule." *Med Res Rev.* 13, 183–198 (1993).

Johnson, K.A. et al. "Kinetic Analysis of Microtubule Self-assembly in Vitro." *J. Mol. Biol.* 117, 1–31 (1977).

Keepers Y.P., et al., "Comparison of the Sulforhodamine B Protein and Tetrazolium (MIT) Assays for in vitro Chemosensitivity Testing." *Eur. J. Cancer.* 27, 897–900 (1991).

Kondoh, M. et al. "Effects of Tryprostatin Derivatives on Microtubule Assembly In Vitro and In Situ." *J. Antibiotics.* 51, 801–04 (1998).

Krishan, A. "Rapid Flow Cytofluorometric Analysis of Mammalian Cell Cycle By Propidium Iodide Staining." *J. Cell Biol.* 66, 188–193 (1975).

Kupchan, S.M. et al. "Steganacin and Steganangin, Novel Antileukemic Lignan Lactones from *Steganotaenia araliacea* 1–3." *J. Am. Chem. Soc.* 95(4), 1335–36 (1973).

Lacey, E. et al. "Interaction of Phomopsin A and Related Compounds with Purified Sheep Brain Tubulin." *Biochem. Pharmacol.* 36, 2133–38 (1987).

Laemmli, U.K. "Cleavage of Structural Proteins during the Assembly of the Head of Bacteriophage T4." *Nature.* 227, 680–85 (1970).

Larsen, T.O et al. "Aurantiamine, A Kiketopiperazine from Two Varieties of Penicillium Aurantiogriseum." *Phytochemistry.* 31, 1613–1615 (1992).

Lee, J.C. et al. "The Reconstitution of Microtubules from Purified Calf Brain Tubulin." *Biochemistr.* 14(23), 5183–87 (1975).

Li, Y., et al. "Interaction of marine toxin dolastatin 10 with porcine brain tubulin: competitive inhibition of rhizoxin and phomopsin A binding." *Chem. Biol. Interact.* 93, 175–83 (1994).

Liwo, A. et al. "Origin of the Ring–Ring Interaction in Cyclic Dipeptides Incorporating an Aromatic Amino Acid." *Tetrahedron Lett.* 26, 1873–1876 (1985).

Luduena, R.F. "Contrasting Roles of Tau and Microtubule–associated Protein 2 in the Vinblastine–induced Aggregation of Brain Tubulin." *J. Biol. Chem.* 259:12890–98 (1984).

Pettit, G.R. et al. "Antineoplastic Agents. 291. Isolation and Synthesis of Combretastatins A–4, A–5, and A–6 1a." *J. Med. Chem.* 38, 1666–1672 (1995).

Roberge, M. et al. "Antitumor Drug Fostriecin Inhibits the Mitotic Entry Checkpoint and Protein Phosphates 1 and 2A." *Cancer Res.* 54, 6115–21 (1994).

Rowinsky, E. K. et al. "Taxol: A Novel Investigational Antimicrotubule Agent." *J. Natl. Cancer Inst.* 82, 1247–59 (1990).

Sackett, D.L. "Podophyllotoxin, Steganacin and Combretastatin: Natural Products that Bind at the Colchicine Site of Tubulin." *Pharmacol. Ther.* 59, 163–228 (1993).

Sherline, P., et al. "Binding of Colchicine to Purified Microtubule Protein." *J. Biol. Chem.* 250, 5481–86 (1975).

Smedsgaard J. et al. "Using direct electrospray mass spectrometry in taxonomy and secondary metabolite profiling of crude fungal extracts." *J. Microbiol. Meth.* 25, 5–17 (1996).

Steyn, P.S. "The Structures of Five Diketopiperazines from *Aspergillus Ustus.*"*Tetrahedron.* 29, 107–120 (1973).

Sugar, A., et al. "Comparison of Three Methods of Antifungal Susceptibility Testing with the Proposed NCCLS Standard Broth Macrodilution Assay: Lack of Effect of Phenol Red." *Diagn Micro and Infect Diseases.* 21, 129–133 (1995).

Takahashi, M., et al. "Rhizoxin binding to tubulin at the maytansine–binding site." *Biochim. Biophys. Acta.* 926, 215–23 (1987).

Tiwari, S.C. et al. "A pH– and Temperature–Dependent Cyclic Method that doubles the Yield of Microtubule Protein." *Anal. Biochem.* 215, 96–103 (1993).

Turner and Rodriguez. "Recent Advances in the Medicinal Chemistry of Antifungal Agents." *Current Pharmaceutical Design.* 2, 209–224 (1996).

Usui, T. et al. "Tryprostatin A, a specific and novel inhibitor of microtubule assembly." *Biochem J.* 333, 543–48 (1998).

Van der Waerden, B.L. *Arch Exp Pathol Pharmakol.* 195, 389–412 (1940).

Verdier–Pinard, P., et al., "Structure–Activity Analysis of the Interaction of Curacin A, the Potent Colchicine Site Antimitotic Agent, with Tubulin and Effects of Analogs on the Growth of MCF–7 breast Cancer Cells." *Mol. Pharmacol.* 53, 62–76 (1998).

Weisenberg, R.C. et al. "The Colchicine–Binding Protein of Mammalian Brain and its Relation to Microtubules." *Biochemistry* 7(12), 4466–79 (1968).

Yahara, I. et al. "Microtubule Organization of Lymphocytes and its Modulation by Patch and Cap Formation." *Cell.* 15, 251–259 (1978).

Yamazaki, M. et al. "Crystal Structure and Absolute Configuration of Fumitremorgin B, a Tremorgenic Toxin from *Aspergillus fumigatus* Fres." *Tetrahedron Lett.* 1, 27–28 (1975).

Yamori T. *Jap. J. Cancer Chemother.* 24, 129–35 (1997).

Yoshida, Minoru M. *Protein Nucleic Acid Enzymes.* 38, 1753–1765 (1993).

Yoshimatsu, K., et al. "Mechanism of Action of E7010, an Orally Active Sulfonamide Antitumor Agent: Inhibition of Mitosis by Binding to the Colchicine Site of Tubulin." *Cancer Res.* 57, 3208–13 (1997).

Dandan, et al., JP 5009164–CA 119: 8514 (1993).

Kim, et al., "*Polymer attached cyclic peptides, Tetrahedron: Asymmetry,*" 3(11) 1421–30 (1992).

Kanoh, et al., "*Phenylahistin: A new mammalian cell cycle inhibitor produced by asperigillus ustus*" *Bio. & Med. Chem. Lett.*, vol. 7, pp. 2847–2852 (1997).

Kanoh, et al., "*Synthesis and Biological Activities of Phenylahistin Derivatives*", *Bio. & Med. Chem.*, 1–7 (1999).

Kanoh, et al., "*Antitumor Activity of Phenylahistin in Vitro and in Vivo*", *Biochem. Biosc. Biotec.*, 63 (6), 1130–1133 (1999).

Kanoh, et al., "*(–)–Phenylahistin Arrests Cells in Mitosis by Inhibiting Tubulin Polymerization*", *The Journal of Antibiotics*, V. 52, No. 2, (Feb. 1999).

International Search Report for International Application No. PCT/US2004/024940 mailed Oct. 25, 2004.

Day 27-> n=2 NPI-2386 Groups

PHENYLAHISTIN AND THE PHENYLAHISTIN ANALOGS, A NEW CLASS OF ANTI-TUMOR COMPOUNDS

RELATED APPLICATIONS

This application is a continuation-in-part of U.S. application Ser. No. 09/995,851, filed Nov. 27, 2001 U.S. Pat. No. 6,713,480, which is a continuation of, and claims priority from, U.S. application Ser. No. 09/440,316, filed Nov. 12, 1999, U.S. Pat. No. 6,358,957, which application claimed priority from U.S. Provisional Application Ser. No. 60/108,211, PHENYLAHISTIN AS AN ANTI-TUMOR COMPOUND, filed Nov. 12, 1998, by Fukumoto et al., and also claimed priority from U.S. Provisional Application Ser. No. 60/108,736, PHENYLAHISTIN AS AN ANTI-TUMOR COMPOUND, filed Nov. 17, 1998, by Fukumoto et al.. Each of the above-mentioned applications is incorporated herein by reference in its entirety.

This application is also related to U.S. application Ser. No. 10/632,531, entitled DEHYDROPHENYLAHISTINS AND ANALOGS THEREOF AND THE SYNTHESIS OF DEHYDROPHENYLAHISTINS AND ANALOGS THEREOF, filed on Aug. 1, 2003, and which is incorporated herein by reference in its entirety.

BACKGROUND OF THE INVENTION

1. Field of the Invention

The present invention relates to the fields of chemistry and medicine. More specifically, the present invention relates to compounds and procedures useful in the treatment of cancer, or in the treatment of fungal infections.

2. Description of the Related Art

It is thought that a single, universal cellular mechanism controls the regulation of the eukaryotic cell cycle process. See, e.g., Hartwell, L. H. et al., Science (1989), 246: 629–34. It is also known that when an abnormality arises in the control mechanism of the cell cycle, cancer or an immune disorder may occur. Accordingly, as is also known, antitumor agents and immune suppressors may be among the substances that regular the cell cycle. Thus, new eukaryotic cell cycle inhibitors are needed as antitumor and immune-enhancing compounds, and should be useful in the treatment of human cancer as chemotherapeutic, anti-tumor agents. See, e.g., Roberge, M. et al., Cancer Res. (1994), 54, 6115–21.

Recently, it has been reported that tryprostatins A and B (which are diketopiperazines consisting of proline and iso-prenylated tryptophan residues), and five other structurally-related diketopiperazines, inhibited cell cycle progression in the M phase, see Cui, C. et al., J. Antibiotics (1996), 49, 527–33; Cui, C. et al. J. Antibiotics (1996), 49, 534–40, and that these compounds also affect the microtubule assembly, see Usui, T. et al. Biochem J. (1998) 333, 543–48; Kondon, M. et al. J. Antibiotics (1998) 51, 801–04. Furthermore, natural and synthetic compounds have been reported to inhibit mitosis, thus inhibit the eukaryotic cell cycle, by binding to the colchicine binding-site (CLC-site) on tubulin, which is a macromolecule that consists of two 50 kDa subunits (α- and β-tubulin) and is the major constituent of microtubules. See, e.g., Iwasaki, S., Med. Res. Rev. (1993) 13, 183–198; Hamel, E. Med. Res. Rev. (1996) 16, 207–31; Weisenberg, R. C. et al., Biochemistry (1969) 7, 4466–79. Microtubules are thought to be involved in several essential cell functions, such as axonal transport, cell motility and determination of cell morphology. Therefore, inhibitors of microtubule function may have broad biological activity, and be applicable to medicinal and agrochemical purposes. It is also possible that colchicine (CLC)-site ligands such as CLC, steganacin, see Kupchan, S. M. et al., J. Am. Chem. Soc. (1973) 95, 1335–36, podophyllotoxin, see Sackett, D. L., Pharmacol. Ther. (1993) 59, 163–228, and combretastatins, see Pettit, G. R. et al., J. Med. Chem. (1995) 38, 166–67, may prove to be valuable as eukaryotic cell cycle inhibitors and, thus, may be useful as chemotherapeutic agents.

Although diketopiperazine-type metabolites have been isolated from various fungi as mycotoxins, see Horak R. M. et al., J.C.S. Chem. Comm. (1981) 1265–67; Ali M. et al., Toxicology Letters, (1989) 48, 235–41, or as secondary metabolites, see Smedsgaard J. et al., J. Microbiol. Meth. (1996) 25, 5–17, little is known about the specific structure of the diketopiperazine-type metabolites and their antitumor activity, particularly in vivo. Furthermore, even though known antitumor substances isolated from microorganism metabolites (including anthracyclins and mitomycins that exhibit antitumor activity by binding to DNA) have been used as antitumor agents, see *Microorganic Pharmaceutical Chemistry*, revised 2nd edition, edited by Yoshio Ueno & Satoshi Ohmura, Nankohdo Publishing Co., (1986)), and even though anti-tumor substances having non-DNA binding operating mechanism have been isolated from microorganism metabolites, see Minoru Yoshida, M. *Protein Nucleic Acid Enzymes* (1993) 38, 1753; and Iwasaki, N., Chemistry and Living Organisms, (1994) 32, No. 3, 153, there is a particular need for new microorganism metabolite-derived compounds having animal cell-specific proliferation-inhibiting activity and high antitumor activity and selectivity. There is therefore a related need for substantially purified, and structurally and biologically characterized fungal diketopiperazine-type metabolites and fungal diketopiperazine-type metabolite-derivatives.

SUMMARY OF THE INVENTION

A compound, and any pharmaceutically acceptable salt or pro-drug ester thereof, suitable for use as an anti-tumor agent having the following generic structure:

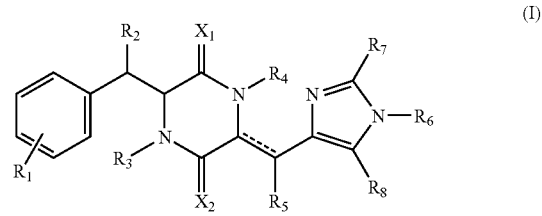

(I)

wherein:

$R_1$, $R_2$, $R_5$, $R_7$, and $R_8$ are each separately selected from the group consisting of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups, and $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups, $X_1$ and $X_2$ are separately selected from the group consisting of an oxygen atom, and a sulfur atom, and the dashed bond represents a bond selected from the group consisting of a carbon-carbon single bond and a carbon-carbon double bond.

In a preferred embodiment, the invention comprises, in substantially purified form, the compound herein named alternatively "(−)-phenylahistin," "(−)-NSCL-96F037," or "(−)-PLH," which is a diketopiperazine composed of L-phenylalanine and isoprenylated dehydrohistidine. This compound has the following stereo-specific chemical structure:

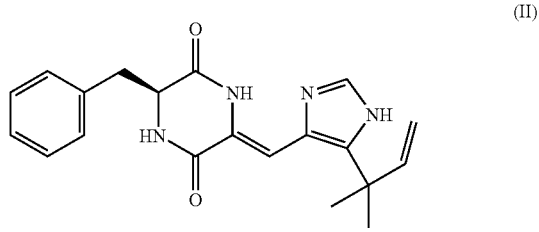

(II)

The invention also comprises a method of treating cancer comprising administering an effective tumor-growth-inhibiting amount of the compound, and any pharmaceutically acceptable salt or pro-drug ester of generic structure (I), and preferably, phenylahistin, and more preferably, (−)-phenylahistin, and pharmaceutically acceptable salt and pro-drug esters thereof. In preferred embodiments of the compound, salt, or pro-drug ester of the present invention, $R_3$ and $R_4$ are hydrogen, and each are involved in hydrogen bonds, and/or the dashed bond is a double bond.

Other embodiments relate to methods of treating and/or preventing at least one fungal infection in a mammal afflicted with at least one fungal infection. The methods can include, for example, administering an antifungally effective amount of a compound sufficient for such treating or preventing. The compound can have, for example, the following structure:

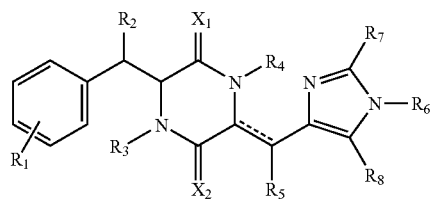

wherein:

$R_1$, $R_2$, $R_5$, $R_7$, and $R_8$ are each separately selected from the group consisting of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups, $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups, $X_1$ and $X_2$ are separately selected from the group consisting of an oxygen atom, and a sulfur atom, and the dashed bond represents a bond selected from the group consisting of a carbon-carbon single bond and a carbon-carbon double bond.

The fungal infection can be for example, an Aspergillosis infection, a blastomycosis infection, a Candidiasis infection, a Coccidioidomycosis infection, a Cryptococcosis infection, a Histopolasmosis infection, a Paracoccidioidomycosis, a Sporotrichosisand, a Mucormycosis infection, and the like. Preferably, the Aspergillosis infection can be invasive pulmonary aspergillosis. Further, preferably, the Mucormycosis infection can be craniofacial mucormycosis, pulmonary mucormycosis and the like. Also, preferably, the Candidiasis infection can be retrograde candidiasis of the urinary tract, for example.

Still further embodiments relate to pharmaceutical compositions for treating or preventing fungal infection. The compositions can include, for example, an antifungally effective amount of a pharmaceutically acceptable carrier and a compound having the structure:

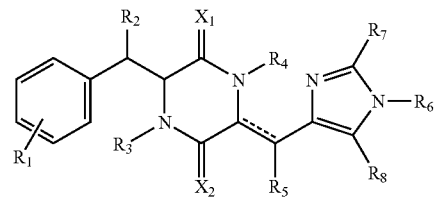

wherein:

$R_1$, $R_2$, $R_5$, $R_7$, and $R_8$ are each separately selected from the group consisting of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups, $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups, $X_1$ and $X_2$ are separately selected from the group consisting of an oxygen atom, and a sulfur atom, and the dashed bond represents a bond selected from the group consisting of a carbon-carbon single bond and a carbon-carbon double bond.

Preferably, the fungal infection can be an Aspergillosis infection, a blastomycosis infection, a Candidiasis infection, a Coccidioidomycosis infection, a Cryptococcosis infection, a Histopolasmosis infection, a Paracoccidioidomycosis, a Sporotrichosis and, a Mucormycosis infection, and the like. Preferably, the Aspergillosis infection can be invasive pulmonary aspergillosis. Further, preferably, the Mucormycosis infection can be craniofacial mucormycosis, pulmonary mucormycosis and the like. Also, preferably, the Candidiasis infection can be retrograde candidiasis of the urinary tract, for example.

Embodiments also relate to methods and materials for treating or preventing cancers and infection by a pathogenic fungus in a mammalian subject, particularly a human patient, by administering to the subject a phenylahistin or its analog. The methods can include administering to the subject a composition comprising an effective antitumor or antifungal amount of a phenylahistin or its analog.

BRIEF DESCRIPTION OF THE DRAWINGS

The accompanying drawings, which are incorporated in and form part of the specification, merely illustrate embodiments of the present invention. Together with the remainder of the specification, they are meant to serve to explain preferred modes of making certain compounds of the invention to those of skilled in the art. In the drawings:

In FIG. 3, (a) refers to $H_2$/10% Pd—C, MeOH, room temperature, reaction time of 2 hours, and (b) refers to $H_2$/10% Pd—C, MeOH, room temperature, reaction time of 24 hours.

In FIG. 4, (a) refers to MeI, NaH, DMF, −30° C., reaction time of 2 hours, (b) refers to MeI, NaH, DMF, room temperature, reaction time of 2 hours; and (c) refers to chiral HPLC separation as described herein.

In FIG. 5, (a) refers to MeOH at reflux for 14 hours, (b) refers to $AcO_2$, AcONa, 80° C., reaction time of 14 hours, and (c–e) refers to reaction in a mixture of compound 18, LDA, HMPA, DMF, at −60° C. for 30 minutes, followed by cooling to room temperature and placing in a solution of $Tf_2O$, pyridine for 10 minutes, followed by overnight reaction in $NH_4OH$ at room temperature.

DETAILED DESCRIPTION OF THE PREFERRED EMBODIMENT

Figure 1:
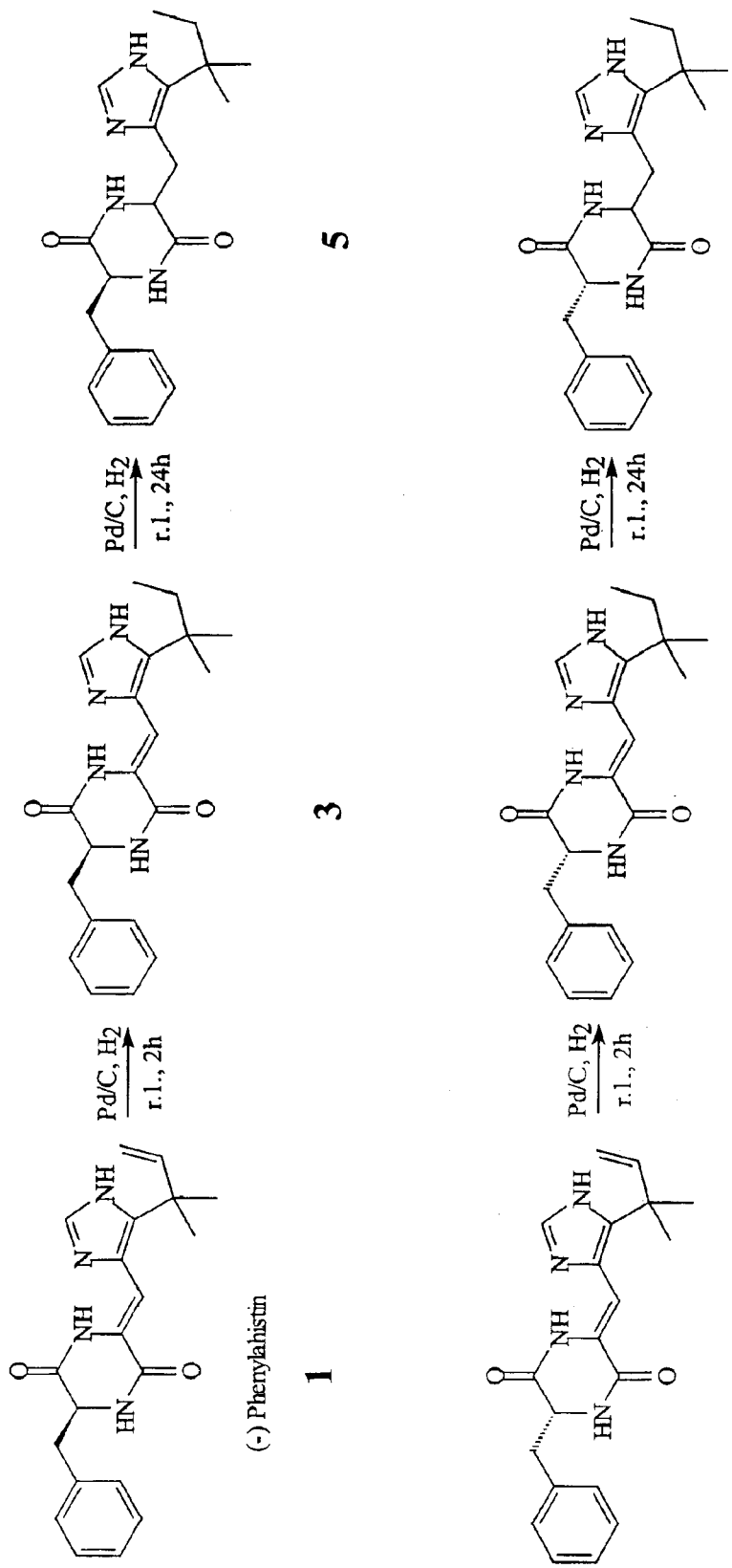
FIG. 1 illustrates Reaction Scheme 1, which shows the preparation of certain reduced derivatives of (−)- and (+)-phenylahistin from the enantiomers of phenylahistin.

Numerous references are cited herein. These references are to be considered incorporated by reference into this specification.

Objects of this invention include (1) providing a class of new compounds, including pharmaceutically acceptable salts of the class of compounds, that exhibit animal cell-specific proliferation inhibiting, tumor-growth inhibiting activity, anti-fungal activity, and/or cell-cycle inhibiting activity, and (2) providing a class of fungi for producing, and (3) providing a method for producing said class of compounds, as well as a class of pharmaceutically acceptable cell cycle inhibitors, antitumor agents, and anti-fungal agents comprising said compounds and/or their derivatives as active ingredients. It is also an object of this invention to provide a method of treating cancer, particularly human cancer, comprising the step of administering an effective tumor-growth inhibiting amount of a member of a class of new anti-tumor compounds. Further, it is an object of this invention to provide a method of treating fungal infections or pathogenic fungus, including those affecting animals and humans, comprising the step of administering an effective tumor-growth inhibiting amount of a member of a class of new anti-tumor compounds. In the preferred embodiment of the present invention, but not necessarily in all embodiments of the present invention, these objectives are simultaneously met.

The invention provides the compound represented by Formula (I):

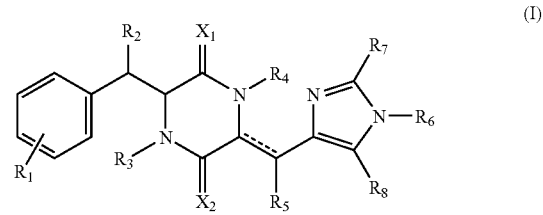

wherein:

$R_1$, $R_2$, $R_5$, $R_7$, and $R_8$ are each separately selected from the group consisting of a hydrogen atom, a halogen atom, saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups, all having, where applicable, up to 24 carbon atoms, $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups, all having, where applicable, up to 12 carbon atoms, $X_1$ and $X_2$ are separately selected from the group consisting of an oxygen atom, and a sulfur atom, and the dashed bond represents either a carbon-carbon single bond or a carbon-carbon double bond, of any tertiary conformation, in a particular embodiment of the invention.

The invention also provides pharmaceutically acceptable salts and pro-drug esters of the compound of Formula (I).

The term "pro-drug ester," especially when referring to a pro-drug ester of the compound of Formula (I), refers to a chemical derivative of the compound that is rapidly transformed in vivo to yield the compound, for example, by hydrolysis in blood. The term "pro-drug ester" refers to derivatives of the compound of the present invention formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as prodrugs for compounds containing carboxyl groups).

The term "pharmaceutically acceptable salt," especially when referring to a pharmaceutically acceptable salt of the compound of Formula (I), refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$–$C_7$ alkylamine, cyclohexylamine, triethanolamine, ethylenediamine or tris-(hydroxymethyl)-aminomethane. With respect to compounds of the invention that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions of the present invention include pharmaceutically acceptable salts and pro-drug esters of the compound of Formula (I). Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

In preferred embodiments of the compounds of the present invention, a relatively rigid, planar pseudo three-ring structure is formed. To stable such a relatively rigid, planar pseudo three-ring structure, $R_3$ and $R_4$ are hydrogen, each involved in hydrogen bonds. Furthermore, such a relatively rigid, planar pseudo three-ring structure is stabilized wherein the dashed bond is a double bond.

The term "halogen atom" means any one of the radio-stable atoms of column 17 of the Periodic Table of the Elements, i.e., fluorine, chlorine, bromine, or iodine, with fluorine and chlorine being preferred.

The term "alkyl" means any unbranched or branched, substituted or unsubstituted, saturated hydrocarbon, with $C_1$–$C_6$ unbranched, saturated, unsubstituted hydrocarbons being preferred, with methyl, ethyl, iosbutyl, and tert-butyl being most preferred. Among the substituted, saturated hydrocarbons, $C_1$–$C_6$ mono- and di- and per-halogen substituted saturated hydrocarbons and amino-substituted hydrocarbons are preferred, with perfluromethyl, perchloromethyl, perfluoro-tert-butyl, and perchloro-tert-butyl being the most preferred. The term "cycloalkyl" refers to any non-aromatic hydrocarbon ring, preferably having five to twelve atoms comprising the ring.

The term "alkenyl" means any unbranched or branched, substituted or unsubstituted, unsaturated hydrocarbon including polyunsaturated hydrocarbons, with $C_1$–$C_6$ unbranched, mono-unsaturated and di-unsaturated, unsubstituted hydrocarbons being preferred, and mono-unsaturated, di-halogen substituted hydrocarbons being most preferred. In the $R_1$ and $R_8$ positions, of the compound of structure (I) a z-isoprenyl moiety is particularly preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl" refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom.

The term "alkoxy" refers to any unbranched, or branched, substituted or unsubstituted, saturated or unsaturated ether, with $C_1$–$C_6$ unbranched, saturated, unsubstituted ethers being preferred, with dimethyl, diethyl, methyl-isobutyl, and methyl-tert-butyl ethers being most preferred. The term "cycloalkoxy" refers to any non-aromatic hydrocarbon ring, preferably having five to twelve atoms comprising the ring.

The terms "purified," "substantially purified," and "isolated" as used herein refer to the compound of the invention being free of other, dissimilar compounds with which the compound of the invention is normally associated in its natural state, so that the compound of the invention comprises at least 0.5%, 1%, 5%, 10%, or 20%, and most preferably at least 50% or 75% of the mass, by weight, of a given sample. In one preferred embodiment, these terms refer to the compound of the invention comprising at least 95% of the mass, by weight, of a given sample.

The terms "anti-tumor" and "tumor-growth-inhibiting," when modifying the term "compound," and the terms "inhibiting" and "reducing", when modifying the terms "compound" and/or the term "tumor," mean that the presence of the subject compound is correlated with at least the slowing of the rate of growth of the tumor. More preferably, the terms "anti-tumor," "tumor-growth-inhibiting," "inhibiting," and "reducing" refer to a correlation between the presence of the subject compound and at least the temporary cessation of tumor growth. The terms "anti-tumor," "tumor-growth-inhibiting," "inhibiting," and "reducing" also refer to, particularly in the most preferred embodiment of the invention, a correlation between the presence of the subject compound and at least the temporary reduction in the mass of the tumor.

The invention also provides fungi of the genus *Aspergillus* that are capable of producing the anti-tumor compound of the invention, and specifically, fungi that are capable of producing the anti-tumor compound of the invention wherein $R_1$, $R_2$, $R_3$, $R_4$, $R_5$, $R_6$, $R_7$, and $R_8$ are each a hydrogen atom, and $X_1$ and $X_2$ are each separately an oxygen atom. Preferably, the fungi is an *Aspergillus ustus* capable of producing the antitumor compound of the invention in an amount of not less than 2 mg, preferably not less than 8 mg, per liter of the production medium as measured, by high performance liquid chromatography using the compound represented by Formula (I) as a standard with respect to what is obtained by placing, in 18 mm-diameter, 180 mm-length test tubes, 5 ml of production medium (production medium: glucose 5 g/l, glycerin 20 ml/l, cotton seed lees 20 g/l, yeast extract 2 g/l, sodium chloride 2.5 g/l, calcium carbonate 4 g/l (pH6.5)), and then inoculating each test tube with 50 µl of a fungus suspension prepared by suspending conidia of the fungal strain in sterilized water, incubating the culture broth for 5 days at 27° C. under reciprocal shaking (260 rpm), adding 10 ml of acetone to the culture broth in each test tube, effecting extraction for 1 day at room temperature, removing impurities by filtration, vacuum-concentrating the filtrate to distill off the acetone, making three additions of 5 ml of ethyl acetate to the remaining water layer to effect extraction, effecting vacuum-concentration and drying to obtain a solid, and dissolving the solid in methanol. The invention also provides a method of producing the anti-tumor compound of Formula (I) comprising the steps of incubating in a culture medium a microorganism belonging to the genus *Aspergillus* that is capable of producing the antitumor compound represented of Formula (I) and collecting the compound from the culture. The invention further provides a cell cycle inhibitor and an antitumor agent containing the antitumor substance of Formula (I) as an active ingredient, in combination with a pharmaceutically acceptable carrier or excipient.

Most specifically, a preferred embodiment of the invention provides, phenylahistin, which exhibits the following physical and chemical characteristics:

(i) molecular weight: 350 (FABMS M/Z 351 (M+H)), (ii) molecular formula: $C_{20}H_{22}N_4O_2$, (iii) infrared absorption spectrum (IR $V_{max}$ (KBr)(cm$^{-1}$)): 3440, 3240, 1670, 1640, 1140;

(iv) $^1$H-nuclear magnetic resonance spectrum (500 MHz, measured in CDCl$_3$, chemical shift value of CHCl$_3$ set to 7.24 ppm as internal standard) having intensities at (δ (ppm)): 1.47(6H, s), 2.94 (1H, dd, J=14, 10 Hz), 3.45(1H, dd, J=14, 4 Hz), 4.33(1H, brd, J=10 Hz), 5.10(1H, d, J=17 Hz), 5.14(1H, d, J=11 Hz), 5.88(1H, br), 6.00(1H, dd, J=17, 11 Hz), 6.86(1H, s), 7.21–7.26 (3H, m), 7.31(2H, t, J=8 Hz), 7.53(1H, s), 9.61(1H, br), 12.08(1H,br);

(v) $^{13}$C-nuclear magnetic resonance spectrum (400 MHz, measured in CDCl$_3$, chemical shift value of CDCl$_3$ set to 77.10 ppm as internal standard) having intensities at (δ (ppm)): 28.07(CH$_3$), 28.07(CH$_3$), 37.69(C), 41.33 (CH$_2$), 57.24(CH), 105.67(CH), 113.46(CH$_2$), 123.77 (CH), 127.56(CH), 129.18(CH), 129.18(CH), 129.62 (CH), 129.62(CH), 132.29(C), 132.64(C), 135.55(C), 136.88(C), 144.75(CH), 160.04(C), 164.85(C);

(vi) $^{15}$N-nuclear magnetic resonance spectrum (600 MHz, measured in CDCl$_3$, chemical shift value of ammonia set to 0 ppm as internal standard) having intensities at (δ (ppm)): 112, 134, 161, 253;

(vii) maximum absorption value of ultraviolet spectrum in methanol at 230 nm, and under neutral condition at 323 nm;

(viii) excited under a neutral condition in methanol by 320–340 nm ultraviolet light, having a maximum value at 395–400 nm and emitting fluorescence having 350–550 nm wavelength width;

(ix) soluble in ethyl acetate, chloroform, methanol, and pyridine, but only slightly soluble in water, benzene, and toluene;

(x) negative in ninhydrin reaction, positive in color reaction with nitrous acid (orange); and (xi) substance color: white.

According to the examples provided herein, phenylahistin has been isolated from *Aspergillus ustus* NSC-F038 and NSC-F037, two new strains of fungus; this phenylahistin exhibits cytotoxic and cell cycle inhibitory activities. Both of these strains of fungi have been deposited with the National Institute of Bioscience and Human-Technology, Japan, Agency of Industrial Science and Technology, Ministry of International Trade and Industry. These strains exhibit the following mycological characteristics:

(1) Growth morphology in various culture media: Growth on Czapek's yeast extract agar medium (25° C.) is rapid, reaching 45–46 mm in 7 days. Growth on Czapek's yeast extract agar medium (37° C.) is somewhat slower, reaching 39–41 mm in 7 days. On malt extract agar medium, colony surface is gray and colony rear surface grayish-green.

(2) Morphological properties.

Morphological properties on Czapek's agar medium are indicated.

Condial heads: Radiate

Conidiophore: Smooth surface, brown with length of 100–350:m, 4–7:m diameter

Vesicles: Spherical-flask-shaped, 11–15:m diameter, upper ⅔–½ forms metulae

Metulae: covering upper half to two-thirds of the vesicles, 5–7×4–7 μm

Phialides: amplliform, 5–8×3–4:m

Conidium: Brown, sperical, rough wall, 3×5:m

From these mycological properties, *Aspergillus ustus* NSC-F037 and *Aspergillus ustus* NSC-F038 were found, in accordance with the text *Aspergillus*, K. B. Raper and D. I. Fennel, Williams and Wilkins (1965), to belong to subphylum Fungi Imperfecti, order monilliales, genus *Aspergillus*, species *ustus*. The strains were therefore termed *Aspergillus ustus* NSC-F037 and *Aspergillus ustus* NSC-F038. It was concluded that *Aspergillus ustus* NSC-037 and *Aspergillus ustus* NSC-038 were both novel fungal strains, and they were respectively assigned the acquisition numbers FERM P-15829 and FERM P-15930.

The compound of Formula (I), the compound of the invention, can be produced by ordinary methods, from a culture medium and via extracting the compound from a culture of either *Aspergillus ustus* NSC-037 or *Aspergillus ustus* NSC-038 in the following manner. Although the culture can be either liquid or solid, industrially advantageous culture can be achieved by inoculating a liquid medium with a fungus suspension of the microorganism and incubating the medium under aeration-mixing. Although the culture medium nutrients are not particularly limited, carbon sources, nitrogen sources and other culture medium ingredients ordinarily used to culture microorganisms may be included and are preferred. Usable carbon sources include starch, glycerin, glucose, sucrose, galactose, and the like. Usable nitrogen sources included peptone, soy bean powder, meat extract, corn-steeped liquor, cotton seed lees, ammonium salt, nitrates, and other organic and inorganic nitrogen compounds. In addition, inorganic salts and trace nutrients may be added as will be deemed appropriate by those of skill in the art. The culture temperature, culture time period, and other culture conditions are preferably chosen as conditions that are appropriate for growth of the selected fungus, and also to maximize production of the compound represented by Formula (1). For instance, the pH of the culture medium is preferably between approximately 4 and approximately 9, and more preferably between 5 and 8, and the culture temperature is preferably between 15 and 35° C., and more preferably between 23 and 28° C. The culture period is preferably between 48 and 192 hours, and more preferably between 72 and 192 hours. However, the culture medium composition, culture medium pH, culture medium temperature, culture period and other culture conditions should naturally be appropriately adjusted according to the type of fungus used, the external conditions, and the like so as to obtain the desired results of producing the compound of the present invention. The compound represented by Formula (1) can be collected from such a culture by appropriate use of means ordinarily used for collecting metabolites. For example, any means utilizing the difference in affinity for and organic solvent between the compound represented by Formula (1) and other substances contained in the culture, means utilizing difference in solubility and means utilizing difference in adsorptive affinity for various resins can be used independently, in appropriate combination, or repeatedly. Specifically, ion-exchange chromatography, chromatography using a nonionic adsorptive resin, gel-filter chromatography, chromatography using an adsorbent such as activated carbon, alumina or silica gel, high-speed liquid chromatography, various other types of liquid chromatography, crystallization, vacuum concentration, freeze-drying and other such means can be used independently, in appropriate combination, or repeatedly.

When used as a cell cycle inhibitor, anti-fungal, or tumor-growth-inhibiting compound, the compound of Formula (I) can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it may be administered topically, rectally, or vaginally, as deemed appropriate by those of skill in the art for bringing the compound of the invention into optimal contact with a tumor, thus inhibiting the growth of the tumor. Local administration at the site of the tumor is also contemplated, either before or after tumor resection, as are controlled release formulations, depot formulations, and infusion pump delivery.

To formulate the compound of Formula (I) as a cell cycle inhibitor or tumor-growth-inhibiting compound, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methyiacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound of the invention, particularly when the compound is to be administered orally.

The cell cycle inhibitor and antitumor agent of the invention may be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound of the invention may preferably be administered in the stated amounts continuously by, for example, an intravenous drip. Thus, for the example of a patient weighing 70 kilograms, the preferred daily dose of the active anti-tumor ingredient would be about 0.07 mg/day to about 700 grams/day, and more preferable, 7 mg/day to about 7 grams/day. Nonetheless, as will be understood by those of skill in the art, in certain situations it may be necessary to administer the anti-tumor compound of the invention in amounts that excess, or even far exceed, the above-stated, preferred dosage range to effectively and aggressively treat particularly advanced or lethal tumors.

In the case of using the cell cycle inhibitor of the invention as a biochemical test reagent, the compound of the invention inhibits the progression of the cell cycle when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound of the invention for use as a cell cycle inhibitor is generally in the range of about 1 to about 100 μg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

From a pharmaceutical perspective, certain embodiments provide methods for preventing or treating fungal infections and/or a pathogenic fungus in a subject, involve administering to the subject a composition including a phenylahistin or its analog, for example, administering the phenylahistin or its analog in an amount and manner which provides the intended antifungal effect.

Other embodiments include the treatment or prevention of infection in a patient by a pathogenic fungus such as those listed above or referred to below.

Another embodiment relates to the treatment or prevention of infection in a patient by a pathogenic fungus which is resistant to one or more other antifungal agents, especially an agent other than phenylahistin or its analog, including e.g. amphotericin B or analogs or derivatives thereof (including 14(s)-hydroxyamphotericin B methyl ester, the hydrazide of amphotericin B with 1-amino-4-methylpiperazine, and other derivatives) or other polyene macrolide antibiotics, including, e.g., nystatin, candicidin, pimaricin and natamycin; flucytosine; griseofulvin; echinocandins or aureobasidins, including naturally occurring and semi-synthetic analogs; dihydrobenzo[a]napthacenequinones; nucleoside peptide antifungals including the polyoxins and nikkomycins; allylamines such as naftifine and other squalene epoxidease inhibitors; and azoles, imidazoles and triazoles such as, e.g., clotrimazole, miconazole, ketoconazole, econazole, butoconazole, oxiconazole, terconazole, itraconazole or fluconazole and the like. For additional conventional antifungal agents and new agents under deveopment, see e.g. Turner and Rodriguez, 1996 *Current Pharmaceutical Design,* 2:209–224. Another embodiment involves the treatment or prevention of infection in a patient by a pathogenic fungus in cases in which the patient is allergic to, otherwise intolerant of, or nonresponsive to one or more other antifungal agents or in whom the use of other antifungal agents is otherwise contra-indicated. Those other antifungal agents include, among others, those antifungal agents disclosed above and elsewhere herein.

In the foregoing methods for treatment or prevention, a phenylahistin or its analog, is administered to the subject in an effective antifungal amount.

Other embodiments relate to the treatment or prevention of infection by a pathogenic fungus in a patient by administration of a phenylahistin or its analog, in conjunction with the administration of one or more other antifungal agents, including for example, any of the previously mentioned agents or types of agents (e.g. in combination with treatment with amphotericin B, preferably in a lipid or liposome formulation; an azole or triazole such as fluconazole, for example; an aureobasidin; dihydrobenzo[alnapthacenequinone; or an echinocardin) as well as with a different phenylahistin or its analog.

The phenylahistin or its analog may be administered before, after or at the same time the other antifungal agent is administered. In certain embodiments, the combination therapy will permit the use of reduced amounts of one or both antifungal components, relative to the amount used if used alone.

Still other embodiments relate to administration of a phenylahistin or its analog to a subject for the treatment or prevention of infection by a pathogenic fungus, where the subject is immunosuppressed or immunocompromised, e.g. as the result of genetic disorder, disease such as diabetes or HIV or other infection, chemotherapy or radiation treatment for cancer or other disease, or drug- or otherwise induced immunosuppression in connection with tissue or organ transplantation or the treatment of an autoimmune disorder. Where the patient is being or will be treated with an immunosuppressive agent, e.g., in connection with a tissue or organ transplantation, a phenylahistin or its analog may be co-administered with the immunosuppressive agent(s) to treat or prevent a pathogenic fungal infection.

Another aspect of this invention is the treatment or prevention of infection by a pathogenic fungus in a patient infected, or suspected of being infected, with HIV, by administration of an antifungal phenylahistin or its analog, in conjunction with the administration of one or more anti-HIV therapeutics (including e.g. HIV protease inhibitors, reverse transcriptase inhibitors or anti-viral agents). The phenylahistin or its analog may be administered before, after or at the same time as administration of the anti-HIV agent(s).

Another aspect of this invention is the treatment or prevention of infection by a pathogenic fungus in a patient by administration of an antifungal phenylahistin or its analog, in conjunction with the administration of one or more other antibiotic compounds, especially one or more antibacterial agents, preferably in an effective amount and regiment to treat or prevent bacterial infection. Again, the phenylahistin or its analog may be administered before, after or at the same time as administration of the other agent(s).

Pathogenic fungal infections which may be treated or prevented by the disclosed methods include, among others, Aspergillosis, including invasive pulmonary aspergillosis; Blastomycosis, including profound or rapidly progressive infections and blastomycosis in the central nervous system; Candidiasis, including retrograde candidiasis of the urinary tract, e.g. in patients with kidney stones, urinary tract obstruction, renal transplantation or poorly controlled diabetes mellitus; Coccidioidomycosis, including chronic disease which does not respond well to other chemotherapy; Cryptococcosis; Histopolasmosis; Mucormycosis, including e.g. craniofacial mucormycosis and pulmonary mucormycosis; Paracoccidioidomycosis; and Sporotrichosis. It should be noted that administration of a composition comprising an antifungal amount of one or more phenylahistin or its analogs may be particularly useful for treating or preventing a pathogenic fungal infection in a mammalian subject where the fungus is resistant to one or more other antifungal therapies, or where the use of one or more other antifungal therapies is contraindicated, e.g., as mentioned above.

Antifungal pharmaceutical compositions containing at least one antifungal phenylahistin or its analog, are also provided for use in practicing the disclosed methods. Those pharmaceutical compositions may be packaged together with an appropriate package insert containing, inter alia, directions and information relating to their antifungal use. Pharmaceutical compositions are also provided which contain one or more phenylahistin or its analog together with a second antifungal agent.

Methods of Treating Fungal Infections

Certain embodiments disclosed herein relate to methods for treating or preventing a pathogenic fungal infection, including for example Aspergillosis, including invasive pulmonary aspergillosis; Blastomycosis, including profound or rapidly progressive infections and blastomycosis in the central nervous system; Candidiasis, including retrograde candidiasis of the urinary tract, e.g. in patients with kidney stones, urinary tract obstruction, renal transplantaion or poorly controlled diabetes mellitus; Coccidioidomycosis, including chronic disease which does not respond well to other chemotherapy; Cryptococcosis; Histopolasmosis; Mucormycosis, including e.g. craniofacial mucormycosis and pulmonary mucormycosis; Paracoccidioidomycosis; and Sporotrichosis. The methods may involve administering at least one antifungal phenylahistin or its analog, as described above, to a human subject such that the fungal infection is treated or prevented. In certain embodiments the phenylahistin or its analog may be administered in conjunction with administration of one or more non-phenylahistin or its analog antifungal agents such as amphotericin B, or an imidazole or triazole agent such as those mentioned previously.

The pathogenic fungal infection may be topical, e.g., caused by, among other organisms, species of *Candida, Trichophyton, Microsporum* or *Epiderinophyton* or mucosal, e.g., caused by *Candida albicans* (e.g. thrush and vaginal candidiasis). The infection may be systemic, e.g., caused by *Candida albicans, Cryptococcus neoformans, Aspergillus fumigatus, Coccidiodes, Paracocciciodes, Histoplasma* or *Blastomyces* spp. The infection may also involve eumycotic mycetoma, chromoblastomycosis, cryptococcal meningitits or phycomycosis.

Further embodiments relate to methods for treating or preventing a pathogenic fungal infection selected from the group consisting of *Candida* spp. including *C. albicans, C. tropicalis, C. kefyr, C. krusei* and *C. galbrata; Aspergillus* spp. including *A. fumigatus* and *A. flavus; Cryptococcus neoibrmans; Blastomyces* spp. including *Blastomyces dermatitidis; Pneumocvstis carinii; Coccidioides immitis; Basidiobolus ranarum; Conidiobolus* spp.; *Histoplasma capsulatum; Rhizopus* spp. including *R. oryzae* and *R. microsporus; Cunninghamella* spp.; *Rhizoniucor* spp.; *Paracoccidioides brasiliensis; Pseudallescheria boydii; Rhinosporidium seeberi;* and *Sporothrix schenckii.* Again, the method may involve administering a nonimmunosuppressive antifungal phenylahistin or its analog to a patient in need thereof such that the fungal infection is treated or prevented without inducing an untoward immunosuppressive effect.

Further embodiments relate to methods for treating or preventing a pathogenic fungal infection which is resistant to other antifungal therapy, including pathogenic fungal infections which are resistant to one or more antifungal agents mentioned elsewhere herein such as amphotericin B, flucytosine, one of the imidazoles or triazoles (including e.g. fluconazole, ketoconazole, itraconazole and the other previously mentioned examples). The methods may involve administering to the patient one or more antifungal phenylahistin or its analog, in an amount and dosing regimen such that a fungal infection resistant to another antifungal therapy in the subject is treated or prevented.

Further embodiments relate to methods for treating or preventing a pathogenic fungal infection in a patient who is allergic to, intollerant of or not responsive to another antifungal therapy or in whom the use of other antifungal agents is otherwise contra-indicated, including one or more other antifungal agents mentioned elsewhere herein such as amphotericin B, flucytosine, one of the imidazoles or triazoles (including e.g. fluconazole, ketoconazole, itraconazole and the other previously mentioned examples). The methods may involve administering to such patient one or more antifungal phenylahistin or its analog, in an amount such that a fungal infection is treated or prevented.

Packaged Phenylahistin or Its Analogs

Certain embodiments relate to packaged phenylahistin or its analogs, preferably packaged nonimmunosuppressive antifungal phenylahistin or its analogs, which term is intended to include at least one phenylahistin or its analog, as described above, packaged with instructions for administering the phenylahistin or its analog(s) as an antifungal agent without causing a untoward immunosuppressive effects within a human subject. In some embodiments, the non-immunosuppressive antifungal phenylahistin or its analog is a member of one of the preferred subsets of compounds described above. The phenylahistin or its analog can be packaged alone with the instructions or can be packaged with another phenylahistin or its analog, raparnycin or another ingredient or additive, e.g., one or more of the ingredients of the pharmaceutical compositions. The package can contain one or more containers filled with one or more of the ingredients of the pharmaceutical compositions. Optionally associated with such container(s) can be a notice in the form prescribed by a governmental agency regulating the manufacture, use or sale of pharmaceutical or biological products, which notice reflects approval by the agency of manufacture, use or sale for human administration.

The following examples are meant to describe the preferred modes of making and using the invention, i.e., of isolating, preparing, characterizing, and using certain preferred embodiments of the invention. Variations in the details of the particular methods employed and in the precise chemical compositions obtained will undoubtedly be appreciated by those of skill in the art.

EXAMPLE 1

Production, Isolation and Purification of Racemic Phenylahistin (PLH)

During the course of screening for new cell cycle inhibitors, see Roberge, M.; Tudan, C; Hung, S. M. F.; Harder, K. W.; Jirik, F. R.; Anderson, H. *Cancer Res.* 1994, 54, 6115, a novel compound NSCL-96F037 was found in the culture broth of *Aspergillus ustus* NSC-F038. see Fukumoto; K.; Asari, T.; Harada, T. Japanese Patent P409188749, Sep. 4, 1996 (Japanese). *A. ustus* NSC-F038 and NSC-F037 fungal strains were deposited with the National Institute of Bioscience and Human-Technology, Japan, Agency of Industrial Science and Technology, Ministry of International Trade and Industry, *A. ustus* NSC-F037 was designated FERM P-15829 and *A. ustus* NSC-F038 was designated FERM P-15830. The structure and biological activity of the compound initially designated NSCL-96F037 and of several of its derivatives were determined and are herein described. The compound initially designated NSCL-96F037 is herein also termed "phenylahistin" (PLH), and has the following structure:

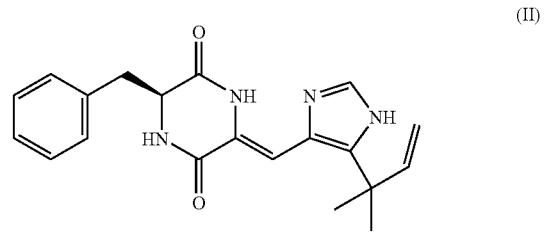

(II)

A. Production, Isolation and Purification of PLH from *Aspergillus ustus* NSC-F037

In each of 18 mm-diameter, 180 mm-length test tubes, 5 ml of sterilized production medium (production medium: glucose 5 g/l, glycerin 20 ml/l, cotton seed lees 20 g/l, yeast extract 2 g/l, sodium chloride 2.5 g/l, calcium carbonate 4 g/l (pH6.5)) was placed. The number of so-prepared test tubes was 1,700 (total culture medium: 8.5 liter). Each test tube was inoculated with 50 µl of *Aspergillus ustus* NSC-F037 fungus suspension prepared by suspending conidia of the strain in sterilized water and the culture broth was incubated for 5 days at 27° C. under reciprocal shaking (260 rpm). The culture broth in each test tube was added with 10 ml. of acetone and was extracted for one (1) day at room temperature. Impurities were then removed by filtration and the filtrate (approximately 20 liters) was vacuum-concentrated to distill off the acetone. Nine liters of ethyl acetate was added to the remaining water layer to effect extraction. The ethyl acetate layer was de-watered with sodium sulfate. Vacuum concentration and drying were conducted to obtain a solid which was subjected to silica gel open column chromatography (chloroform-methanol system) to isolate the antitumor activity fraction. This fraction was vacuumed-concentrated and dried to a solid, dissolved in a small amount of 70% methanol, subjected to high performance liquid chromatography using a Senshu Pack ODS-5251-SS 20 mm-diameter×250 mm (Senshu Science Kabushiki Kaisha) to conduct purification with a mobile phase: methanol/water 7/3 condition and to isolate a fraction exhibiting antitumor activity. This fraction was vacuum-concentrated and dried to a solid, subject to high performance liquid chromatography using a Senshu Pack Aquaseal SS5251(60) 20 mm-diameter×250 mm (Senshu Science Kabushiki Kaisha) to conduct purification with a mobile phase: chloroform/methanol 95/5 and to isolate the antitumor activity fraction. This fraction was vacuum-concentrated to obtain a transparent oily substance. This was suspended in a small amount of benzene and the result was vacuum concentrated and dried to a solid, thereby yielding 25 mg of NSCL-96F037, also herein termed phenylahistin (PLH).

B. Production, Isolation and Purification of PLH from *Aspergillus ustus* NSC-F038

The same steps as above were conducted except *Aspergillus ustus* NSC-F038 was used instead of *Aspergillus ustus* NSC-F037. It was determined that the ability of *Aspergillus ustus* NSC-F038 to produce the antitumor substance NSCL-95F037 was approximately four times that of NSC-F037. Specifically, from NSC-F037, approximately 2.9 mg phenylahistin was purified per liter of culture medium, while from NSC-F038, approximately 11.8 mg of phenylahistin was purified per liter of culture medium.

The production of phenylahistin by *A. ustus* NSC-F038 was also determined to be related to the conidia formation of the fungus. Therefore, the fungus was cultured on an agar medium containing glucose (0.5%), glycerol (2%), yeast extract (0.2%), Pharmamedia (Traders Protein) (2%), NaCl (0.25%) and agar (1.5%), adjusted to pH 6.5 before sterilization. This medium was suitable for the conidia formation at 28° C. for 8 days. The cultured agar media (200 plates; 4L) were then extracted with ethyl acetate. The extract was initially subject to silica gel column chromatography under an ethyl acetate-acetone stepwise gradient, followed by a second silica gel column and eluted with 2% methanol in chloroform. The fractions that exhibited cell cycle inhibitory activity were collected and evaporated, then dissolved in ethyl acetate and left two days at room temperature. The active substance was precipitated to yield 330 mg of a white amorphous powder with the following physical and spectroscopic characteristics: melting point: 233–236° C.; $[\alpha]_D^{22}$ +123° (c=0.13, MeOH); UV (MeOH) 8 max (log,): 202 (4.38), 233 sh (4.05), 320 (4.43); IR (KBr pellet) <max: 3440, 3240, 1670, 1640, 1440 cm$^{-1}$; HR-FAB-MS (m/z) 350.1741 (M$^+$, calcd. for $C_{20}H_{22}N_4O_2$: 350.1743).

The fungus *A. ustus* NSC-F038 was, alternatively, cultured is 20 ml of a culture medium comprising 0.5% glucose, 2% glycerin, 0.2% yeast extract, 2% cotton seed lees, 0.25% sodium chloride 2.5 g/l and 1.5% agar (pH6.5) to form a planar medium in a 9 cm-diameter Petri dish. The culture medium was inoculated at 5 points with *Aspergillus ustus* NSC-F038 and incubated in the dark for 7 days at 26° C. to produce spores. The spores were harvested into 5 ml of sterilized water having Tween 20 added to a concentration of 0.05%, thereby obtaining a spore suspension. Each of 400 Petri dishes containing 20 ml of the same culture medium was inoculated with 0.1 ml of the spore suspension. Incubation was conducted in the dark at 26° C. for 8 days. The cultures were comminuted with a mixer, 8 liters of ethyl acetate were added, and the mixture left standing 2 days before extraction. The recovered ethyl acetate was then vacuum-concentrated to obtain 15 g of a brown syrup. The syrup was dissolved in 20 ml of ethyl acetate, and the solution was subject to a silica gel column (bed volume: 8 cm diameter×20 cm length) chromatography under ethyl acetate and eluted with acetone ethyl acetate (1:5). The eluate was fractionated in 500 ml lots in the order eluted. The active compound was eluted in the fifth to tenth lots. These elutes were then vacuum-concentrated to afford a dark-brown powder in a total amount of approximately 4.65 g. The dark-brown powder was then dissolved in 10 ml of chloroform and the solution was subject to silica gel column (bed volume: 5 cm diameter×30 cm length) chromatography under ethyl acetate and eluted first with 500 ml chloroform and then with methanol in chloroform (1:50).

The active compound was eluted with methanol in chloroform (1:50) to obtain a brown powder in a total amount of approximately 1.05 g. The brown powder was then thoroughly mixed with ethyl acetate and left to stand 2 days to precipitate out approximately 628 mg of a white powder (A) containing the active compound. A portion of the white powder (A) was hydrolyzed. The so-obtained phenylalanine was analyzed by high performance liquid chromatography using a chiral column. The presence of R-configuration and S-configuration phenylalanine was then confirmed in a standard manner, and it was determined that the white powder (A) was a racemic mixture of the enantiomers of phenylahistin.

Another portion of the white powder (A) was dissolved in ethyl acetate containing a small amount of methanol and left to stand for 7 days. As a result a light yellow crystalline solid 187 mg of a purified specimen of (+)-phenylahistin was obtained. These specimens were used in the following four examples, EXAMPLES 2 through 5, as therein described, to verify the cell-proliferation, antimicrobial, cell-cycle inhibiting effects of the compound of the invention.

EXAMPLE 2

Concentration of Phenylahistin (PLH) Effective in Inhibiting Cell Proliferation

Into each well of a 96-well microtiter plate, 100 μl of A-549 cells derived from human lung cancer prepared to 10$^5$ cells/ml in a culture medium obtained by adding 10% bovine fetus serum to EMEM culture medium (Nissui Seiyaku Co., Ltd.) having antitumor effect against A-549 cells derived from human lung cancer was placed. Methanol solution of racemic NSCL-96F037 obtained as in Example 1 was added to the wells of the uppermost row, specimens were diluted by the half-log dilution method and added, and the plate was incubated in a carbon dioxide gas incubator at 37° C. for 48 hours. The result was added in lots of 10 μl with MTT reagent (3-(4,5-dimethyl-2-thiazole)-2,5-diphenyl-2H-tetrabromide) (1 mg/ml·PBS), followed by incubation in a carbon dioxide gas incubator at 37° C. for 6 hours. The culture medium was discarded and the crystal of produced in the cells was dissolved in 100 μl/well of dimethylsulfoxide. Absorption of 595 nm light was then measured with a microplate reader. By comparing the light absorptions of the untreated cells to that of cells treated with a specimen of a known concentration, the specimen concentration that inhibited cell proliferation 50% (IC$_{50}$) was calculated, thus obtaining an IC$_{50}$=0.3 μg/ml.

EXAMPLE 3

Antimicrobial Test of Phenylahistin (PLH)

Using colibacillus strain JM109 as a gram-negative bacterium, *Bacillus natto* as a gram-negative bacterium and *Aspergillus niger* IFO6341 as a mold, the following antimicrobial test was conducted by the filter paper agar flat plate method, wherein 100 μg of specimen was placed on 9 mm filter paper, dried in air, and standard agar culture medium was used for bacteria and potato dextrose agar culture medium for mold. No antimicrobial activity was observed. An antimicrobial test was further conducted by the liquid culture medium dilution method using the yeast strain *Saccharomyces cerevisise* HF7C. Again, no antimicrobial activity was observed, indicating that the racemic NSCL-96F037 (phenylahistin) obtained in EXAMPLE 1 had high animal cell-specific proliferation inhibiting activity.

EXAMPLE 4

Cell Cycle Inhibiting Activity of Phenylahistin (PLH)

Cell strain A431 derived from human lung cancer was used. EMEM culture medium containing 10% bovine fetus serum and 1% MEM nonessential amino acid solution (SIGMA M2025) was used to incubate A431 cells at 37° C. in an incubator saturated with 5% carbon dioxide gas and water vapor. The refined specimen of racemic phenylahistin obtained in EXAMPLE 1 was added to the cells in the log-growth phase and progression of the cell cycle was analyzed by flow cytometer and microscopic observation. The results, shown in Table 1, indicate that this phenylahistin was useful as a cell cycle inhibitor.

TABLE 1

Cell cycle inhibiting activity

| Concentration (μg/ml) | Inhibiting effect |
|---|---|
| 0.5 | Absent |
| 1.0 | Absent |
| 2.0 | Slight |
| 4.0 | Slight |
| 8.0 | Present |
| 16.0 | Present |
| 32.0 | Present |

Inhibiting effect evaluation criteria were as follows:
Present: The cell cycle stopped at the G2/M phase in not less that 50% of the cells.
Slight: The cell cycle stopped at the G2/M phase in not less than 10% and less than 50% of the cells.
Absent: The cell cycle stopped at the G2/M phase in less than 10% of the cells.

EXAMPLE 5

Cell Proliferation Inhibiting Effect of Phenylahistin (PLH)

K-562, human chronic myelogenic leukemia cells were cultured in RPMI164 culture medium (containing 10% bovine fetus serum) and A-431 human pudendal epithelial squamous cancer cells were cultured in DMEM culture medium, containing 10% bovine fetus serum. To these a continuous dilution series of the (+)-phenylahistin obtained in EXAMPLE 1 was added. After 48-hours incubation, a MTT reagent was added to measure growth. The human chronic myelogenic leukemia cells exhibited an $IC_{50}$ of 13.3 μg/ml, while the human pudendal epithelial squamous cancer cells exhibited an $IC_{50}$ of 2.9 μg/ml, indicate that (+)-phenylahistin was useful as an antitumor agent.

EXAMPLE 6

Characterization and Resolution of Enantiomers of Phenylahistin (PLH)

A. Racemic Phenylahistin

Phenylahistin (PLH) had the molecular formula, $C_{20}H_{22}N_4O_2$, which was determined by HR-FAB-MS (mz found: 350.1741 (M+), calcd. for $C_{20}H_{22}N_4O_2$: 350.1743). In the IR spectrum, the absorption at 3440 cm$^{-1}$ corresponds to the N—H group, and strong absorptions at 1670 and 1640 cm$^{-1}$ indicated the existence of amide groups. These findings together with the absence of the amide II band near 1550 cm$^{-1}$ in the spectrum suggested the presence of the diketopiperazine system in phenylahistin, according to the technique described in Steyn, P. S. *Tetrahedron* 1973, 29, 107, which was also supported by the negative ninhydrin reaction.

The $^{13}$C-NMR spectrum of phenylahistin, with atomic positions as indicated in Structure (IV), summarized in the first column of Table 2, showed 17 resolved peaks with three overlapping carbon signals. The multiplicity of these peaks was determined by analysis of its DEPT spectra. The $^1$H-NMR spectrum displayed 22 proton signals, listed in the second column of Table 2, including three exchangeable protons. All bond connections between proton and carbon were interpreted by $^1$H-$^{13}$C COSY.

TABLE 2

Table $^{13}$C and $^1$H NMR Assignment of Phenylahistin in CDCl$_3$

| Positions | δ C* | δ H** |
|---|---|---|
| 1 (NH) | — | 9.48(1H, br s) |
| 2 | 132.56 d | 7.55(1H, s) |
| 4 | 132.18 s | — |
| 5 | 136.83 s | — |
| 6 | 105.62 d | 6.88(1H, s) |
| 7 | 123.64 | — |
| 8 (NH) | — | 12.08(1H, br s) |
| 9 | 164.73 s | — |
| 10 | 57.14 d | 4.35(1H, ddd, J=10, 4, 3# Hz) |
| 11 (NH) | — | 5.82(1H, br s) |
| 12 | 159.94 s | — |
| 13 | 41.23 t | 2.95(1H, dd, J=14, 10 Hz) |
|  |  | 3.49(1H, dd, J=14, 4 Hz) |
| 14 | 135.45 s | — |
| 15, 19 | 129.52 d | 7.25(2H, d, J=7 Hz) |
| 16, 18 | 129.07 d | 7.33(2H, t, J=7 Hz) |
| 17 | 127.45 d | 7.27(1H, t, J=7 Hz) |
| 20 | 37.61 s | — |
| 21 | 144.66 d | 6.02(1H, dd, J=18, 11 Hz) |
| 22 | 113.29 t | 5.13(1H, d, J=18 Hz) |
|  |  | 5.17(1H, d, J=11 Hz) |
| 23, 24 | 27.97 q | 1.49(6H, s) |

*125 MHz, including multiplicity assignment on the basis of DEPT summary. Chemical shifts in ppm from CDCl$_3$ as an internal standard (77.00 ppm).
**500 MHz, Chemical shifts in ppm from TMS as an internal standard (0.00 ppm).
Coupling with 11-H was observed by decoupling experiment.

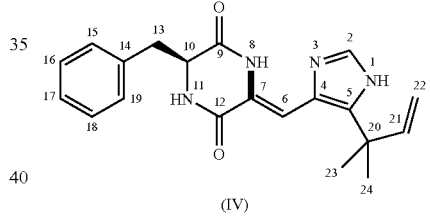

(IV)

The $^1$H NMR and $^1$H -$^1$H COSY spectra revealed only the presence of four partial structures: a monosubstituted benzene ring, methylene protons being coupled to a methine proton, which was also coupled to an exchangeable proton, one geminal methyl group and a vinyl group. Since quaternary carbons prevented constructing further partial structures, the PFG-HBMC spectrum were t measured. A partial structure was determined on the basis of the long-range correlations of C-9, C-13, and C-14, which were observed in the spectrum. The carbon chemical shift of C-9 (* 164.73) indicated that it was a carbonyl carbon. Therefore, that partial structure was determined to be a phenylalanine residue. In the same manner, a second partial structure was determined from the correlations of C-5, C-20, C-21, C-23 and C-24, which showed an isoprenyl group binding to quaternary sp$^2$ carbon (* 136.83). The diketopiperazine ring was also constructed from the interpretation of correlations between respectively, C-7 and 11-H, C-10 and 8-H, C-12 and 8-H, and C-12 and 10-H in the PFG-HMBC spectrum. The dehydrohistidine moiety was estimated from the remaining three carbons, two nitrogens and three hydrogens, and this structure was supported by correlation signals of C-4, C-5, C-7, and C-12. The correlation signal between C-5 and H-6 indicated that the isoprenyl group was placed in the C-5 of the imidazole ring. This structure was confirmed by analysis of the PFG-$^{15}$N-HMBC spectrum. The nitrogen residues were assigned as follows: N1 (* 159); N3 (* 253); N8 (* 133); N11(* 109) ($^{15}$N-formamide internal standard at * 112.4 ppm).

From these data, the planar structure of phenylahistin was established. The stereochemistry of the C-6–C-7 double bond was suggested to be Z by the low field shift of 8-H (N H: * 12.08), which was further explained by hydrogen-bonding between the 8-H proton and N-3 of the imidazole ring, as in the case of aurantiamine.

It was also determined that phenylahistin has a chiral center at the C-10 position. Chiral HPLC analysis of the phenylalanine was conducted according to methods described in Larsen, T. O et al., Phytochemistry (1992) 31, 1613, under the following conditions: HPLC conditions: column; Crownpak CR(+) N4.0×150 mm (Daicel Chemical Industries, Ltd.), mobile phase; H$_2$O (pH 2, adjusted with perchloric acid), flow rate; 0.8 ml/min, detector; UV 8 200 nm. Phenylalanine was obtained from the acidic hydrolysate of the amorphous white powder of phenylahistin, see Yamazaki, M. et al., Tetrahedron Lett. (1975) 27. The phenylalanine obtained from the hydrolysate of phenylahistin was identified using an amino acid analyzer and by measurement of EI-MS [(m+H)$^+$:166.2]); chrial HPLC indicated that the phenylahistin was a mixture of enantiomers in the ratio of approximately R:S=3:1. In order to examine the biological activity of each enantiomer, chiral resolution was carried out by chiral HPLC under the following conditions: column; Chiracel OD N4.6×250 mm (Daicel Chemical Industries, Ltd), mobile phase; n-hexane/ethanol=75/25, flow rate; 1.0 ml/min, temperature; 25° C. Absolute configuration was determined by analysis of phenylalanine obtained from (+)-phenylahistin using chiral HPLC.

B. Single-Crystal X-Ray Diffraction Analysis of Phenylahistin

A pale yellow crystal having approximately dimension 0.4×0.4×0.8 mm was obtained from the ethyl acetate solution of phenuylahistin. All X-ray measurements were made on a Rigaku AFC7R diffractometer with graphite monochromated CuKα radia and a rotating anode generator. Cell constants and an orientation matrixed for data collection were obtained from a least-squares refinement using the setting angles of 25 carefully centered reflections in the range of 77.59<26<79.03°. These crystal data are summarized in Table 3.

TABLE 3

Crystal data of (−)-phenylahistin

| | |
|---|---|
| Empirical formula | $C_{20}H_{22}N_4O_2$ |
| Formula weight | 350.42 |
| Crystal system | tetragonal |
| Lattice parameters: | a = 15.3509(7) Å |
| | o = 8.309(2) Å |
| | V = 1958.0(2) Å$^3$ |
| | Z = 4 |
| Space group | P4$_2$(#77) |
| D calc. | 1.189 g/cm$^3$ |
| μ (CuKα) | 6.37 cm$^{-1}$ |

Of the 2229 reflections which were collected, 2064 were unique ($R_{int}$=0.019). The intensities of the three representative reflections were measured after every 150 reflections. No decay collection was applied. The linear absorption coefficient: μ for CuKα is 6.37 cm$^{-1}$. Azimuthal scans of several reflections indicated no need for an absorption correction. The data were corrected for Lorentz and polarization effects. A correction for secondary extinction was applied. The structure was solved by direct methods, see SAPA91: Fan Hai-Fu (1991). Structure Analysis Programs with Intelligent Control, Rigaku Corporation, Tokyo, Japan, and expanded using Fourier techniques, see DIRDIF94: Beurskens, P. T. et al. (1994) the DIRDIF94 program system, Technical Report of the Crystallography Laboratory, University of Nijmegen, The Netherlands. Nonhydrogen atoms except for C22 were refined anisotropically, while C22 was refined isotropically. Some hydrogen atoms were refined isotropically, the est included in fixed positions. The final cycle of full-matrix least-squares refinement was based on 1724 observed reflections (I>1.50σ(I)) and 242 variable parameters and converged (largest parameter shift was 0.30 times its esd) with unweighted and weighted factors of :R=0.057, $R_w$=0.067. The maximum and minimum peaks on the final difference Fourier map corresponded to 0.20 and −0.12 e$^-$/A$^8$, respectively. All calculations were performed using the teXscan crystallographic software package of Molecular Structure Corporation.

The stereochemistry of C6–C7 double bond was confirmed to be Z, and the hydrogen bonding between 8(N)-H and N-3 was observed as speculated from low field-shift of 8(N)-H (δ12.08 ppm) in NMR study. Since the absolute configuration of C-10 position could not be determined by this X-ray analysis, we analyzed the configuration of phenylalanine which was obtained from acidic hydrolysate of the crystalline sample using chiral HPLC. The phenylalanine obtained from the crystalline sample was identical with the authentic sample of D-(+)-phenylalanine (R-configuration). Therefore, the absolute configuration of this crystalline sample of phenylahistin was established to be R.

Other derivatives of phenylahistin can be synthesized using the foregoing techniques or others well known organic synthesis techniques.

EXAMPLE 7

Synthesis and Physical Characterization of Phenylahistin Derivatives

A. Synthesis of Various Derivatives of Phenylahistin

Structural derivatives of phenylahistin were synthesized from the resolved enantiomers according to the following reaction schemes. In Reaction Scheme 1, shown in FIG. 1, the enantioners of phenylahistin were resolved, as described in Example 6, and each was subject to palladium-based catalytic reduction conditions for 2 hours, yielding two mono-reduced phenylahistin derivatives herein designated compounds 3 and 4. These compounds were in turn subject to palladium-based catalytic reduction conditions for 24 hours, yielding di-reduced phenylahistin derivatives, herein designated compounds 5 and 6.

Figure 2:
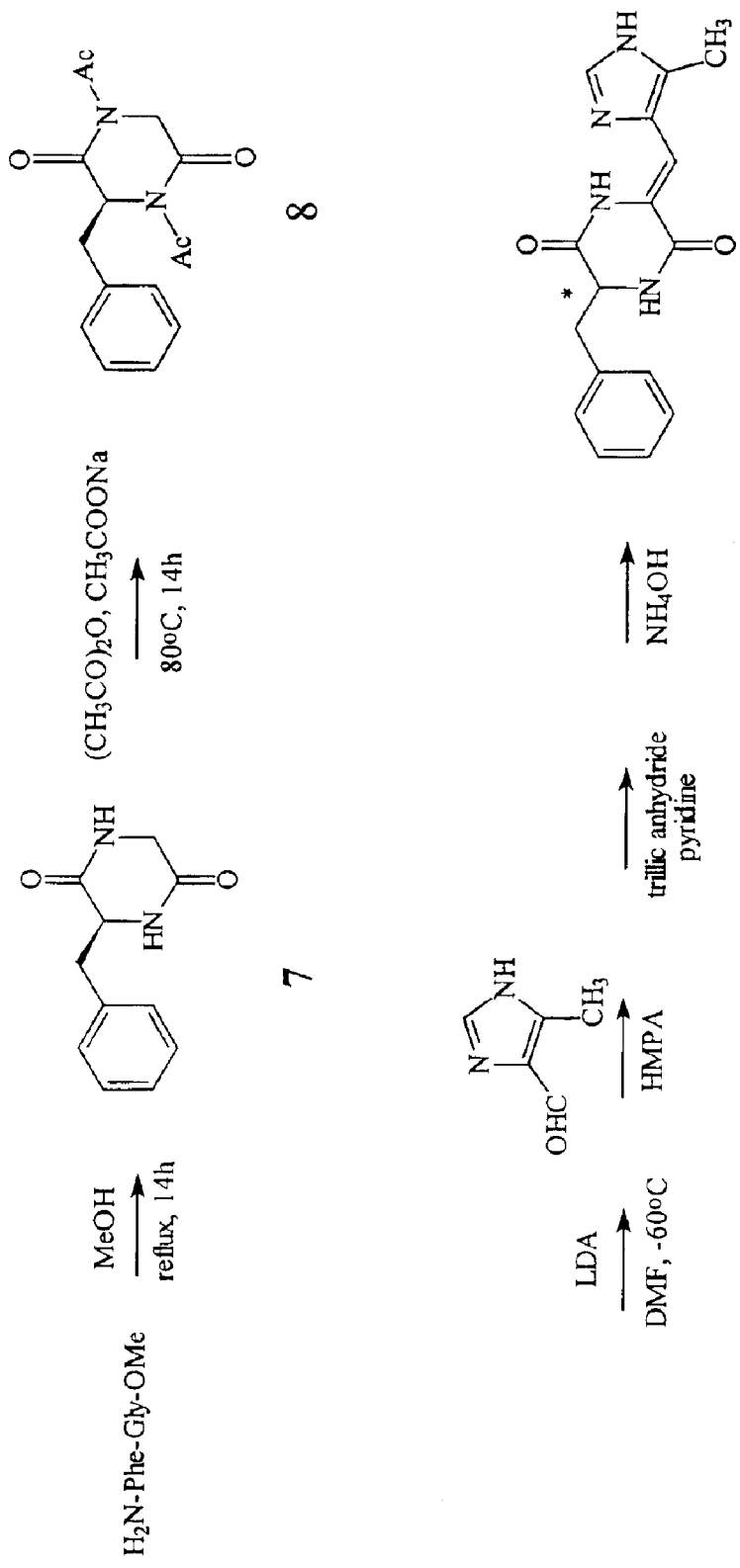
FIG. 2 illustrates Reaction Scheme 2, which shows a synthetic method for producing a compound of the invention, PLH-Cl, from $H_2$N-Phe-Gly-OMe. (The asterisk indicates that racemation occurred; (−):(+)=79:21.).

In Reaction Scheme 2, as shown in FIG. 2, the synthesis of the phenylahistin derivative designated PLH-C1, and alternatively designated compound 9, is described. This reaction scheme treats H$_2$N-Phe-Gly-OMe, a commercially available di-peptide derivative to yield PLH-C1, a derivative of PLH in which the isoprenyl moiety is replaced with a methyl group. Since partially racemization was occurred (21%), chiral resolution was carried out to obtain optically pure PLH-C1.

Figure 3:
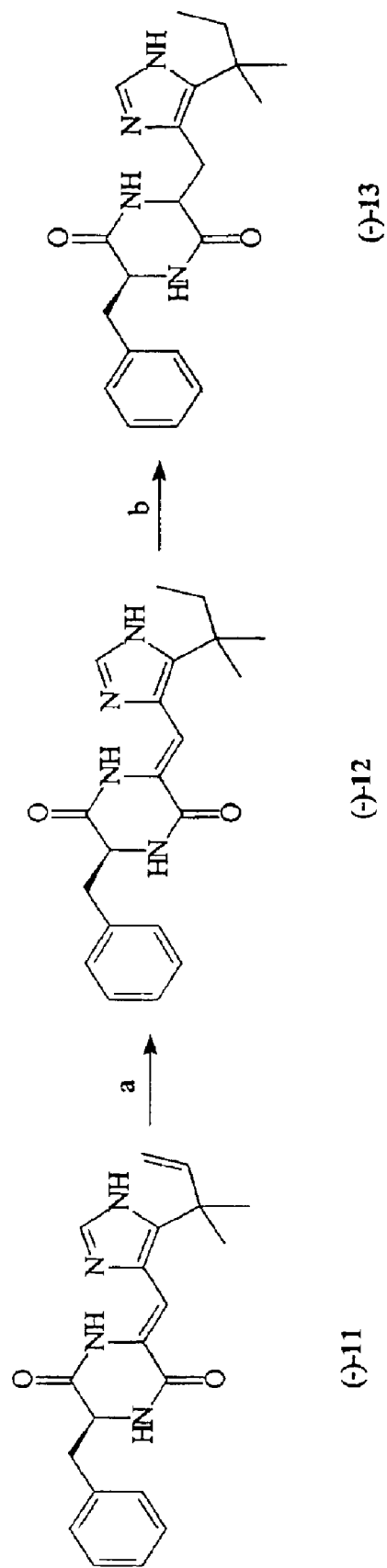
FIG. 3 illustrates Reaction Scheme 3, which shows the preparation of two reduced derivatives of (−)-phenylahistin, compounds identified as (−)-12 and (−)-13, which are respectively, identical to compounds 3 and 5 of FIG. 1.

In Reaction Scheme 3, as shown in FIG. 3, the synthesis of (−)-PLH-C1 is described. In the course of synthesizing this compound, another phenylahistin derivative, designated compound 7 is synthesized.

B. Physical Characteristics

These above-identified compounds were characterized as follows:

Compound 3. Colorless solid; mp 224–226° C.; [α]$_D^{25}$– 295° (c=0.15, MeOH), UV (MeOH) nm 322 (ε 23300), 231

(ε 8830), 203 (ε 16800); IR (KBr) cm$^{-1}$ 3310, 3220, 2970, 1670, 1440; $^1$H NMR (270 MHz, CDCl$_3$) δ 12.09 (br s, 1H), 8.98 (br s, 1H), 7.56 (s, 1H), 7.29–7.38 (m, 5H), 6.87 (s, 1H), 5.67 (s, 1H), 4.34 (ddd, J=2, 3, 10 Hz, 1H), 3.51 (dd, J=3, 14 Hz, 1H), 2.29 (dd, J=10, 14 Hz, 1H), 1.74 (q, J=7 Hz, 2H), 1.40 (s, 6H), 0.74 (t, J=7 Hz 3H); $^{13}$C NMR (67.5 MHz, CDCl$_3$) δ 164.6, 159.9, 138.1, 135.5, 132.2, 132.1, 129.5 (2C), 129.1 (2C), 127.4, 123.6, 105.4, 57.2, 41.3, 36.2, 35.4, 27.9 (2C), 9.2; High-resolution MS m/z 352.1926 (M$^+$) (Calcd for C$_{20}$H$_{24}$N$_4$O$_2$: 352.1899). Anal. calculated for C$_{20}$H$_{24}$N$_4$O$_2$: C,68.16; H,6.86; N,15.90. Found: C,68.34, 6.78, 15.82.

Compound 4: Colorless solid; mp 222–223° C; [α]$_D^{25}$ +284° (c=0.10, MeOH), UV (MeOH) nm 322 (ε 22800), 231 (ε 8720), 203 (ε 16300); IR (KBr) cm$^{-1}$ 3310, 3220, 2970, 1670, 1440; $^1$H NMR (270 MHz, CDCl$_3$) δ 12.09 (br s, 1H), 8.98 (br s, 1H), 7.56 (s, 1H), 7.29–7.38 (m, 5H), 6.87 (s, 1H), 5.67 (s, 1H), 4.34 (ddd, J=2, 3, 10 Hz, 1H), 3.51 (dd, J=3, 14 Hz, 1H), 2.29 (dd, J=10, 14 Hz, 1H), 1.74 (q, J=7 Hz, 2H), 1.40 (s, 6H), 0.74 (t, J=7 Hz 3H); $^{13}$C NMR (67.5 MHz, CDCl$_3$) δ 164.6, 159.9, 138.1, 135.5, 132.2, 132.1, 129.5 (2C), 129.1 (2C), 127.4, 123.6, 105.4, 57.2, 41.3, 36.2, 35.4, 27.9 (2C), 9.2; High-resolution MS m/z 352.1932 (M$^+$) (Calcd for C$_{20}$H$_{24}$N$_4$O$_2$: 352.1899). Anal. calculated for C$_{20}$H$_{24}$N$_4$O$_2$: C,68.16; H,6.86; N,15.90. Found: C,68.09, 6.87, 15.84.

Compound 5: Colorless solid; mp 224–225° C.; [α]$_D^{25}$ −96° (c=0.16, MeOH), UV (MeOH) nm 257 (ε 194), 205 (ε 18100), IR (KBr) cm$^{-1}$ 3380, 3200, 2970, 1670, 1440; $^1$H NMR (270 MHz, DMSO-d$_6$) δ 11.55 (br s, 1H), 8.25 (br s 1H), 7.86 (br s 1H), 7.41 (s, 1H), 7.29–7.14 (m, 5H), 4.24 (br s, 1H), 3.94 (brd, J=11 Hz, 1H), 3.11 (dd, J=14, 4 Hz, 1H), 2.88 (dd, J=14, 5 Hz, 1H), 2.82 (dd, J=15, 2 Hz, 1H), 1.45 (q, J=7 Hz, 2H), 1.32 (dd, J=15, 11 Hz, 1H), 1.13 (s, 3H), 1.12 (s, 3H), 0.60 (t, J=7 Hz, 3H); $^{13}$C NMR (67.5 MHz, DMSO-d$_6$) δ 166.9 165.4, 135.9, 132.5, 131.2, 130.3 (2C), 127.9 (2C), 126.6, 55.7, 54.3, 38.2, 35.0, 34.3, 31.9, 27.6, 27.5, 9.1; High-resolution MS m/z 354.2098 (M$^+$) (Calcd for C$_{20}$H$_{26}$N$_4$O$_2$: 354.2055). Anal. calculated for C$_{20}$H$_{26}$N$_4$O$_2$: ⅓H$_2$O: C,66.64; H,7.46; N,15.54. Found: C,66.75, 7.41, 15.52.

Compound 6: Colorless solid; mp 226–227° C.; [α]$_D^{25}$ +99° (c=0.10, MeOH), UV (MeOH) nm 257 (ε 174), 205 (ε 18200), IR (KBr) cm$^{-1}$ 3380, 3200, 2970, 1670, 1440; $^1$H NMR (270 MHz, DMSO-d$_6$) δ 11.55 (br s, 1H), 8.25 (br s. 1H), 7.86 (br s, 1H), 7.41 (s, 1H), 7.29–7.14 (m, 5H), 4.24 (br s, 1H), 3.94 (br d, J=11 Hz, 1H), 3.11 (dd, J=14, 4 Hz, 1H), 2.88 (dd, J=14, 5 Hz, 1H), 2.82 (dd, J=15, 2 Hz, 1H), 1.45 (q, J=7 Hz, 2H), 1.32 (dd, J=15, 11 Hz, 1H), 1.13 (s, 3H), 1.12 (s, 3H), 0.60 (t, J=7 Hz, 3H); $^{13}$C NMR (67.5 MHz, DMSO-d$_6$) δ 166.9, 165.4, 135.9, 132.5, 131.6, 131.2, 130.3 (2C), 127.9 (2C), 126.6, 55.7, 54.3, 38.2, 35.0, 34.3, 31.9, 27.6, 27.5, 9.1; High-resolution MS m/z 354.2110 (M$^+$) (Calcd for C$_{20}$H$_{26}$N$_4$O$_2$: 354.2055). Anal. calcd for C$_{20}$H$_{26}$N$_4$O$_2$: ½H$_2$O: C,66.09; H,7.49; N,15.41. Found: C,65.80, 7.50, 15.30.

Compound 7: Cyclo-Gly-Phe (7). White powder; mp 262–263° C. (decomp.); [α]$_D^{25}$ +60° (c=0.15, DMSO); UV (MeOH) nm 257 (ε 101), 206 (ε 5770) IR (KBr) cm$^{-1}$ 3340, 3200, 3060, 1680, 1470, 1340; $^1$H NMR (270 MHz,DMSO-d$_6$) δ 8.16 (br s, 1H), 7.90 (br s, 1H), 7.32–7.15 (m, 5H), 4.07 (br dd, J=7, 4 Hz, 1H), 3.35 (dd, J=18, 3 Hz, 1H), 3.10 (dd, J=14, 4 Hz, 1H), 2.88 (dd, J=14, 5 Hz, 1H), 2.75 (d, J=18 Hz, 1H); $^{13}$C NMR (DMSO-d6) δ 167.1, 165.7, 136.0, 130.1 (2C), 128.1 (2C), 126.8, 55.5, 43.7, 38.8; Anal. calculated for C$_{11}$H$_{12}$N$_2$O$_2$: ⅓H$_2$O: C,63.57; H,6.01; N,13.48. Found: C,63.85, H,5.86, N,13.40.

Compound 8: Colorless solid; mp 84–85° C.; [α]$_D^{25}$ +7.8° (c=0.52, MeOH); UV (MeOH) nm 209 (ε 20400); IR (KBr) cm$^{-1}$ 1720, 1400, 1380, 1240; $^1$H NMR (270 MHz, CDCl$_3$) δ 7.33–7.26 (m, 3H), 7.08–7.05 (m, 2H), 5.44 (t, J=5 Hz, 1H), 4.49 (d, J=19 Hz, 1H), 3.35 (dd, J=14, 5 Hz, 1H), 3.20 (dd, J=14, 5 Hz, 1H), 2.58 (s, 3H), 2.55 (s, 3H), 2.48 (d, J=19 Hz, 1H); $^{13}$C NMR (67.5 MHz, CDCl$_3$) δ 171.2, 171.0, 167.9, 166.0, 134.3, 129.7 (2C), 129.1 (2C), 128.2, 59.0, 46.0, 38.7, 27.1, 26.8; MS (ESI) m/z 205 (M+H); MS (ESI) m/z 311 (M+Na)$^+$; Anal. calculated for C$_{15}$H$_{16}$N$_2$O$_4$: C, 62.49; H, 5.59; N, 9.72. Found: C, 62.50, H,5.50, N,9.67.

Compound 9: Colorless solid; mp 285–286° C. (decompose); [α]$_D^{25}$ −267° (c=0.21 DMSO); UV (MeOH) nm 319 (ε 22800); IR (KBr) cm$^{-1}$ 3400, 3180, 1680, 1450; $^1$H NMR (270 MHz, DMSO-d$_6$) δ 11.50 (br s, 1H), 8.35 (br s, 1H), 7.74 (s, 1H), 7.24–7.14 (m, 5H), 6.20 (s, 1H), 4.48 (m, 1H), 3.33 (br s, 1H), 3.20 (dd, J=14, 4 Hz, 1H), 2.93 (dd, J=14, 5 Hz, 1H), 2.19 (s, 1H); $^{13}$C NMR (67.5 MHz, DMSO-d$_6$) δ 164.2, 158.7, 135.6, 134.6, 132.3, 130.0 (2C), 128.0 (2C), 127.5, 126.6, 123.4, 101.7, 55.9, 38.7, 8.9; High-resolution MS m/z 296.1261 (M$^+$) (Calcd for C$_{16}$H$_{16}$N$_4$O$_2$: 296.1273). Anal. calculated for C$_{16}$H$_{16}$N$_4$O$_2$·⅓H$_2$O; C,64.07; H,5.51; N,18.68. Found: C,64.39, H,5.65, N,18.29.

EXAMPLE 8

Relative Cytotoxic Effects of the Phenylahistin Enantiomers

The cytotoxic effects of the enantiomers of phenylahistin on P388 murine leukemia cells were examined. IC$_{50}$ values of (−)-phenylahistin (S-configuration) (92.2% e.e.) and (+)-phenylahistin (R-configuration) (97.8% e.e.) were 3.5×10$^{-7}$ M and 3.8×10$^{-5}$ M, respectively. Judging from the content of (−)-phenylahistin in (+)-phenylahistin, (+)-phenylahistin was considered to have relatively low cytotoxicity to P388 cells.

EXAMPLE 9

Biological Activity of Phenylahistin and its Derivatives

The biological activity of phenylahistin and its derivatives, synthesized as described in EXAMPLE 7 and established according to the methods described in EXAMPLES 5 and 11, are summarized in Table 4.

TABLE 4

Comparative Biological Activity of Phenylahistin and its Derivatives

| Compound | IC$_{50}$ for P388 Proliferation* (μM) | IC$_{50}$ for Microtubule Protein Polymerization** (μM) |
| --- | --- | --- |
| 1 | 0.21 | 25 |
| 2 | 10 | >200 |
| 3 | 0.23 | 30 |
| 4 | 19 | >200 |
| 5 | >200 | >200 |
| 6 | >200 | >200 |
| 7 | >200 | >200 |
| 9 | 7.5 | >200 |
| Cyclo-His-Phe*** | >200 | >200 |

*IC$_{50}$ was determined by Alamar Blue ™ assay.
**Microtubule protein was prepared from bovine brain by two cycles of assembly and disassembly method. The concentration of microtubule protein used for the assay was 1.5 mg/ml.
***Obtained from SIGMA (code No. C2615)

EXAMPLE 10

Effect of Phenylahistin on the Cell Cycle Progression of P388

The effect of phenylahistin on the cell cycle progression of P388 cells was also investigated using a flow cytometer, as described in Krishan, A., J. Cell Biol. (1975) 66, 188–193. P388 cells in the log growth phase were seeded into flasks and cultured for 14 hours, and then various concentrations of phenylahistin were added to each flask. After an 8-hour incubation, the cells were harvested and fixed with 50% MeOH at −20° C. overnight. The cells were washed with 30% MeOH and then with 10 mM PBS, and treated with 50 :g/ml propidium iodide at 4° C. for 2 hours. DNA histograms were obtained using a flow cytometer (Cyto ACE-300:JASCO).

(−)-Phenylahistin exhibited cell cycle inhibitory activity at $1\times10^{-6}$ M, but (+)-phenylahistin (97.8% e.e.) had no effect at $1\times10^{-5}$ M. Therefore, the active configuration of phenylahistin was determined to be S, and it was determined that this configuration most effectively inhibited cell cycle progression in the G2/M phase.

EXAMPLE 11

Effects of Phenylahistin on Microtubulin Function (−)-Phenylahistin ((−)-PLH) was shown to effect microtubule function, specifically via effecting the proliferation, mitosis, and microtubule structure of A549 cells (human lung carcinoma), and via inhibiting the in vitro polymerization of bovine brain microtubule protein and purified tubulin. In addition, competitive binding experiments using colchicine (CLC) and vinblastine (VLB), two typical antimitotic agents that bind to individual binding sites on tubulin, were used to establish the effect of (−)-PLH on the distinct binding sites on tubulin.

A. Materials. (−)-PLH was isolated from the agar-culture medium of *A. ustus* NSC-F038 (See, Kanoh, K. et al.: Bioorg. Med. Chem. Lett. (1997), 7, 2847–52, as disclosed in Example 1. CLC was obtained from Sigma (St. Louis, Mo.) and VLB was from Wako Pure Chemicals (Tokyo, Japan). [$^3$H]CLC was purchased from Du Pont/Boston Nuclear (New England, Mass.) and [$^3$H]VLB was from Amersham (Buckinghamshire, UK). A549 cell line (human lung carcinoma) was obtained from American Type Culture Collection (Rockville, Md.). A549 cells were cultured in phenol red free EMEM medium from Nissui Pharmaceuticals (Tokyo, Japan), supplemented with MEM non-essential amino acids (Sigma) and 10% fetal bovine serum from JRH Biosciences, (Lenexa, Kans.).

B. Alamar Blue™ Assay. Exponentially growing A549 cells were seeded into 96-well tissue culture plates ($2\times10^3$ cells/100 µl/well) and cultured for 16 hours. (−)-PLH or CLC was then added to each well at various concentrations, and the cells were cultured for an additional 48 hours. Live cells were counted using Alamar Blue™ from BioSource International (Camarillo, Calif.) as described in Ahmed, S. A., J. Immunol. Methods, (1994), 170, 211–24.

C. Mitotic Index. Exponentially growing A549 cells were seeded into 96-well tissue culture plates ($2\times10^3$ cells/100:1/well) and cultured for 16 hours. (−)-PLH or CLC was then added to each well at various concentrations, and the plates were incubated for an additional 24 hours. The number of cells in mitosis (round cells) and total cells in eight randomly selected fields were counted under a phase-contrast microscope. In a series of preliminary studies, it was confirmed that the round cells in this condition were cells in mitosis by using flow cytometry and Hoechst 33258 staining. The mitotic index represented the percentage of round cells among the total number of cells in the eight selected fields.

D. Immunocytochemistry. Immunocytochemical staining was performed using the method described by Yahara, I. et al., Cell (1978) 15, 251–259. A549 cells were cultured on glass coverslips and incubated with the test drug for 6 hours. The cells were then fixed with 3.7% formaldehyde for 30 min, permeabilized with 0.2% Triton X-100 for 5 min, and incubated with a mouse monoclonal antibody against α-tubulin (Calbiochem®, Oncogene Research Products, Cambridge, Mass.), followed by incubation with fluorescein isothiocyanate-conjugated goat anti-mouse IgG from Cosmo Bio Co., (Tokyo, Japan), and the cells were examined under an immunofluorescent microscope.

E. Microtubule Protein and Tubulin Preparation. Microtubule protein was prepared from bovine brain tissue by two cycles of assembly and disassembly according to the method of Tiwari, S. C. et al. Anal. Biochem, (1993), 215, 96–103. Tubulin was purified from microtubule protein by phosphocellulose chromatography see Algaier, J. et al. Biochim. Biophys. Acta, (1988), 954, 235–43, and tubulin purity was evaluated by polyacrylamide gel electrophoresis, as in Laemmli, U.K., Nature, (1970), 277, 680–85. Essentially, no microtubule-associated proteins were detected in this preparation. Protein concentrations were determined using the Coomassie® Protein Assay Reagent from Pierce (Rockford, Ill.).

F. Polymerization Assay. Polymerization of microtubule protein was monitored by an increase in turbidity at 37° C. in microtubule assembly buffer containing 100 mM MES, 0.5 mM $MgCl_2$, 1 mM EGTA and 1 mM GTP. See Johnson, K. A. et al., J. Mol. Biol., (1977), 117, 1–31. Polymerization of purified tubulin was measured using the same method except the microtubule assembly buffer contained 4 M glycerol. See Lee, J. C. et al., Biochemistry, (1975), 14, 5183–87. Microtubule protein and tubulin polymerization was initiated by a temperature shift from 0° C. to 37° C. and turbidity was measured on a DU-20 thermocontrolled spectrophotometer from Beckman (Fullerton, Calif.) at 360 nm. Drugs were dissolved in dimethyl sulfoxide (DMSO), which was used in all experiments at a final concentration of 2% (v/v).

G. Electron Microscopy. Microtubule protein (1.5 mg/ml) was polymerized at 37° C. for 20 min in the presence of 100 µM (−)-PLH or vehicle (DMSO). A portion of each sample was diluted 5-fold with 1% glutaraldehyde in the microtubule assembly buffer. Samples were then placed on formvar- and carbon-coated grids, stained with 2% uranyl acetate, and examined using a JEOLJEM-1200 EXII electron microscope JEOL (Tokyo, Japan).

H. Competition Assay. [$^3$H]CLC binding to tubulin was evaluated by the ultrafiltration method of Takahashi, M., et al., Biochim. Biophys. Acta, (1987) 926, 215–23, with only slight modifications: bovine brain tubulin (0.2 mg/ml) was incubated in the microtubule assembly buffer with various concentrations of [$^3$H]CLC for 20 min at 37° C.; each sample (200 µl) was applied to the reservoir of a UFC3LTK00 ultrafiltration unit from Nihon Millipore Ltd. (Yonezawa, Japan) and centrifuged at 1,500×g for 4 min at room temperature to obtain approximately 60 µl of filtrate. The concentration of unbound [$^3$H]CLC in the filtrates was determined using a EcoLite™(+) liquid scintillator from ICN Pharmaceuticals Inc. (Costa Mesa, Calif.). Specific bound [$^3$H]CLC concentrations were determined by adding an excess (×100) of unlabeled CLC to the reaction mixture.

For the competition assay, bovine brain tubulin (0.2 mg/ml) was incubated in the microtubule assembly buffer with 0.5 µM [$^3$H]CLC and various concentrations of competitors for 20 min at 37° C. [$^3$H]CLC binding was measured as described above. DMSO was used as a co-solvent at a concentration that did not affect drug binding to tubulin (final 2% v/v). Measurement of [$^3$H]VLB binding was followed by the DEAE-cellulose filter method of Borisy, G. G., Anal. Biochem. (1972) 373–85, and the competition assay was carried out as described for CLC.

I. Inhibitory Effects of (−)-PLH on Proliferation and Mitosis of A549 Cells. The effects of (−)-PLH on the proliferation and mitosis of A549 cells was examined. (−)-PLH inhibited the proliferation of A549 cells in a dose-dependent manner with a 50% inhibitory concentration ($IC_{50}$) value of 0.3 μM, indicating that (−)-PLH was 5-fold less potent than CLC under the assay conditions. However, the mitotic index increased, which correlated with decreased cell proliferation. These results indicated that (−)-PLH arrested the cell cycle during mitosis, which subsequently reduced cell proliferation, similar to the effect observed for other mitotic inhibitors such as CLC and VLB. See Yoshimatsu, K., et al., Cancer Res., (1997), 57, 3208–13. The anti-mitotic effect of (−)-PLH seemed to be reversible, because cells that arrested in M phase by (−)-PLH returned to proliferate again following washing of (−)-PLH and replacement with a fresh medium.

J. Immunofluorescence Staining of Microtubules in A549 Cells. The effects of (−)-PLH on microtubule structure in A549 cells using an anti α-tubulin antibody and a secondary antibody conjugated with FITC were also investigated. It was determined that (−)-PLH inhibited the microtubule assembly like CLC, but did not hyper-stabilize microtubules in a manner similar to that of paclitaxel (Taxol®).

In control cells, a network of cytoskeletal microtubules was clearly visible, and mitotic spindles could be observed in mitotic cells. The addition of (−)-PLH resulted in the disappearance of the microtubule network, and the entire mitotic cell was uniformly stained with α-tubulin antibody, whereas mitotic spindles were never seen. Cells incubated with CLC exhibited a staining profile similar to that of (−)-PLH-treated cells. Paclitaxel, a potent microtubule-stabilizer, produced thick microtubule bundles and multiple bright fluorescent aster formation. See Rowinsky, E. K. et al., J. Natl. Cancer Inst. (1990) 82:1247–59. These results suggested that (−)-PLH inhibited microtubule assembly in A549 cells, but did not stabilize microtubules.

K. (−)-PLH Effects Microtubule Protein Polymerization and Purified Tubulin. The effect of (−)-PLH on the polymerization of microtubule protein obtained from bovine brain were also examined. Accordingly, the time course of the turbidity change in the presence of various concentrations of (−)-PLH and CLC was examined. (−)-PLH inhibited the in vitro polymerization of microtubule protein in a concentration-dependent manner, 80 μM of (−)-PLH completely inhibited the polymerization of microtubule protein, while (+)-PLH did not affect microtubule assembly at concentrations ranging up to a concentration of 200 μM.

It is reported that VLB, see Luduena, R. F.; J. Biol. Chem. (1984) 259:12890–98, or dolastin 10, see Li, Y., et al, Chem. Biol. Interact., (1994), 93, 175–83 increases the turbidity in microtubule protein polymerization at concentrations higher than those required for inhibition. However, (−)-PLH did not increase the turbidity at concentrations up to 200 μM.

To determine whether (−)-PLH acts on tubulin directly or on associated proteins, further tests were performed on the assembly using phosphocellulose-purified tubulin, which was free of microtubule associated proteins. Like microtubule protein, (−)-PLH inhibited tubulin polymerization in a concentration-dependent manner. The $IC_{50}$ value of CLC was 6.6+1.7 μM under the same experimental conditions. These results indicated that (−)-PLH was as effective as CLC in inhibiting tubulin polymerization, and that (−)-PLH acted on tubulin directly rather than on tubulin-associated proteins.

The effect of (−)-PLH on polymerization of the microtubule protein were also studied by electron microscopy. The control sample contained singular microtubules with a normal cylindrical structure, whereas a sample treated with 100 μM (−)-PLH did not contain such structures. These findings confirmed the turbidity measurements and indicated that (−)-PLH inhibited the polymerization of microtubule protein.

L. (−)-PLH Inhibited CLC Binding to Tubulin. To investigate the binding site of (−)-PLH on tubulin, competitive binding studies using [$^3$H]CLC and [$^3$H]VLB were conducted. [$^3$H]CLC and [$^3$H]VLB are antimitotic agents that bind to CLC and VLB binding sites, respectively. [$^3$H]CLC binding was measured by the ultrafiltration method as described above. Under the experimental conditions, the $K_d$ value of CLC to tubulin was $5.3 \times 10^{-7}$M, which is in good agreement with the previously reported value, see Sherline, P., et al., J. Biol. Chem., (1975), 250, 5481–86. (−)-PLH inhibited CLC binding to tubulin in a dose-dependent manner, with an estimated $K_i$ value for CLC binding of $7.4 \times 10^{-6}$M according to a Dixon plot, assuming that (−)-PLH is the competitive inhibitor of CLC binding to tubulin. VLB slightly enhanced CLC binding to tubulin, likely an effect of the stabilization of VLB on the CLC binding activity of tubulin. See Lacey, E. et al., Biochem. Pharmacol. (1987) 36:2133–38. On the other hand, the binding of [$^3$H]VLG was not inhibited by (−)-PLH. CLC enhanced and (−)-PLH slightly enhanced [$^3$H]VLG binding to tubulin. These results suggested that (−)-PLH binds to the CLC binding site (CLC-site) on tubulin or to a site overlapping the CLC-site.

(−)-PLH dose-dependently increased the mitotic index in parallel with inhibition of proliferation of A549 cells, indicating that it prevents cell proliferation by arresting the cell cycle in M phase. Most antimitotic agents such as CLC and VLB are known to exert anti-microtubule activity, including disruption of the process of mitotic spindle formation, resulting in cell arrest in mitosis. (−)-PLH also exhibited an anti-microtubule activity, as evident by depolymerization of cytoskeletal microtubule in A549 cells treated with (−)-PLH. To investigate the mechanism underlying the anti-microtubule activity of this compound, an in vitro polymerization assay using a microtubule protein and phosphocellulose-purified tubulin from bovine brain was performed. (−)-PLH inhibited polymerization of both microtubule protein and purified tubulin, suggesting that (−)-PLH directly acted on tubulin, rather than interacting with microtubule associated proteins. Although (−)-PLH was as effective as CLC in inhibiting the polymerization of purified tubulin, it was 5-fold less potent than CLC in inhibiting the proliferation of A549 cells. These differences may be due to a low permeability of the cell membrane to (−)-PLH compared to CLC. Alternatively, the difference may be due to intracellular transformation of (−)-PLH to an inactive form. The competitive binding assay using radiolabeled CLC and VLB showed that (−)-PLH inhibited the binding of CLC to tubulin, suggesting that (−)-PLH is a competitive inhibitor of CLC binding to tubulin and its binding site may be similar or very close to that of CLC.

As noted above, several natural and synthetic antimitotic agents have been reported to inhibit mitosis by binding to the CLC-site on tubulin. See Iwasaki, S., et al., Med. Res. Rev., (1993), 13, 183–98; Hamel, E., Med. Res. Rev., (1996), 16, 207–31. It seems likely that these CLC-site ligands such as CLC, steganacin, see Kupchan, S. M., et al., J. Am. Chem. Soc., (1973), 95, 1335–1336, podophyllotoxin, see Sackett, D. L., Pharmacol. Ther., (1993), 59, 163–228 and combretastatins (Pettit, G. R., et al., J. Med. Chem., (1995), 38, 1666–1672, interact at two hydrophobic sites on tubulin with biaryl groups located at appropriate distances and angles, whereas curacin A, see Verdier-Pinard, P., et al., Mol. Pharmacol., (1998), 53, 62–76, probably interacts in a different manner. In the case of (−)-PLH, the spatial arrangement of two aryl groups, the phenyl group and imidazole moiety, is probably important for binding to tubulin, because the enantiomer (+)-PLH showed little or no effect on mitosis and tubulin polymerization (data not shown).

Recently, Usui and colleagues, see Usui, T., et al, Biochem, J., (1998), 333, 543–48; Kondoh, M., et al., J. Antibiot, (1998), 51, 801–04, reported that tryprostatin A and its related compounds, which are diketopiperazines consisting of isoprenylated tryptophan and proline, affect the microtubule assembly. They also showed that tryprostatin A inhibited microtubule polymerization by interacting with MAP2/tau-binding site rather than with CLC binding site, at relatively higher concentrations, see Usui, T., et al., Biochem, J., (1998), 333, 543–48; Kondoh, M., et al, J. Antibiot., (1998), 51, 801–04. Although tryprostatin A and (−)-PLH have a similar structural motif, the diketopiperazine ring composed of isoprenylated heterocyclic amino acids, the binding site and effective concentration against microtubule polymerization are different. It is interesting that the two diketopiperazine compounds, which have different constituent amino acids, bind to distinct sites of tubulin molecule and exert a similar biological activity.

EXAMPLE 12

In Vitro Antitumor Activity of PLH Against Human Cancer Cell Lines

For this and the following three examples, EXAMPLES 13, 14 and 15, phenylahistin was prepared as described above in EXAMPLE 1. Agar-cultured medium of *Aspergillus ustus* NSC-F038 was extracted with ethyl acetate, and the extract was purified by silica gel column chromatography twice. PLH was then precipitated in ethyl acetate as a white powder which contained (−) and (+)-PLH. Two separate batches of PLH were used, the (−)-PLH contents of which has been analyzed by chiral HPLC. One contained 24.1% (−)-PLH, which was used for evaluating in vitro antitumor activity and antitumor activity against P388 Leukemia in vivo (Examples 12 and 13), and the other contained 41.7% (−)-PLH, which was used for evaluation of in vivo antitumor activity against Lewis Lung Carcinoma and Colon 26 (Examples 14 and 15).

The antitumor activity of PLH was evaluated by the Human Cancer Cell Line Panel (HCC panel) assay, see Yamori T., *Jap. J Cancer Chemother.*, (1997), 24, 129–35. This HCC panel consists of 38 tumor cell lines including 7 lung cancer, 6 stomach, 6 colon, 5 ovary, 6 central nerve system, 5 breast, 2 kidney and 1 melanoma cell lines. Each tumor cell was seeded in 96-well tissue culture plates and incubated overnight. Various concentrations (5 doses; final $10^{-4}$, $10^{-5}$, $10^{-6}$, $10^{-7}$ and $10^{-8}$ M) of PLH were added, and the cells were incubated for 48 hours. The number of living cells was then measured using the sulforhodamine B assay, see Keepers Y. P., et al., *Eur. J. Cancer*, 27, 897–900 (1991), and the drug concentration that inhibited cell growth by 50% of control cell growth ($GI_{50}$), the drug concentration that inhibited cell growth by 100% of control cell growth (TGI) and the drug concentration that reduced the number of living cells by 50% of the initial cell number ($LC_{50}$) then obtained. All mice were obtained from Japan SLC (Shizuoka, Japan), P388 leukemia cells were obtained from Dainippon Pharmaceuticals Inc. (Osaka, Japan), Lewis Lung Carcinoma from Riken Cell Bank (Tsukuba, Japan), and Colon 26 cells from the National Cancer Center, Japan (Tokyo, Japan).

The results of the HCC panel assay ($GI_{50}$, TGI, and $LC_{50}$ for 38 cell lines) are shown in Table 5. PLH [(−)-PLH content: 24.1%] exhibited anti-proliferative activity against 38 cell lines with $GI_{50}$ values ranging from $2.3 \times 10^{-7}$M to $4.0 \times 10^{-5}$M. The mean graph, see Yamori T., *Jap. J. Cancer Chemother.* (1997) 24, 129–135, of $GI_{50}$ was used for analyzing the mode of action of newly found antitumor agents. The $GI_{50}$ mean graph of PLH revealed that the inhibition profile, showing a relatively wide antitumor spectrum, was similar to that of the vinca alkaloids or paclitaxel, suggesting that the target of the action of PLH may be the microtubule system.

TABLE 5

| Cancer | Cell Line | $GI_{50}$ (M) | TGI (M) | $LC_{50}$ (M) |
|---|---|---|---|---|
| Breast | HBC-4 | $4.6 \times 10^{-7}$ | $>1.0 \times 10^{-4}$ | $>1.0 \times 10^{-4}$ |
| | BSY-1 | $2.3 \times 10^{-7}$ | $6.7 \times 10^{-7}$ | $>1.0 \times 10^{-4}$ |
| | HBC-5 | $6.0 \times 10^{-7}$ | $>1.0 \times 10^{-4}$ | $>1.0 \times 10^{-4}$ |
| | MCF-7 | $4.7 \times 10^{-7}$ | $>1.0 \times 10^{-4}$ | $>1.0 \times 10^{-4}$ |
| | MDA-MB-231 | $6.4 \times 10^{-7}$ | $6.0 \times 10^{-6}$ | $>1.0 \times 10^{-4}$ |
| CNS | U251 | $4.4 \times 10^{-7}$ | $1.0 \times 10^{-5}$ | $>1.0 \times 10^{-4}$ |
| | SF-268 | $4.1 \times 10^{-7}$ | $>1.0 \times 10^{-4}$ | $>1.0 \times 10^{-4}$ |
| | SF-295 | $3.2 \times 10^{-7}$ | $2.4 \times 10^{-6}$ | $>1.0 \times 10^{-4}$ |
| | SF-539 | $2.3 \times 10^{-7}$ | $6.0 \times 10^{-7}$ | $1.1 \times 10^{-5}$ |
| | SNB-75 | $3.7 \times 10^{-7}$ | $>1.0 \times 10^{-4}$ | $>1.0 \times 10^{-4}$ |
| | SNB-78 | $1.3 \times 10^{-6}$ | $>1.0 \times 10^{-4}$ | $>1.0 \times 10^{-4}$ |
| Colon | HCC2998 | $1.1 \times 10^{-6}$ | $5.3 \times 10^{-6}$ | $>1.0 \times 10^{-4}$ |
| | KM-12 | $3.8 \times 10^{-7}$ | $>1.0 \times 10^{-4}$ | $>1.0 \times 10^{-4}$ |
| | HT-29 | $4.0 \times 10^{-7}$ | $>1.0 \times 10^{-4}$ | $>1.0 \times 10^{-4}$ |
| | WiDr | $2.7 \times 10^{-7}$ | $7.9 \times 10^{-7}$ | $>1.0 \times 10^{-4}$ |
| | HCT-15 | $4.9 \times 10^{-7}$ | $>1.0 \times 10^{-4}$ | $>1.0 \times 10^{-4}$ |
| | HCT-116 | $4.8 \times 10^{-7}$ | $>1.0 \times 10^{-4}$ | $>1.0 \times 10^{-4}$ |
| Lung | NCI-H23 | $9.1 \times 10^{-7}$ | $9.2 \times 10^{-5}$ | $>1.0 \times 10^{-4}$ |
| | NCI-H226 | $4.1 \times 10^{-7}$ | $3.1 \times 10^{-5}$ | $>1.0 \times 10^{-4}$ |
| | NCI-H522 | $2.5 \times 10^{-7}$ | $8.1 \times 10^{-7}$ | $>1.0 \times 10^{-4}$ |
| | NCI-H460 | $4.1 \times 10^{-7}$ | $>1.0 \times 10^{-4}$ | $>1.0 \times 10^{-4}$ |
| | A549 | $9.7 \times 10^{-7}$ | $>1.0 \times 10^{-4}$ | $>1.0 \times 10^{-4}$ |
| | DMS273 | $2.9 \times 10^{-7}$ | $>1.0 \times 10^{-4}$ | $>1.0 \times 10^{-4}$ |
| | DMS114 | $3.3 \times 10^{-7}$ | $2.4 \times 10^{-6}$ | $>1.0 \times 10^{-4}$ |
| Melanoma | LOX-IMVI | $1.3 \times 10^{-6}$ | $>1.0 \times 10^{-4}$ | $>1.0 \times 10^{-4}$ |
| Ovary | OVCAR-3 | $30. \times 10^{-7}$ | $>1.0 \times 10^{-4}$ | $>1.0 \times 10^{-4}$ |
| | OVCAR-4 | $4.0 \times 10^{-5}$ | $>1.0 \times 10^{-4}$ | $>1.0 \times 10^{-4}$ |
| | OVCAR-5 | $1.2 \times 10^{-6}$ | $>1.0 \times 10^{-4}$ | $>1.0 \times 10^{-4}$ |
| | OVCAR-8 | $5.2 \times 10^{-7}$ | $5.6 \times 10^{-5}$ | $>1.0 \times 10^{-4}$ |
| | SK-OV-3 | $3.7 \times 10^{-7}$ | $>1.0 \times 10^{-4}$ | $>1.0 \times 10^{-4}$ |
| Renal | RXF-6311 | $1.9 \times 10^{-6}$ | $>1.0 \times 10^{-4}$ | $>1.0 \times 10^{-4}$ |
| | ACHN | $2.8 \times 10^{-5}$ | $>1.0 \times 10^{-4}$ | $>1.0 \times 10^{-4}$ |
| Stomach | St-4 | $4.0 \times 10^{-5}$ | $>1.0 \times 10^{-4}$ | $>1.0 \times 10^{-4}$ |
| | MKN1 | $4.0 \times 10^{-7}$ | $2.1 \times 10^{-5}$ | $>1.0 \times 10^{-4}$ |
| | MKN7 | $3.9 \times 10^{-7}$ | $>1.0 \times 10^{-4}$ | $>1.0 \times 10^{-4}$ |
| | MKN28 | $4.2 \times 10^{-7}$ | $>1.0 \times 10^{-4}$ | $>1.0 \times 10^{-4}$ |
| | MKN45 | $1.5 \times 10^{-6}$ | $>1.0 \times 10^{-4}$ | $>1.0 \times 10^{-4}$ |
| | MKN74 | $4.8 \times 10^{-7}$ | $>1.0 \times 10^{-4}$ | $>1.0 \times 10^{-4}$ |

The TGI values were relatively high, i.e., even at 100 μM PLH, and proliferation of 25 of the 38 cell lines was not completely suppressed. PLH did not exhibit intrinsic cytotoxicity under these experimental conditions, and significant $LC_{50}$ values were not obtained except for SF-539 cells.

EXAMPLE 13

In Vivo Antitumor Activity against P388 Leukemia of Phenylahistin (PLH)

Male CDF1 mice (4 weeks old) were inoculated intraperitoneally with P388 leukemia cells ($1 \times 10^6$ cells/body) on day 0. PLH [(−)-PLH content; 24%] was suspended in 10% ethanol-saline, and administered daily at a dose of 4.2 mg/kg, 12.5 mg/kg, 42 mg/kg or 125 mg/kg intraperitoneally, as a single injection (0.2 ml/body), from days 1 to 12. Each group consisted of six mice. A T/C (%) was calculated according to the following formula:

T/C (%)=[(mean number of survival days of treated group)/(mean number of survival days of control group)]×100

The antitumor activity of PLH [(−)-PLH content: 24.1%] in mice inoculated intraperitoneally with murine P388 leukemia is shown in Table 6. PLH showed significant antitumor activity with a T/C of 129% and 151% at a daily dosage of 41.5 (the calculated dose of (−)-PLH) and 124 (30) mg/kg respectively, for 12 days. The increases in body weight seen in the control group were also suppressed by daily administrations of PLH 41.5 and 124 mg/kg.

TABLE 6

Antitumor Activity of PLH against P388 Leukemia

|  | Control | 4.2 mg/kg (1 mg/kg)# | 12.5 mg/kg (3 mg/kg)# | 42 mg/kg (10 mg/kg)# | 125 mg/kg (30 mg/kg)# |
|---|---|---|---|---|---|
| Mean Body weight on day 12 (g) | 25.2 ± 0.6 | 25.3 ± 0.4 | 24.1 ± 0.6 | 23.0 ± 0.5 | 22.3 ± 0.3 |
| Mean Number of Survival days | 12.5 ± 0.4 | 14.6 ± 0.6* | 14.6 ± 0.5** | 16.1 ± 0.8** | 18.9 ± 0.9** |
| T/C (%) | 100 | 117 | 117 | 129 | 151 |

Calculated dose of (−)-PLH.
*p < 0.05,
**p < 0.01, Mann-Whitney U-Test

Many fungal diketopiperadine metabolites isolated as micotoxins, for example, fumitremorgin B, a diketopiperazine metabolite consisting of proline and isoprenylated tryptophane and identified as cell cycle inhibitors, exert tremorgenic activity when administered to mice. In spite of the structural and biological similarities between PLH and fumitremorgin B, PLH did not induce such side effects, even at the highest dose (124 mg/kg/day). This indicates that the difference of constituents in diketopiperazines may be responsible for the distinct pharmacological effect of PLH. Also, PLH seems not to be long-acting in vivo, as a single administration of PLH (415 mg/kg PLH [(−)-PLH 100 mg/kg]) was not particularly effective (T/C=115%).

EXAMPLE 14

In Vivo Antitumor Activity Against Lewis Lung Carcinoma

Male BDF1 mice (6 weeks old) were inoculated subcutaneously in the right flank region with Lewis Lung Carcinoma cells (1×10⁵ cells/body) on day 0. PLH [(−)-PLH content; 41.7%] was suspended in 10% ethanol-saline, and was administered daily at a dose of 24 mg/kg, 72 mg/kg, or 240 mg/kg intraperitoneally, as a single injection (0.2 ml/body), from days 1 to 14. Each group consisted of six mice. Mice were weighed, and the length (L) and the width (W) of the tumor were measured three times a week. On day 15, mice were sacrificed, and the tumor was excised and weighed. The estimated tumor weight (ETW) was calculated according to the following formula:

$$ETW \text{ (mg)} = L \text{ (mm)} \times W^2 \text{ (mm}^2\text{)}/2,$$

where L represents the length of the tumor and W represents the width of the tumor. The suppression rate was calculated according to the following formula:

$$\text{Suppression rate (\%)} = [1-(TWt/TWc)] \times 100,$$

where TWt represents the mean tumor weight of the treated group and TWc indicates that of the control group. Average and standard errors were calculated for each group. Variance analysis was performed by the Bartlett method (significance level: 5%), and if the variance was uniform, a Dunnett's multiple comparison test was performed. However, if the variance was not uniform, rank conversion was performed followed by variance analysis again by the Bartlett method (significance level: 5%). Significance was established at the p<0.05 level. Based on the weight of the excised tumors in the control group, the suppression rate was calculated for each group, and the $ED_{50}$ and 95% confidence limit were then determined by linear regression analysis.

None of the control and 24 mg/kg/day group mice died. In the 72 mg/kg/day group, 1 mouse died on day 11, and in the 240 mg/kg/day group, 1 mouse died on day 13.

In the control group, body weight changed very little during drug administration. Similarly, little change in body weight was observed in the 24 and 72 mg/kg/day groups. However, in the 240 mg/kg/day group, the body weight was markedly lower than control values after day 3, and significantly lower on day 6.

In the control group, the estimated tumor weight (ETW) was 105 mg on day 7, and gradually increased to 2,306 mg on day 15. The ETW was slightly lower in the 24 mg/kg/day group, in which it increased from 86 mg on day 7 to 2,244 mg on day 15. Similarly, the ETW was slightly lower in the 72 mg/kg/day group, in which it increased from 34 mg on day 7 to 2,142 mg on day 15. In the 240 mg/kg/day group, the ETW was the lowest, increasing from 34 mg on day 7 to 617 mg on day 15. Significant suppression of the ETW was observed on days 10, 13 and 15 (81.8, 82.3 and 73.2%, respectively).

The weight of the excised tumor on the fifteenth day was 3,264 mg for the control group, and 2,941 and 2,380 mg for 24 and 72 mg/kg/day groups, respectively, indicating a rate of suppression of 9.9% and 27.1%, respectively. In the 240 mg/kg/day group, the excised tumor weight was 619 mg, indicating a rate of suppression of 81.0%. The $ED_{50}$ and 95% confidence limit was 105.3 mg/kg/day [calculated dose of (−)-PLH: 43.9 mg/kg/day] and 22.0~504.1 mg/kg/day [(−)-PLHL: 9.2~210.2 mg/kg/day], respectively.

EXAMPLE 15

In Vivo Antitumor Activity Against Colon 26

Male CDFI mice (6 weeks old) were inoculated subcutaneously in the right flank region with Colon 26 cells ($1\times10^5$ cells/body) on day 0. Each group consisted of six mice. Preparation and administration of PLH, and the evaluation of antitumor activity was carried out as described for Lewis Lung Carcinoma, in EXAMPLE 14.

The antitumor activity of PLH ((−)-PLH content: 41.7%) in mice subcutaneously inoculated Colon 26 cells was determined. No mice died during the experimental period in the control, 24 mg/kg/day and 72 mg/kg/day groups. However, in the 240 mg/kg/day group, one mouse died on day 12, two died on day 13 and one died on day 14. No marked changes in the weight of the control was observed, 24 mg/kg/day and 72 mg/kg/day groups, whereas, in the 240 mg/kg/day group, the body weight was lower than that of the control group from day 3, and was lower from day 3 to day 10.

In the control group, the ETW gradually increased from 51 mg on day 7 to 1067 mg on day 15. In the 24 mg/kg/day and 72 mg/kg/day groups, the ETWs increased but the increments were slightly lower than those of the control group. In the 240 mg/kg/day group, the increments of ETW were significantly lower at 14 mg on day 7 and 254 mg on day 15. The suppression rates were 64.4% on day 10, 78.8% on day 13 and 85.4% on day 15.

The weight of the excised tumor on the fifteenth day was 1,159 mg for the control group, and 1,113 and 843 mg for 24 and 72 mg/kg./day groups, respectively, indicating a rate of suppression of 4.0% and 27.3%, respectively. In the 240 mg/kg/day group, the excised tumor weight was 211 mg, indicating a rate of suppression of 81.8%. The $ED_{50}$ and 95% confidence limit was 107.3 mg/kg/day [calculated dose of (−)-PLH: 44.7 mg/kg/day] and 29.0~397.7 mg/kg/day [(−)-PLH: 12.1~165.8 mg/kg/day], respectively.

The in vitro antitumor activity of a scalemic mixture of (−)-PLH and (+)-PLH using HCC panel assay consisting of 38 human cell lines and in vivo antitumor activity using P388 Leukemia, Lewis Lung Carcinoma, and Colon 26 cells were also analyzed in light of the data illustrating that (−)-PLH exhibits anti-proliferative activity against P388 cells with an $IC_{50}$ value of $3.5\times10^{-7}$ M and completely inhibits the cell cycle progression of P388 cells in G2/M phase at $1\times10^{-6}$ M, while (+)-PLH exhibited little or no effect on proliferation or cell cycle progression even at higher concentrations. See EXAMPLES 3, 4, 5, and 12, 13, 14. It was concluded that the antitumor activity of PLH was due to the active S-configuration enantiomer, (−)-PLH.

EXAMPLE 16

Activity of (+)- and (−)-PHL Against Human Cancer Cell Lines

In order to examine detailed biological activity, especially antitumor activity of both (+)- and (−)-phenylahistin, resolution of (+)- and (−)-phenylahistin using chiral HPLC was conducted. By repeating chiral separation twice or three times, each enantiomer with an optical purity over 99.8% was obtained, and each enantiomer was recrystallizes from ethanol-hexane mixture. Antitumor activity of each enanriomer is summarized in Table 7.

TABLE 7

Antiproliferative activities of (−)-PLH and (+)-PLH

| | $IC_{50}$ (M) | |
|---|---|---|
| Cell Line (position) | (−)-phenylahistin | (+)-phenylahistin |
| A-431 (damal) | $2.2\times10^{-7}$ | $2.0\times10^{-5}$ |
| A549 (lung) | $3.0\times10^{-7}$ | $3.0\times10^{-5}$ |
| Hela (ovary) | $2.0\times10^{-7}$ | $1.0\times10^{-5}$ |
| MCF7 (breast) | $3.3\times10^{-7}$ | $1.1\times10^{-5}$ |
| TE-671 (CNS) | $3.7\times10^{-6}$ | $1.3\times10^{-4}$ |
| WiDr (colon) | $1.8\times10^{-7}$ | $8.5\times10^{-6}$ |
| K562 (leukemia) | $1.9\times10^{-7}$ | $1.0\times10^{-5}$ |

*$IC_{50}$ values were determined by MTT assay.

Antitumor activity of (+)- and (−)-phenylahistin was examined against seven human cancer cell lines including A431, WiDr, TE-671, Hela, MCF7, A-549 and K562 cells. The $IC_{50}$ values of each enantiomer were shown in Table 7. (−)-Phenylahistin exhibited antitumor activity with the $IC_{50}$ values ranging from $1.8\times10^{-7}$ (against WiDr cells) to $3.7\times10^{-5}$ (against TE-671). While (+)-PLH exhibited approximately 33 to 100-fold less activity than (−)-PLH.

EXAMPLE 17

Syntheses and Biological Activity of Phenylahistin Derivatives: Criterion to Distinguish Biologically Active Derivatives from Relatively Less-Active Derivatives To characterize the anti-tumor phenylahistin derivatives of the present invention, the structural factors that are required to exhibit the anti-microtubule activity of these compounds have been determined. These factors serve to distinguish active derivatives of the invention from relatively less-active compounds.

In this and the following example, X-ray crystallographic analyses of phenylahistin, the synthesis and physical characterization of various phenylahistin derivatives, and analyses of the structural factors necessary for anti-microtubule activity were conducted. These analyses, which were focused on the structure of unique isoprenylated dehydrohistidine, indicate that this isoprenylated dehydrohistidine forms a rigid planar pseudo three-ring structure, composed of the diketopiperazine and imidazole rings through a hydrogen bond between N8-H and N3 and α,β-unsaturated bond (C6–C7). It is concluded that this structural feature is important for the activity of the anti-tumor activity of the compounds of the present invention.

The derivatives analyzed in this and the following example were prepared in the following manner. As shown in FIG. 3 (Reaction Scheme 3), simple alkylation and reduction of phenylahistin (labeled "11" in FIG. 3) and the modification of cyclo(Gly-Phe) with imidazole derivatives were useful to synthesized the derivatives of phenylahistin for analyzing the structural factors. Derivatives 12–15 were synthesized from phenylahistin by alkylation or reduction. As shown in FIG. 3, Reaction Scheme 2, compounds 12 and 13 were synthesized by hydrogenation of each enantiomer of phenylahistin over 10% palladium on carbon in MeOH under atmospheric hydrogen at room temperature. Two (2) hours of hydrogenation yielded derivative 12, in which the 1,1-dimethyl-2-propenyl group of phenylahistin was reduced, and further hydrogenation (24 h) of compound 12 yielded compound 13, in which the dehydrohistidine part was reduced. In this second reduction, only one diastereomer, which has the same polarity in optical rotation as that of compound 12, was obtained. The diastereoselective hydrogenation of compound 13 may be due to the steric hindrance of the phenyl ring of the Phe residue.

Figure 4:
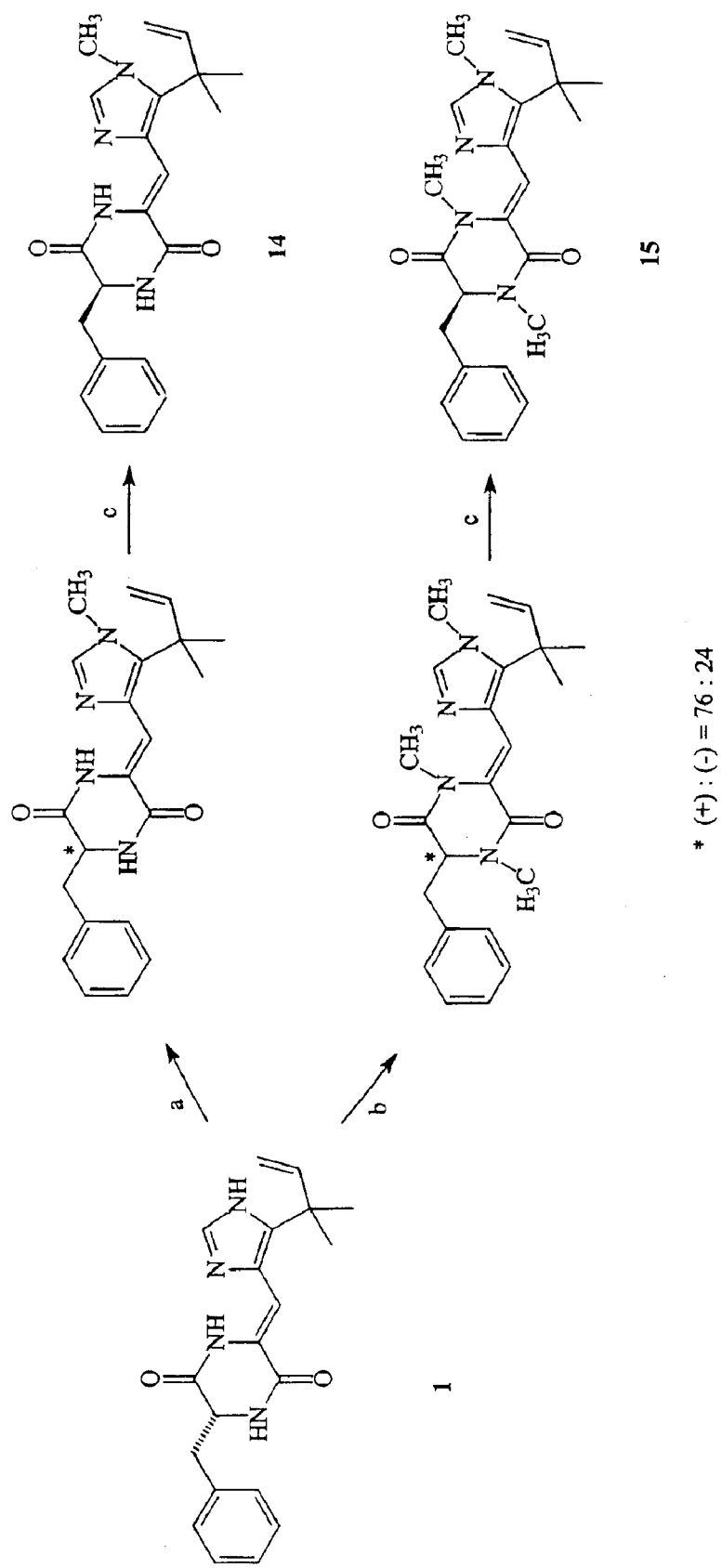
FIG. 4 illustrates Reaction Scheme 4, which shows the preparation of two N-methylated derivatives of (−)-phenylahistin.

As shown in FIG. 4, Reaction Scheme 4, methylation of phenylahistin (labeled "1" in FIG. 4) with MeI and NaH in DMF gave mono- and tri-methylated compounds. The extent of the methylation could be controlled by reaction temperature rather than amounts of the reagents. Monomethylated derivative 14 at the τ nitrogen of the imidazole ring, whose methylation site was detected by NMR analysis (note that the low filed shift of 8(N)-H ($\delta$ 12.20 ppm) in the $^1$H NMR spectrum was maintained in compound 14) and was predominantly obtained with equivalent of the reagents at $-30°$ C., and a tri-methylated derivative 15 was obtained in the reaction with 30 equivalents of the reagents at room temperature. Compound 14 and 15 with the L-phenylalanine residue were separated by HPLC with a chiral column.

Figure 5:
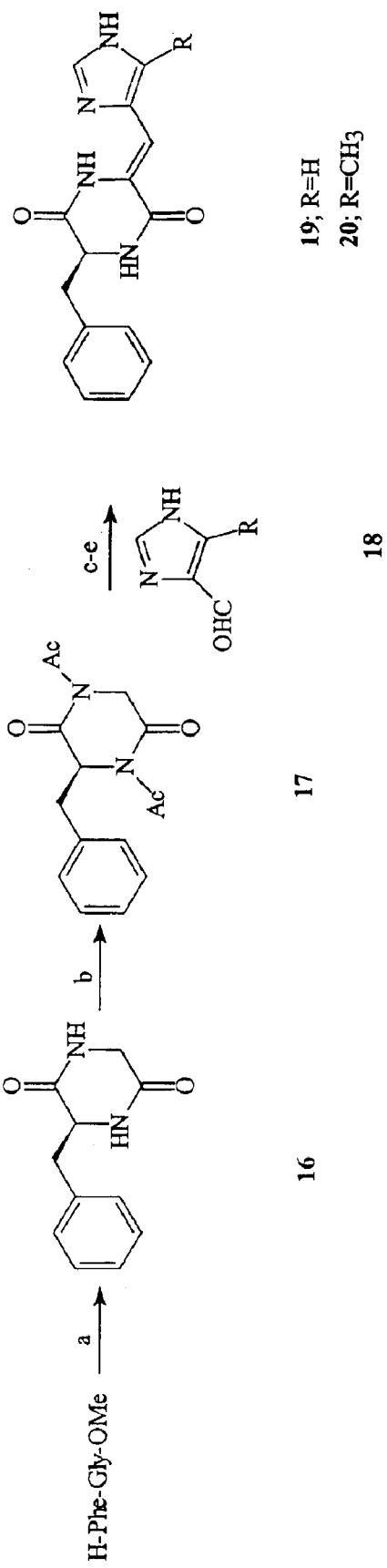
FIG. 5 illustrates Reaction Scheme 5, which shows the preparation of two derivatives of (−)-phenylahistin, compounds identified as 19 and 20, which is the (−)-enantiomer of compound 9 of FIG. 2.
Figure 6:
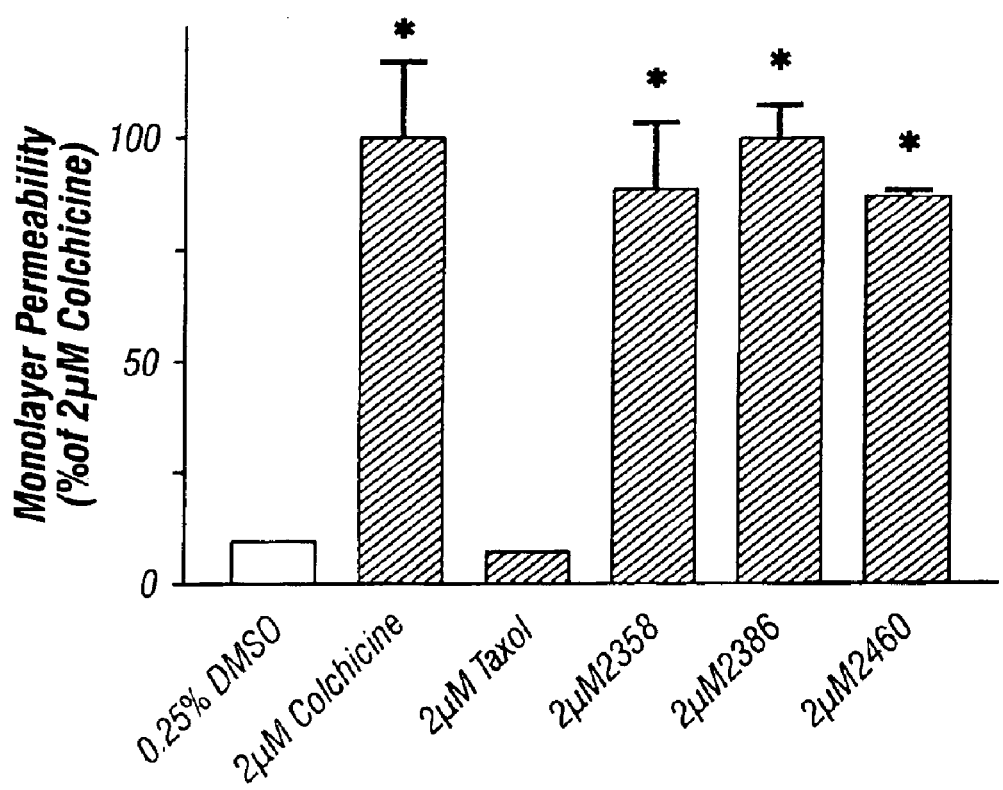
FIG. 6 depicts the effect of t-butyl-phenylahistin in comparison to colchicine and taxol on HuVEC monolayer permeability to FITC-Dextran.
Figure 7:
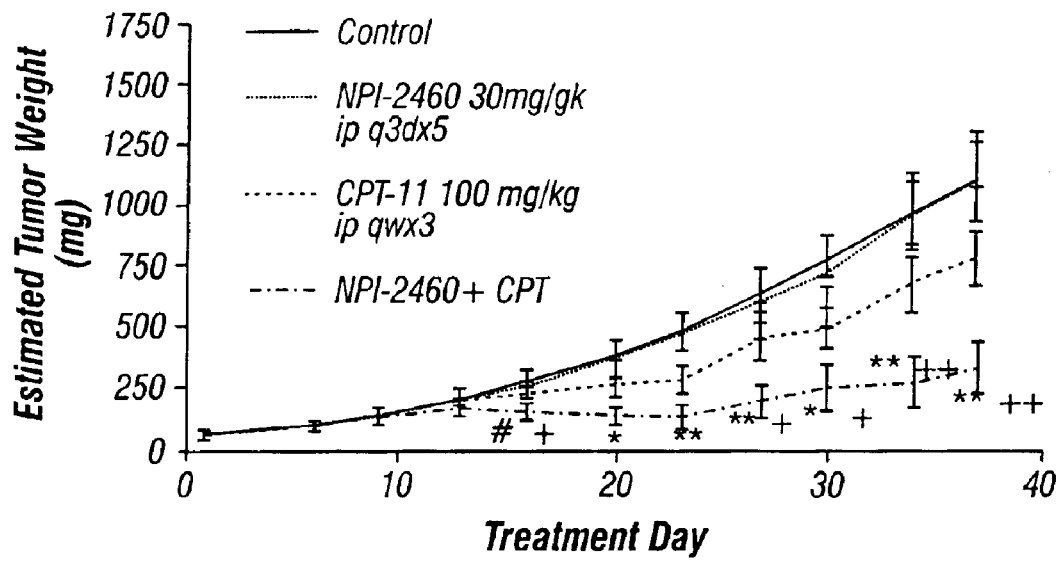
FIG. 7 depicts the effects of t-butyl-phenylahistin alone and in combination with CPT-11 on estimated tumor growth in the HT-29 human colon tumor xenograft model.
Figure 8:
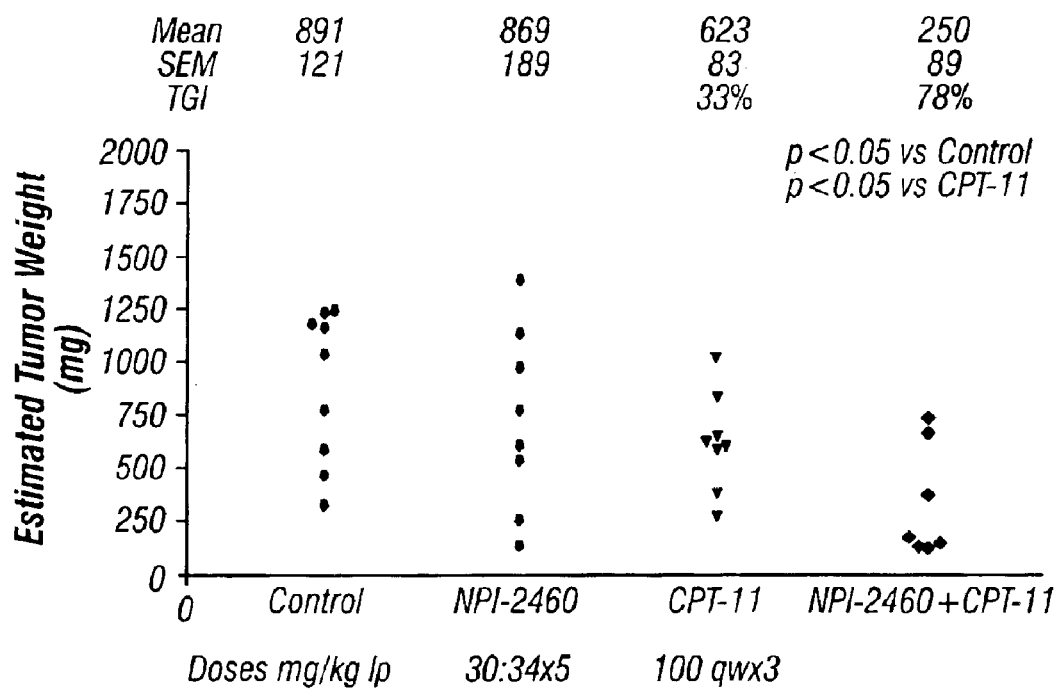
FIG. 8 depicts the effects of t-butyl-phenylahistin alone and in combination with CPT-11 on the weight of tumors excised at autopsy in individual mice in the HT-29 Human Colon Tumor Xenograft model.

As shown in FIG. 5, Reaction Scheme 5, compounds 19 and 20 were synthesized from cyclo(Gly-Phe), compound 16, that was prepared by cyclization of H-Phe-Gly-OMe. After acetylation of the two amide nitrogens of the diketopiperazine ring in 16, 4(5)-imidazolecarboxaldehyde or 4-methyl-5-imidazolecarboxaldehyde (18) was introduced in the presence of lithium diisopropylamide (LDA) and hexamethylphosphoramide (HMPA), according to the method of Bond, R., et al. *Synthetic Commun.*, 19, 2551 (1989), and subsequent dehydration with triflic anhydride-pyridine and deacetylation with aqueous $NH_4OH$ gave compounds 19 and 20, although less than 20% of racemization was observed in these steps.

According to X-ray crystallographic analyses of (+)-phenylahistin, as provided in Table 8, the stereochemistry of C6–C7 double bond was confirmed to be Z, and the existence of a hydrogen bond between N8-H and N3 was observed. This result was in good agreement with the observation in the NMR studies (low field-shift of N8-H ($\delta$ 12.08 ppm). These findings suggested that two heterocycles, i.e., the diketopiperazine and imidazole rings, were fixed in the same plane by forming a pseudo three-ring structure. The benzyl group of the Phe residue was stacked over the diketopiperazine ring by sticking out from this plane, whose conformation is reported as the energetically most favored one in diketopiperazine with an aromatic amino acid residue, according to the method of Liwo, A. et al. *Tetrahedron Lett.*, 26, 1873 (1985). The 1,1-dimethyl-2-propenyl group at the imidazole ring was also restricted its movement by the steric hindrance of a hydrogen atom at the β-position (C6) of the α,β-unsaturated His derivative. Therefore, it is indicated that the conformation of (+)-phenylahistin is highly restricted. Since the (−)-form of 11, i.e., the biologically active enantiomer, also takes the same conformational feature as that of its (+)-form only with the opposite configuration at the α-position of the Phe residue, this rigid conformation of phenylahistin may be important for the binding to the microtubule protein.

TABLE 8

Data of the x-ray crystallographic analysis of (+)-phenylahistin

| Crystal parameters | — |
|---|---|
| Empirical formula | $C_{20}H_{22}N_4O_2$ |
| Formula weight | 350.42 |
| Crystal system | tetragonal |
| Lattice parameters: | a = 15.3509(7) Å |
| | c = 8.309(2) Å |
| | V = 1958.0(2) Å$^3$ |
| | Z = 4 |
| Space group | $P4_2$ (#77) |
| Dcalc. | 1.189 g/cm$^3$ |
| μ (CuKα) | 6.37 cm$^{-1}$ |
| Refinement parameters | — |

TABLE 8-continued

Data of the x-ray crystallographic analysis of (+)-phenylahistin

| Reflections measured | 2229 |
|---|---|
| Nonzero reflections | 1724 |
| R-indexResiduals: R$^a$ | 0.057 |
| Residuals: RW$^b$ | 0.067 |
| Goodness of fit indicator$^c$ | 4.31 |

[a] $\Sigma ||Fo| - |Fc||\Sigma|Fo|$
[b] $[\Sigma w ((|Fo| - |Fc|)^2/\Sigma wFo^2)]^{1/2}$
[c] $[(\Sigma w (|Fo| - |Fc|)^2/(No - Nv)]^{1/2}$ To study the relationship between the rigid plane structure of (−)-phenylahistin and that compound's biological activity, the derivatives of (−)-phenylahistin were synthesized and the anti-microtubule effect on the polymerization of microtubule protein prepared from bovine brain and the anti-proliferative effect on P388 cells were studied, as described in prior examples. As described above, (−)-phenylahistin exhibits the colchicine-like inhibition of microtubule polymerization ($IC_{50}$=25 μM). This inhibitory activity of (−)-phenylahistin was almost the same as that of colchicine ($IC_{50}$=16 μM), although the anti-proliferative activity of (−)-phenylahistin ($IC_{50}$=0.21 μM) was about 10 times less active than that of colchicine ($IC_{50}$=0.031 μM). The difference of these activities is due either to the unaccounted-for biological activities of colchicine or to lower cellular permeability of (−)-phenylahistin in anti-proliferative assay, since (−)-phenylahistin has more hydrophilic structure than colchicine. Furthermore, as described above, (−)-phenylahistin with the L-Phe residue was 50 times more active than (+)-phenylahistin in anti-proliferative assays. (+)-Phenylahistin also exhibited relatively weak inhibitory activity against microtubule polymerization (15% inhibition at 200 μM) compared with (−)-phenylahistin. Thus, the orientation of the benzyl group of the phenylalanine residue is important to the biological activity of the compounds of the present invention.

As shown in Table 9, compound 12, in which the 1,1-dimethyl-2-propenyl group of phenylahistin was reduced, showed the same activity as phenylahistin, indicating that this double bond is not important for the anti-microtubule activity. However, compound (−)-13, in which the dehydrohistidine of (−)-12 was reduced, completely lost the inhibitory activity. Since this modification disrupts the substantially planar characteristic of the pseudo three-ring structure in the same plane as the phenylahistin backbone, this result suggests that, for the inhibitory activity, it is important that the two rings, i.e., diketopiperazine and imidazole rings, are fixed in the same plane.

TABLE 9

Biological activity of phenylahistin, its derivatives, and selected structurally-related compounds.

| | $IC_{50}$ (μM) | |
|---|---|---|
| compound | Microtubule Protein$^a$ polymerization | P388 proliferation |
| (−)-11 | 25 | 0.21 (±0.02)$^b$ |
| (+)-11 | >200 [15%]$^c$ | 10 (±1.5) |
| (−)-12 | 30 | 0.23 (±0.05) |
| (+)-12 | >200 [12%] | 19 (±4.2) |
| (−)-13 | >200 | >200 |
| (+)-13 | >200 | >200 |
| 14 | 100 | 0.95 (±0.03) |
| 15 | >200 | 160 (±5.5) |
| 19 | >200 [11%] | >200 |
| 20 | >200 {9%] | 15 (±4.5) |

TABLE 9-continued

Biological activity of phenylahistin, its derivatives, and selected structurally-related compounds.

| compound | IC$_{50}$ (µM) | |
|---|---|---|
| | Microtubule Protein[a] polymerization | P388 proliferation |
| Cyclo(His-Phe)[d] | >200 | >200 |
| colchicine[d] | 16 | 0.031 (±0.01) |

[a]Microtubule protein was prepared from bovine brain by two cycle of assembly and disassembly method. The concentration of microtubule protein used for the assay was 1.5 mg/mL.
[b]Values are means (±SEM) of three experiments.
[c]The inhibition percentage at 200 µM was indicated in the parenthesis when the inhibition was observed, since the diketopiperazine derivatives are insoluble in the concentration more than 200 µM.
19 and 20 were chiral-purified.
[d]Cyclo(His-Phe) and colchicine are each commercially available; each was purchased from Sigma.

In further syntheses, the nitrogen atoms of phenylahistin were modified by methylation. Compound 14, in which the τ nitrogen of the imidazole ring of (−)-phenylahistin was methylated, was about 5 times less active than (−)-phenylahistin, suggesting this imidazole nitrogen probably participates in the binding with the microtubule protein or this methylation affords the structural hindrance to the conformation of the 1,1-dimethyl-2-propenyl group on the imidazole ring. Tri-methylated compound 15 almost lost the inhibitory activity. This result also suggests that the rigid plane conformation of (−)-phenylahistin is important to the anti-microtubule activity, since the methylation of a diketopiperazine nitrogen (N8) disrupts the formation of hydrogen bond on N8-H necessary for the rigid pseudo three-ring conformation.

The importance of an alkyl group at the 5-position on the imidazole ring to the biological activity of the compounds of the present invention was analyzed via the following analyses of compounds 19 and 20, which were also synthesized from cyclo(Phe-Gly), compound 16. In compounds 19 and 20, the 1,1-dimethyl-2-propenyl group of (−)-phenylahistin was replaced with a hydrogen atom or a methyl group, respectively. Compound 19, in which the 1,1-dimethyl-2-propenyl group was replaced with the hydrogen atom at this position, showed no inhibitory activity. Compound 20, in which the 1,1-dimethyl-2-propenyl group was replaced with a methyl group at this position, also showed no activity in the anti-microtubule assay, although weak inhibition on P388 cell proliferation was observed. This drastic decreased in biological activity in 19 indicates that an alkyl group with a proper length or a quaternary carbon at the 5-position of the imidazole ring is important for the activity.

Accordingly, the results of the x-ray crystallographic analysis and the biological evaluation of the phenylahistin derivatives elucidate a structural factor of phenylahistin necessary for its anti-microtubule activity. This factor is that the rigid and planar pseudo three-ring structure formed by a hydrogen bond are important for the biological activity of (−)-phenylahistin.

For this example, the microtubule protein polymerization assay was performed as follows. Microtubule protein was prepared from bovine brain tissue by two cycles of assembly and disassembly. Polymerization of microtubule protein was monitored by an increase in turbidity at 37° C. in microtubule assembly buffer containing 100 mM MES, 0.5 mM MgCl$_2$, 1 mM EGTA and 1 mM GTP. The polymerization of microtubule protein was initiated by a temperature shift from 0° C. to 37° C. Turbidity was measured on a thermo-controlled spectrophotometer (Beckman DU-20, Fullerton, Calif.) at 360 nm. Compounds were dissolved in DMSO, which was used in all experiments at a final concentration of 2% (v/v).

For this example, the Alamar Blue™ assay was performed as follows. Exponentially growing P388 cells were seeded into 96-well tissue culture plates (5×10$^3$ cells/100 µl/well) and cultured in RPMI 1640 medium supplemented with 10% fetal bovine serum for 16 h. Compounds (DMSO solution) were then added to each well at various concentrations, and the cells were cultured for an additional 48 h. Living cells were counted using Alamar Blue™ (BioSource International, Camarillo, Calif.), according to the method of Ahmed, S. A. et al., *J. Immunol. Methods,* 170, 211 (1994).

For this example, the Single-Crystal X-ray Diffraction Analysis was performed as follows. A pale yellow crystal of (+)-phenylahistin having approximately dimension 0.4×0.4×0.3 mm, which was crystallized from EtOAc, was used for single-crystal x-ray diffraction analysis. All x-ray measurements were made on a Rigaku AFC7R diffractometer with graphite monochromated Cukα radiation and a rotating anode generator. The crystal data and refinement parameters were summarized in Table 8. Of the 2229 reflections which were collected, 2064 were unique (Rint=0.019). The data were corrected for Lorentz and polarization effects. A correction for secondary extinction was applied. The structure was solved by direct methods and expanded using standard Fourier techniques. All calculations were performed using the teXscan crystallographic software package of Molecular Structure Corporation.

EXAMPLE 18

Syntheses and Physical Characterization of Phenylahistin Derivatives

The melting points of the phenylahistin derivatives described in the previous example were determined on a Mettler FP62 apparatus and are uncorrected. $^1$H-NMR and $^{13}$C-NMR spectra were recorded on JEOL GSX27OJ spectrometer. The spectra were recorded with tetramethylsilane (δ=0.0 for $^1$H); DMSO-d$_6$ (δ=39.5 for $^{13}$C); CDCl$_3$ (δ=77.0 for $^{13}$C) as internal reference. Mass spectra (electrospray ionization, methanol as the mobile phase) were analyzed with Finnigan SSQ 7000 spectrometer. High-resolution fast atom bombardment mass spectra were analyzed with JEOL JMS-DX303 spectrometer. Infrared spectra were recorded on a JEOL JIR-5500 infrared spectrophotometer in KBr pellets. A silica-gel column chromatography was performed using Merck 70-230 mesh silica gel 60. Optical rotations were measured on a Horiba SEPA-200 polarimeter, and are given in units of 10$^{-1}$ deg cm$^2$ g$^{-1}$. Elemental analyses were performed by Fisons EA 1108 elemental analyzer.

The precise synthetic routes and physical characteristics of the phenylahistin derivatives described in the previous example are as follows.

(−)-Cyclo-[5-(1,1-dimethylpropyl)dehydrohistidinyl-L-phenylalanine] (−)-12: To a solution of (−)-phenylahistin (30 mg, 0.086 mmol) in MeOH (10 mL) was added 10 mg of 10% palladium on carbon and the mixture was stirred at room temperature for 2 h under hydrogen at atmospheric pressure. After the catalyst was filtered off and the filtrate was concentrated under reduced pressure, the residue was purified by column chromatography on silica (5 g) using CHCl$_3$-MeOH (50:1) as an eluent. Desired fractions were collected and the solvent was evaporated. The residual white powder was recrystallized from EtOH-hexane to give 12 mg (39% of (−)-12 as a colorless solid: mp 224–226° C.; $[\alpha]_D^{25}$ −295 (c=0.15, MeOH), UV (MeOH) nm 322 (ε 23300), 231 (ε 8830), 203 (ε 16800); IR (KBr) cm$^{-1}$ 3310, 3220, 2970, 1670, 1440; $^1$H NMR (270 MHz, CDCl$_3$) δ 12.09 (br s, 1H), 8.98 (br s. 1H), 7.56 (s, 1H), 7.29–7.38 (m, 5H), 6.87 (s, 1H), 5.67 (s, 1H), 4.34 (ddd, J=2, 3, 10 Hz, 1H), 3.51 (dd, J=3, 14 Hz, 1H), 2.29 (dd, J=10, 14 Hz, 1H), 1.74 (q, J=7 Hz, 2H), 1.40 (s, 6H), 0.74 (t, J=7 Hz 3H); $^{13}$C NMR (67.5 MHz, CDCl$_3$) δ 164.6, 159.9, 138.1, 135.5, 132.2, 132.1, 129.5 (2C), 129.1 (2C), 127.4, 123.6, 105.4, 57.2, 41.3, 36.2, 35.4, 27.9 (2C), 9.2; HRMS m/z 352.1926 (M$^+$) (calcd for C$_{20}$H$_{24}$N$_4$O$_2$: 352.1899). Anal. calcd for C$_{20}$H$_{24}$N$_4$O$_2$: C,68.16; H,6.86; N,15.90. Found: C,68.34, 6.78, 15.82.

(+)-Cyclo-[5-(1,1-dimethylpropyl)dehydrohistidinyl-L-phenylalanine] (+)-12: This compound was prepared according to the same procedure for the preparation of (−)-12. 44% yield from (+)-1; colorless solid; mp 222–223° C.; $[\alpha]_D^{25}$+ 284(c=0.10, MeOH), UV (MeOH) nm 322 (ε 22800), 231 (ε 8720), 203 (ε 16300); IR (KBr) cm$^{-1}$ 3310, 3220, 2970, 1670, 1440; $^1$H NMR (270 MHz, CDCl$_3$) δ 12.09 (br s, 1H), 8.98 (br s. 1H), 7.56 (s, 1H), 7.29–7.38 (m, 5H), 6.87 (s, 1H), 5.67 (s, 1H), 4.34 (ddd, J=2, 3, 10 Hz, 1H), 3.51 (dd, J=3, 14 Hz, 1H), 2.29 (dd, J=10, 14 Hz, 1H), 1.74 (q, J=7 Hz, 2H), 1.40 (s, 6H), 0.74 (t, J=7 Hz 3H); $^{13}$C NMR (67.5 MHz, CDCl$_3$) δ 164.6, 159.9, 138.1, 135.5, 132.2, 132.1, 129.5 (2C), 129.1 (2C), 127.4, 123.6, 105.4, 57.2, 41.3, 36.2, 35.4, 27.9 (2C), 9.2; HRMS m/z 352.1932 (M$^+$) (calcd for C$_{20}$H$_{24}$N$_4$O$_2$: 352.1899). Anal. calcd for C$_{20}$H$_{24}$N$_4$O$_2$: C,68.16; H,6.86; N,15.90. Found: C,68.09, 6.87, 15.84.

(−)-Cyclo-[5-(1,1-dimethylpropyl)histidinyl-L-phenylalanine] (−)-13: This compound was prepared from (−)-12, according to the same procedure for the preparation of (−)-12, with 24 h of reaction time. 60% yield from (−)-12; white powder; mp 224–225° C.; $[\alpha]_D^{25}$−96(c=0.16, MeOH), UV (MeOH) nm 257 (ε 194), 205 (ε 18100), IR (KBr) cm$^{-1}$ 3380, 3200, 2970, 1670, 1440; $^1$H NMR (270 MHz, DMSO-d6) δ 11.55 (br s, 1H), 8.25 (br s. 1H), 7.86 (br s, 1H), 741 (s, 1H), 7.29–7.14 (m, 5H), 4.24 (br s, 1H), 3.94 (br d, J=11 Hz, 1H), 3.11 (dd, J=14, 4 Hz, 1H), 2.88 (dd, J=14,5 Hz, 1H), 2.82 (dd, J=15, 2 Hz, 1H), 1.45 (q, J=7 Hz, 2H), 1.32 (dd, J=15, 11 Hz, 1H), 1.13 (s, 3H), 1.12 (s, 3H), 0.60 (t, J=7 Hz 3H); $^{13}$C NMR (67.5 MHz, CDCl$_3$) δ 166.87, 165.42, 135.93, 132.54, 131.58, 131.23, 130.32 (2C), 127.94 (2C), 126.61, 55.70, 54.31, 38.16, 35.04, 34.31, 31.85, 27.63, 27.57, 9.05; HRMS m/z 354.2098 (M$^+$) (calcd for C$_{20}$H$_{24}$N$_4$O$_2$: 354.2055). Anal. calcd for C$_{20}$H$_{24}$N$_4$O$_2$: ⅓H$_2$O: C,66.64; H,7.46; N,15.54. Found: C,66.75, 7.41, 15.52.

(+)-Cyclo-[5-(1,1-dimethylpropyl)histidinyl-L-phenylalanine] (+)-13: This compound was prepared from (+)-12 according to the same procedure for the preparation of (−)-13. 46% yield from (+)-12; white powder; mp 226–227° C.; $[\alpha]_D^{25}$+99(c=0.10, MeOH), UV (MeOH) nm 257 (ε 174), 205 (ε 18200), IR (KBr) cm$^{-1}$ 3380, 3200, 2970, 1670, 1440; $^1$H NMR (270 MHz, DMSO-d$_6$) δ 11.55 (br s, 1H), 8.25 (br s. 1H), 7.86 (br s, 1H), 7.41 (s, 1H), 7.29–7.14 (m, 5H), 4.24 (br s, 1H), 3.94 (br d, J=11 Hz, 1H), 3.11 (dd, J=14, 4 Hz, 1H), 2.88 (dd, J=14,5 Hz, 1H), 2.82 (dd, J=15, 2 Hz, 1H), 1.45 (q, J=7 Hz, 2H), 1.32 (dd, J=15, 11 Hz, 1H), 1.13 (s, 3H), 1.12 (s, 3H), 0.60 (t, J=7 Hz 3H); $^{13}$C NMR (67.5 MHz, CDCl$_3$) δ 166.87, 165.42, 135.93, 132.54, 131.58, 131.23, 130.32 (2C), 127.94 (2C), 126.61, 55.70, 54.31, 38.16, 35.04, 34.31, 31.85, 27.63, 27.57, 9.05; HRMS m/z 354.2110 (M$^+$) (calcd for C$_{20}$H$_{24}$N$_4$O$_2$: 354.2055). Anal. calcd for C$_{20}$H$_{24}$N$_4$O$_2$: ½H$_2$O: C,66.09; H,7.49; N,15.41. Found: C,65.80, 7.50, 15.30.

(−)-Cyclo-[(N$^{im}$-methyl-5-(1,1-dimethyl-2-propenyl)) dehydrohistidinyl-L-phenylalanine] (−)-14: To a solution of phenylahistin (200 mg, 0.57 mmol) in DMF (15 mL) was added 45 mg (1.88 mmol) of sodium hydride (NaH) (60% in mineral oil) in portions and the mixture was stirred at −30° C. for 10 min. To this mixture, 1.0 mL (17.1 mmol) of MeI was added dropwise and stirred at −30° C. for 2 h. 20 mL of saturated aqueous NH$_4$Cl was added to the reaction mixture and the mixture was extracted three times with 50 mL of EtOAc. The combined organic layers were washed with saturated NaCl, dried over Na$_2$SO$_4$ and concentrated in vacuo. The residual white powder (150 mg) was chromatographed over 20 g of silica gel and eluted with CHCl$_3$-MeOH (50:1) as an eluent to give 130 mg (63%) of 14 as white powder: The (−)-form of 14 was isolated by HPLC using chiral column (CHIRALCEL OD, 10×250 mm) eluted with a mixture of hexane and ethanol (3:1) at a flow rate of 6.0 mL/min on a Waters system (600E series). 19% yield from 1; white powder; mp 214–215° C.; $[\alpha]_D^{25}$−285(c=0.30, MeOH), UV (MeOH) nm 317 (ε 25400), 232 (sh, ε 8640), 204 (ε 16800); IR (KBr) cm$^{-1}$ 3200, 2980, 1680, 1440; $^1$H NMR (270 MHz, CDCl$_3$) δ 12.20 (br s, 1H), 7.39 (s. 1H), 7.38–7.24 (m, 5H), 7.09 (s, 1H), 6.01 (dd, J=18, 9 Hz, 1H), 5.68 (br s, 1H), 5.14 (d, J=9 Hz, 1H), 5.00 (d, J=18 Hz, 1H), 4.33 (m, 1H), 3.66 (s. 3H), 3.50 (dd, J=14, 3 Hz, 1H), 2.92 (dd, J=14, 10 Hz, 1H), 1.59 (s, 6H); $^{13}$C NMR (67.5 MHz, CDCl$_3$) δ 164.6, 160.1, 145.6, 138.5, 136.5, 135.6, 134.6, 129.5 (2C), 129.1 (2C), 127.4, 124.0, 112.7, 106.6, 57.1, 41.3, 39.2, 34.9, 28.9, 28.8; HRMS m/z 364.1909 (M$^+$) (calcd for C$_{21}$H$_{24}$N$_4$O$_2$: 364.1899). Anal. calcd for C$_{21}$H$_{24}$N$_4$O$_2$.¼H$_2$O: C,68.36; H,6.69; N,15.19. Found: C,68.44, H,6.67, N,15.01.

(−)-Cyclo-N,N'-dimethyl-[(N$^{im}$-methyl-5-(1,1-dimethyl-2-propenyl))dehydro-histidinyl-L-phenylalanine] (−)-15: This compound was prepared from phenylahistin with 10 equivalents of NaH and 30 equivalent of MeI at room temperature according to the same procedure for the preparation of (−)-14. For the purification of (−)-15, a mixture of hexane and ethanol (4:1) was used as an eluent in the chiral column HPLC mentioned in the preparation of (−)-14. 8% yield from phenylahistin: white powder; mp 95–98° C.; $[\alpha]_D^{25}$−632(c=0.50, MeOH), UV (MeOH) nm 287 (ε 11100), 203 (ε 15900); IR (KBr) cm$^{-1}$ 2900, 1690, 1640, 1380; $^1$H NMR (270 MHz, CDCl$_3$) δ 8.76 (br s, 1H), 7.33–7.21 (m, 5H), 7.08 (s, 1H), 6.00 (dd, J=18, 11 Hz, 1H), 5.28 (d, J=11 Hz, 1H), 5.08 (d, J=18 Hz, 1H), 4.19 (dd, J=10,4 Hz, 1H), 3.86 (s, 3H), 3.38 (dd, J=14, 4 Hz, 1H), 3.13 (dd, J=14, 10 Hz, 1H), 2.92 (s, 3H), 2.55 (s, 3H), 1.60 (s, 3H), 1.57 (s, 3H); $^{13}$C NMR (67.5 MHz, CDCl$_3$) δ 166.8, 160.2, 143.5, 137.8, 136.5, 134.8, 129.4 (2C), 128.8 (2C), 127.2, 124.6, 114.4, 105.6, 65.9, 40.6, 38.8, 36.6, 34.9, 28.4, 28.1; HRMS m/z 392.2223 (M$^+$) (calcd for C$_{23}$H$_{28}$N$_4$O$_2$: 392.2212). Anal. calcd for C$_{23}$H$_{28}$N$_4$O$_2$: C,70.38; H,7.19; N,14.27. Found: C,70.26, H,7.30, N, 14.27.

Cyclo-[glycinyl-L-phenylalanine] 16: To a solution of H-Phe-Gly-OMe, which was prepared from Boc-Phe-Gly-OMe with 4N HCl-dioxane (20 g, 59 mmol), in MeOH (100 mL) was refluxed for 16 h. The white precipitate occurred during reflux was washed with 10 mL of MeOH for three times and collected to give 7.5 g (62%) of 16 as a white powder, mp 262–263° C. (decomp.); $[\alpha]_D^{25}$+60 (c=0.15, DMSO), UV (MeOH) nm 257 (ε 101), 206 (ε 5770); IR (KBr) cm$^{-1}$3340, 3200, 3060, 1680, 1470, 1340; $^1$H NMR (270 MHz, DMSO-d$_6$) δ 8.16 (br s, 1H), 7.90 (br s. 1H), 7.32–7.15 (m, 5H), 4.07 (br dd, J=7,4 Hz, 1H), 3.35 (dd, J=18, 3 Hz, 1H), 3.10 (dd, J=14, 4 Hz, 1H), 2.88 (dd, J=14, 5 Hz, 1H), 2.75 (d, J=18 Hz, 1H), $^{13}$C NMR (67.5 MHz, DMSO-$d_6$) δ 167.1, 165.5, 136.0, 130.1 (2C), 128.1 (2C), 126.8, 55.5, 43.7, 38.8; MS (ESI) m/z 205 (M+H)$^+$; Anal. calcd for $C_{11}H_{12}N_2O_2$. ⅕$H_2O$: C,63.57; H,6.01; N,13.48. Found: C,63.85, H,5.86, N, 13.40.

Cyclo-N,N'-diacetyl-[glycinyl-L-phenylalanine] 17: The mixture of compound 16 (0.5 g, 2.45 mmol) and fused sodium acetate (201 mg, 2.45 mmol) in acetic anhydride (10 mL) was heated for 16 h at 100° C. under nitrogen. After acetic anhydride was removed in vacuo at 45° C., the residue was solved in EtOAc and the resulted organic layer was washed with saturated NaCl, dried over $Na_2SO_4$ and 17 was crystallized from EtOAc. 88% yield (0.62 g); colorless solid; mp 84–85° C.; $[α]_D^{25}$+7.8 (c=0.52, MeOH); UV (MeOH) nm 209 (ε 20400); IR (KBr) cm$^{-1}$ 1720, 1400, 1380, 1240; $^1$H NMR (270 MHz, $CDCl_3$) δ 7.33–7.26 (m, 3H), 7.08–7.05 (m, 2H), 5.44 (t, J=5 Hz, 1H), 4.49 (d, J=19 Hz, 1H), 3.35 (dd, J=14, 5 Hz, 1H), 3.20 (dd, J=14, 5 Hz, 1H), 2.58 (s, 3H), 2.55 (s, 3H), 2.48 (d, J=19 Hz, 1H); $^{13}$C NMR (67.5 MHz, $CDCl_3$) δ 171.2, 171.0, 167.9, 166.0, 134.3, 129.7 (2C), 129.1 (2C), 128.2, 59.0, 46.0, 38.7, 27.1, 26.8; MS (ESI) m/z 311 (M+Na)$^+$; Anal. calcd for $C_{15}H_{15}N_2O_4$: C,62.49; H,5.59; N,9.72. Found: C,62.50, H,5.50, N,9.67.

Cyclo-[dehydrohistidinyl-L-phenylalanine] 19: To a solution of 17 (311 mg, 0.93 mmol) in dimethoxyethanol (DME) (10 mL) was added 0.6 mL of 2M lithium diisopropylamide (LDA, 1.2 mmol) and the mixture was stirred at −70° C. for 10 min. To this solution was added a solution of 4(5)-formylimidazole (120 mg, 1.25 mmol, Maybridge Chemical Co. Ltd., Cornwall, U.K.) in HMPA (4 mL)-DME (6 mL) at −70° C. This mixed solution was allowed to warm to −30° C. After stirring for 30 min at this temperature, a triflic anhydride (370 μL, 2.2 mmol) and pyridine (180 μL, 2.2 mmol) were added and the solution was allowed to warm to room temperature. After additional stirring for 1 h, aqueous ammonia (3 mL) was added and stirred for 14 h at room temperature. The reaction mixture was extracted with $CHCl_3$ for three times, dried over $Na_2SO_4$ and concentrated in vacuo. The resultant residue was purified by HPLC with a reverse phase column (Waters, μBondasphere 19×150 mm, 10 μm, C-18) employing a gradient from 60 to 80% $CH_3CN$ in 0.1% TFA at a flow rate of 17 mL/min on a Waters system (600E series). However, since purified compound 19 contained 28% of a racemized compound with D-phenylalanine (44% ee), further purification by HPLC with a chiral column was performed using the same procedure described for the purification of (−)14. 8% yield from 7; white powder; mp 208–209° C. $[α]_D^{25}$-257 (c=0.21, DMSO); UV (MeOH) nm 307 (ε 16700); IR (KBr) cm$^{-1}$ 3400, 3120, 1680, 1440; $^1$H NMR (270 MHz, DMSO-$d_6$) δ 12.88 (br s, 1H), 11.09 (br s, 1H), 8.44 (s, 1H), 8.13 (br s, 1H), 7.48 (s, 1H), 7.24–7.11 (m, 5H), 6.25 (s, 1H), 4.48 (m, 1H), 3.19 (dd, J=14, 4 Hz, 1H), 2.95 (dd, J=14, 5 Hz, 1H); $^{13}$C NMR (67.5 MHz, DMSO-$d_6$) δ 164.8, 158.6, 135.8, 135.5, 132.3, 130.0 (2C), 128.0 (2C), 126.7, 125.6, 118.3, 101.8, 55.9, 38.9; (overlapping DMSO-$d_6$); HRMS m/z 282.1084 (M$^+$) (calcd for $C_{15}H_{14}N_4O_2$: 282.1117). Anal. calcd for $C_{15}H_{14}N_4O_2$—$CF_3COOH$: C,51.52; H,3.81; N,14.14, Found: C,51.15, H,3.62, N,13.84.

Cyclo-[(5-methyl)dehydrohistidinyl-L-phenylalanine] 20: This compound was prepared from compound 17 with 4-methyl-5-imidazolecarboxaldehyde according to the same procedure for the preparation of 19. 3% yield from 17; colorless solid; mp 285–286° C. (decomp); $[α]_D^{25}$-267° (c=0.21, DMSO); UV (MeOH) nm 319 (ε 22800); IR (KBr) cm$^{-1}$ 3400, 3180, 1680, 1450; $^1$H NMR (270 MHz, DMSO-$d_6$) δ 11.50 (br s, 1H), 8.35 (br s, 1H), 7.74 (s, 1H), 7.24–7.14 (m, 5H), 6.20 (s, 1H), 4.48 (m, 1H), 3.33 (br s, 1H), 3.20 (dd, J=14, 4 Hz, 1H), 2.93 (dd, J=14, 5 Hz, 1H), 2.19 (s, 1H); $^{13}$C NMR (67.5 MHz, DMSO-$d_6$) δ 164.2, 158.7, 135.6, 134.6, 132.3, 130.0 (2C), 128.0 (2C), 127.5, 126.6, 123.4, 101.7, 55.9, 38.7, 8.9; High-resolution MS m/z 296.1261 (M$^+$) (calcd for $C_{16}H_{16}N_4O_2$: 296.1273). Anal. calcd for $C_{16}H_{16}N_4O_2$ ⅕$H_2O$; C,64.07; H,5.51; N, 18.68. Found: C,64.39, H, 5.65, N,18.29.

EXAMPLE 19

Exemplary Formulation Administered Intravenously, by Drip, Injection, or the Like Vials containing 5 g of powdered glucose are each added aseptically with 10 mg of the invention compound and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor at between approximately 10 ml/day to approximately 1000 ml/day, intravenously, by drip, or via a subcutaneous or intraperitoneal injection, as deemed appropriate by those of ordinary skill in the art.

EXAMPLE 20

Exemplary Formulation to be Administered Orally

A mixture obtained by thoroughly blending 1 g of the compound of the invention, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

EXAMPLE 21

Use of Phenylahistin to Treat a Human Suffering from Cancer

PLH is administered according to the formulation of EXAMPLE 17 to a human patient afflicted with lung cancer. PLH is administered at between approximately 10 mg per day to approximately 1000 mg per day, and in an preferred amount of 50 mg per day, until the growth of the tumor is inhibited.

EXAMPLE 22

Use of (−)-Phenylahistin to Treat Human Suffering from Cancer (−)-PLH is isolated according to the method of EXAMPLE 6, substantially purified, and administered according to the formulation of EXAMPLE 17 to a human patient, afflicted with ovarian cancer, at between approximately 10 mg per day to approximately 100 mg per day, and in a preferred amount of 50 mg per day, until the growth of the tumor is inhibited.

EXAMPLE 23

Anti-Tumor Effect of 2-Isopropyl-(−)-Phenylahistin 2-isopropyl-(−)-phenylahistin, i.e., compound 3 of EXAMPLE 7, is synthesized according to the method of EXAMPLE 7, substantially purified, and administered according to the formulation of EXAMPLE 17 to a human patient afflicted with breast cancer at between approximately 10 mg per day to approximately 100 mg per day, and in a preferred amount of 50 mg per day, until the growth of the tumor is inhibited.

EXAMPLE 24

Synthesis of 2-Dichloroisopropyl-(−)-Phenylahistin 2-dichloroisopropyl-(−)-phenylahistin is synthesized in the following manner: (−)-Phenylahistin, compound 1 of EXAMPLE 7, is placed in the presence of $Cl_2$ and in the presence of water and heat to yield 2 dichloroisopropyl-(−)-phenylahistin.

EXAMPLE 25

Anti-Tumor Effect of 2-Dichloroisopropyl-(−)-Phenylahistin 2-dichloroisopropyl-(−)-phenylahistin, as synthesized in EXAMPLE 22, is substantially purified and administered according to the formulation of EXAMPLE 17 to a human patient afflicted with Lewis Lung Carcinoma at between approximately 10 mg per day to approximately 100 mg per day, and in a preferred amount of 50 mg per day, until the growth of the tumor is inhibited.

EXAMPLE 26

Use of a Combinatorial Chemistry Screening Library

Synthetic studies of PLH are conducted to obtain more potent and less toxic agents. According to the method described by Gordon and Steele, J. Bioorg. Med. Chem. Letters (1995)., 5, 47–50, phenylahistin are its derivatives are screened using an efficient solid phase combinatorial synthesis for a typical diketopiperazine library. By using such technique, phenylahistin is utilized as a prototype for the development of promising new antitumor agents.

EXAMPLE 27

Pharmaceutical Formulations of the Synthesized Phenylahistins
1) Formulations Administered Intravenously by Drip, Injection, Infusion or the Like Vials containing 5 g of powdered glucose are each added aseptically with 10 mg of a compound synthesized by the method and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor at between approximately 10 ml/day to approximately 1000 ml/day, intravenously, by drip, or via a subcutaneous or intraperitoneal injection, as deemed appropriate by those of ordinary skill in the art.
2) Formulation to be Administered Orally or the Like A mixture obtained by thoroughly blending 1 g of a compound synthesized by the method, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

3) Formulation to be Administered Topically

Administration to an individual of an effective amount of the compound can also be accomplished topically by administering the compound(s) directly to the affected area of the skin of the individual. For this purpose, the compound administered or applied is in the form of a composition including a pharmacologically acceptable topical carrier, such as a gel, an ointment, a lotion, or a cream, which includes, without limitation, such carriers as water, glycerol, alcohol, propylene glycol, fatty alcohols, triglycerides, fatty acid esters, or mineral oils. Other topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents may be added as necessary. Percutaneous penetration enhancers such as Azone may also be included. In addition, in certain instances, it is expected that the compound may be disposed within devices placed upon, in, or under the skin. Such devices include patches, implants, and injections which release the compound into the skin, by either passive or active release mechanisms.

EXAMPLE 28

In Vitro Pharmacology of t-butyl Phenylahistin

The in vitro efficacy studies performed with t-butyl phenylahistin included: A) a panel of six tumor cell lines, B) studies in multidrug-resistant tumor cells, and C) studies to determine the mechanism of action.

A). Study of t-butyl Phenylahistin in a Panel of Six Tumor Cell Lines

The following cell lines (source in parentheses) were used: HT29 (human colon tumor; ATCC; HTB-38), PC3 (human prostate tumor; ATCC; CRL-1435), MDA-MB-231 (human breast tumor; ATCC; HTB-26), NCI-H292 (human non-small cell lung tumor; ATCC; CRL-1848), OVCAR-3 (human ovarian tumor; ATCC; HTB-161), B16-F10 (murine melanoma; ATCC; CRL-6475) and CCD-27sk (normal human fibroblast; ATCC; CRL-1475). Cells were maintained at subconfluent densities in their respective culture media.

Cytotoxicity assays were performed as described above in Example 4, using Resazurin fluorescence as an indicator of cell viability.

The disclosed compounds are effective agents against a variety of different and distinct tumor cell lines. Specifically, for example, t-butyl-phenylahistin exhibited its greatest potency against the PC-3 tumor cell line, although the greatest efficacy was displayed against the HT-29 cell line. t-butyl-phenylahistin displayed a marked differential between normal fibroblasts and the tumor cell lines, with a ratio ranging from >20–>100, except for the OVCAR-3 cell line.

TABLE 10

Activity of t-butyl phenylahistin in the Tumor Panel Screen

| | t-butyl-phenylahistin | | |
|---|---|---|---|
| Cell Line | Mean | SD | n |
| HT-29 Colon | | | |
| IC50 nM | 420 | 473 | 3 |
| % Cytotoxicity | 88 | 0.2 | 3 |
| PC-3 Prostate | | | |
| IC50 nM | 174 | — | 2 |
| % Cytotoxicity | 59.5 | — | 2 |
| MDA-MB-231 Breast | | | |
| IC50 nM | 387 | — | 2 |
| % Cytotoxicity | 65.5 | — | 2 |
| NCI-H292 Lung | | | |
| IC50 nM | 384 | 194 | 3 |
| % Cytotoxicity | 65 | 5 | 3 |
| OVCAR-3 Ovary | | | |
| IC50 nM | >20,000 | — | 2 |
| % Cytotoxicity | 37 | — | 2 |
| B16-F10 Melanoma | | | |
| IC50 nM | 736 | 650 | 3 |
| % Cytotoxicity | 74 | 2 | 3 |
| CCD-27sk Fibroblast | | | |
| IC50 nM | >20,000 | — | 2 |
| % Cytotoxicity | 45 | — | 2 |

B). Studies in Drug Resistant Cell Lines

One of the major challenges in the use of chemotherapeutic agents in clinical oncology is the development of resistance to the drug effect by the tumor cells. There are several mechanisms for the development of resistance, each of which will have differential effects on chemotherapeutic drugs. These mechanisms include increased expression of ATP-dependent efflux pumps such as the P-glycoprotein encoded by MDR1 or the multidrug-resistance associated protein 1 encoded by MRP1. Reduced drug uptake, alteration of the drug's target, increasing repair of drug-induced DNA damage, alteration of the apoptotic pathway and the activation of cytochrome P450 enzymes are other examples of mechanisms by which cancer cells become resistant to anticancer drugs. The selected compounds were studied in three different cell lines that exhibit two different mechanisms of resistance; the overexpression of the P-glycoprotein and altered topoisomerase II activity.

1) Human Uterine Sarcoma Tumor Cell Line Pair: MES-SA (Taxol Sensitive) and MES-SA DX (Taxol Resistant).

This cell line expresses elevated mdr-1 mRNA and P-glycoprotein (an extrusion pump mechanism). Pretreatment with cyclosporin-A (CsA) blocks P-glycoprotein and reinstates activity in the resistant cell line for those compounds for which the resistance is due to elevated P-glycoprotein.

As can be seen from Table 11, the potency of t-butyl-phenylahistin was only slightly reduced. Cyclosporin A (CsA) pretreatment did not alter the potency of the selected compounds. In contrast, taxol was virtually inactive in the MES-SA DX resistant cell line, whereas this compound was very potent in the sensitive cell line. CsA treatment restored the sensitivity to taxol of the MES-SA DX cell line. The MES-SA DX cell line also showed reduced susceptibility to etoposide (60 fold), doxorubicin (34 fold) and mitoxantrone (20 fold).

These data indicate that the effects of t-butyl-phenylahistin are not susceptible to the taxol-related resistance mechanism (p-glycoprotein) in this cell line, and that cross-resistance from taxol does not occur to this compound in this model.

TABLE 11

Activity of t-butyl-phenylahistin and Taxol in MES-SA Taxol Sensitive and MES-SA DX Taxol Resistant Human Uterine Sarcoma Tumor Cell Lines

| | MES-SA Sensitive | | | MES-SA DX Resistant | | | |
|---|---|---|---|---|---|---|---|
| | No CsA | CsA Pretreat | | No CsA | | CsA Pretreat | |
| Compound Study | IC50 nM | IC50 nM | Ratio No CsA | IC50 nM | Ratio MES-SA | IC50 nM | Ratio No CsA |
| t-butyl-phenyl-ahistin | | | | | | | |
| Study I | 144 | — | — | 825 | 5.7 | — | — |
| Study III | 122 | 162 | 1.3 | 694 | 4.3 | 622 | 0.9 |
| Taxol | | | | | | | |
| Study I | 4.4 | — | — | >20,000 | >455 | — | — |
| Study II | 13.3 | 7.6 | 0.6 | >>100 | >>8 | 40 | <<0.25 |
| Study III | 7.3 | 2.8 | 0.4 | >24,000 | >3000 | 2.0 | <<0.001 |

2) Human Acute Promyelocytic Leukemia Cell Line Pair: HL-60 (Mitoxantrone-Sensitive) and HL-60/MX-2 (Mitoxantrone-Resistant)

This cell line is considered to have atypical drug resistance properties with altered topoisomerase II catalytic activity without overexpression of P-glycoprotein.

As can be seen in Table 12, these results indicate that the potency of the novel compound in the sensitive and resistant HL-60 cell lines. In contrast, Mitoxantrone loses efficacy by a factor of 24-fold in the resistant HL-60/MX-2 cell line.

Thus, t-butyl-phenylahistin is not susceptible to the same resistance mechanisms as Mitoxantrone in this cell line, and there is no cross-resistance from Mitoxantrone to t-butyl phenylahistin in this model.

TABLE 12

Activity of t-butyl-phenylahistin and Mitoxantrone in the HL-60 Human Acute Promyelocytic Leukemia Tumor Sensitive and Resistant Cell Line Pair

| | HL-60 | HL-60 Resistant | |
|---|---|---|---|
| Compound | Sensitive IC50 nM | IC50 nM | Ratio to Sensitive |
| t-butyl-phenylahistin | 255 | 175 | 0.69 |
| Mitoxantrone | 202 | 4870 | 24.1 |

C) Studies of the Mechanism of Action

1). Action on Microtubule Function

Human umbilical vein endothelial cells (HuVEC from Cambrex) were used in this study, for evaluating the effects of t-butyl-phenylahistin in comparison to colchicine and taxol on tubulin by staining for α-tubulin.

Thirty minutes exposure to t-butyl-phenylahistin or colchicine (all at 2 μM) induced microtubule depolymerization as was indicated by the lack of intact microtubule structure in contrast to that observed in the DMSO Control and cell membrane blebbing (a clear indication of apoptosis) in the HuVEC cells, whereas taxol did not induce microtubule depolymerization under these conditions. Colchicine is a known microtubule depolymerizing agent whereas taxol is a tubulin stabilizing agent.

2). Activation of the Caspase Cascade

Several enzymes in the caspase cascade are activated during apoptosis, including Caspase-3, -8 and -9. The activity of Caspase-3 was monitored in Jurkat cells following treatment with t-butyl-phenylahistin.

The results indicate that caspase-3 was activated in a dose-dependent manner by treatment with t-butyl-phenylahistin in a manner similar to halimide. The caspase-3 activation occurred over a similar concentration range as for the IC50s for cytotoxicity in the Jurkat cell line (Table 13).

TABLE 13

Cytotoxicity of t-butyl-phenylahistin in Jurkat Cells

| NPI Compound | Cytotoxicity | |
|---|---|---|
| | Potency IC50 nM | Efficacy % Cell Death |
| t-butyl-phenylahistin | 165 | 93 |
| Mitoxantrone | 41 | 99 |

3). Cleavage of Poly(ADP-Ribose) Polymerase (PARP) in Jurkat Cells

In order to assess the ability of t-butyl-phenylahistin to induce apoptosis in Jurkat cells, cleavage of poly(ADP-ribose) polymerase (PARP) was monitored. PARP is a 116 kDa nuclear protein that is one of the main intracellular targets of Caspase-3. The cleavage of PARP generates a stable 89 kDa product, and this process can be easily monitored by western blotting. Cleavage of PARP by caspases is one of the hallmarks of apoptosis, and as such serves as an excellent marker for this process. Halimide was active at inducing cleavage of PARP in Jurkat cells 10 hours after exposure of the cells to the compound.

4). Enhanced Vascular Permeability in HuVEC Cells

Compounds that depolymerize microtubules (e.g. combretastatin A-4-phosphate, ZD6126) have been shown to induce vascular collapse in tumors in vivo. This vascular collapse is preceded by a rapid induction of vascular cell permeability initially to electrolytes and soon after to large molecules. The enhanced permeability of HuVEC cells to a fluorescent-labeled dextran is used as a proxy assay for vascular collapse.

t-butyl-phenylahistin rapidly (within 1 hour) induced significant HuVEC monolayer permeability, to an extent similar to colchicine. The microtubule stabilizing agent taxol was inactive in this assay (FIG. 12).

EXAMPLE 29

In Vivo Pharmacology

Studies with t-butyl-phenylahistin were performed. The novel compound was studied as monotherapy and in combination with a clinically-used chemotherapeutic agent. The doses of the selected novel compound were determined from the acute tolerability testing (Maximally Tolerated Dose, MTD) and were adjusted if necessary during each study. The doses of the clinically-used chemotherapeutic agents were selected on the basis of historical studies.

t-butyl-phenylahistin was were compared in the HT-29 human colon tumor, the DU-145 human prostate and the MCF-7 human breast tumor xenograft models.

The above models all use the subcutaneous xenograft implantation technique and are potentially subject to selective effects of a compound on the subcutaneous vasculature producing a magnified (or apparent) antitumor activity. In order to circumvent this possibility, two other tumor models have been incorporated in the research. One of these is the observation of lung metastases following the intravenous injection of B16-F10 mouse melanoma tumor cells. The other model is the implantation of MDA-231 human breast tumor cells in the mouse mammary fat pad. While this latter model is a xenograft model, the subcutaneous vasculature does not play a role.

Methods

1). Xenograft Models

Animals used were (exceptions are indicated for individual studies): female nude mice (nu/nu) between 5 and 6 weeks of age (~20 g, Harlan); group size was 9–10 mice per group unless otherwise indicated.

Cell lines used for tumor implantation were: HT-29 human colon tumor; MCF-7 human breast tumor; A549 human non small cell lung tumor; MiaPaCa-2 human pancreas tumor; DU-145 human prostate tumor.

The selected novel compound was administered as monotherapy via the intraperitoneal (i.p.) route at the doses indicated for the individual study; for the combination studies the selected reference chemotherapy agents were injected 15–30 min prior to the compound.

Vehicles used in these studies were: 12.5% DMSO, 5% Cremaphor and 82.5% peanut oil for the selected novel compounds; (1:3) Polysorbate 80:13% ethanol for taxotere; (1:1) Cremaphor:ethanol for paclitaxel; for CPT-11 each mL of solution contained 20 mg of irinotecan hydrochloride, 45 mg of sorbitol NF powder, and 0.9 mg of lactic acid, the pH being adjusted to 7.4 with NaOH or HCl. Saline dilutions are used to achieve the injection concentrations used for the reference compounds.

HT-29 Human Colon Tumor Model

Animals were implanted subcutaneously (s.c.) by trocar with fragments of HT-29 tumors harvested from s.c. growing tumors in nude mice hosts. When the tumor size reached 5 mm×5 mm (about 10–17 days) the animals were matched into treatment and control groups. Mice were weighed twice weekly and tumor measurements were obtained using calipers twice weekly, starting on Day 1. The tumor measurements were converted to estimated mg tumor weight using the formula $(W^2 \times L)/2$. When the estimated tumor weight of the control group reached an average of 1000 mg the mice were weighed, sacrificed and the tumor removed. The tumors were weighed and the mean tumor weight per group was calculated and the tumor growth inhibition (TGI) was determined for each group (100% minus the change in the mean treated tumor weight/the change in the mean control tumor weight×100.

In this model unless otherwise noted for the individual study, the selected novel compound was injected intraperitoneally every third day for 15 days [1, 4, 8, 11 and 15 (q3d×5)]; CPT-11 was administered intraperitoneally on days 1, 8 and 15 (qw×3).

MCF-7 Human Breast Tumor Model

Female nude mice (~20 g) were implanted s.c. with 21-day release estrogen (0.25 mg) pellets 24 hours prior to the s.c. implantation with MCF-7 tumor fragments (harvested from s.c. tumors in nude mice hosts). The study then proceeded as described for the HT-29 model, using taxotere as the standard chemotherapy agent.

In this model unless otherwise noted for the individual study, the novel compound was injected via the intraperitoneal route daily on Days 1–5, inclusive (qd×5); taxotere was administered intravenously on Days 1, 3 and 5 (qod×3).

A549 Human Lung Tumor Model

Animals were implanted s.c. by trocar with fragments of A549 tumors harvested from s.c. growing tumors in nude mice hosts. When the tumor size reached 5 mm×5 mm (about 10–17 days) the animals were matched into treatment and control groups. The rest of the study proceeded as described for the HT-29 model, using taxotere and CPT-11 as the standard chemotherapy agents.

In this model unless otherwise noted for the individual study, the tested compound was administered via the intraperitoneal route on a q3d×5 dose schedule for the CPT-11 combination or on a qd×5 dose regimen for the combination with taxotere; CPT-11 was administered via the intraperitoneal route on a qw×3 schedule; taxotere was administered intravenously on a qod×3 dose regimen.

MiaPaCa-2 Human Pancreas Tumor Model

Animals were implanted s.c. by trocar with fragments of MiaPaCa-2 tumors harvested from s.c. growing tumors in nude mice hosts. When the tumor size reached 5 mm×5 mm (about 10–17 days) the animals were matched into treatment and control groups. The rest of the study proceeded as described for the HT-29 model, using gemcitabine as the standard chemotherapy agent.

In this model unless otherwise noted for the individual study, test compound was administered every third day via the intraperitoneal route on Days 1, 4, 7, 10 and 15 (q3d×5); gemcitabine was administered via the intraperitoneal route on Days 1, 4, 7 and 10 (q3d×4).

DU-145 Human Prostate Tumor Model

Male mice were implanted s.c. by trocar with fragments of DU-145 tumors harvested from s.c. growing tumors in nude male mice hosts. When the tumors reached ~5 mm×5 mm (at about 13–17 days) the animals were matched into treatment and control groups. The remainder of the study proceeded as for the HT-29 model, using taxotere as the standard chemotherapy agent.

In this model unless otherwise noted for the individual study, test compound was administered via the intraperitoneal route on Days 1, 3, 5, 8 and 11 (q3d×5); taxotere was administered intravenously on Days 1, 3 and 5 (q2d×3).

2). Non Subcutaneous Implantation Tumor Models

The animals used were: female nude mice (nu/nu) (MDA-231 study) or B6D2F1 (B16-F10 studies) mice between 5 and 6 weeks of age (~20 g, Harlan); group size was 10 mice per group unless otherwise indicated.

The cell lines used were: MDA-MB-231 human breast tumor and B16-F10 murine melanoma cells.

Compound was administered as monotherapy via the intraperitoneal route at the doses indicated for the individual study; for the combination studies the selected reference chemotherapy agents were injected 15–30 min prior to the NPI compound.

MDA-231 Human Breast Tumor

Female nude mice were injected in the mammary fat pad with $2\times10^6$ MDA-231 cells harvested from in vitro cell culture. When the tumor size reached 5 mm×5 mm (about 14–28 days) the animals were matched into treatment and control groups. The study then proceeded as described for the HT-29 model, using paclitaxel as the standard chemotherapy agent.

In this model unless otherwise noted for the individual study, the test compound was administered via the intraperitoneal route on Days 1, 4, 8, 11 and 15 (q3d×5); paclitaxel was administered via the intraperitoneal route on Days 1–5 (qd×5).

B16-F10 Metastatic Murine Melanoma Model

Mice received B16-F10 cells (prepared from an in vitro cell culture of B16-F10 cells) by the iv route on Day 0. On Day 1 mice were randomized into treatment and control groups and treatment commenced. Mice were weighed twice weekly, starting on Day 1. All mice are sacrificed on Day 16, the lungs removed, weighed and the surface colonies counted. Results are expressed as mean colonies of treated mice/mean colonies of control mice (T/C)×100%). The metastasis growth inhibition (MGI) is this number subtracted from 100%. Paclitaxel was the standard chemotherapy agent used in this study.

In this model unless otherwise noted for the individual study, the test compounds were administered via the intraperitoneal route on Days 1–5 (qd×5); paclitaxel was administered intravenously on Days 1–5(qd×5).

When appropriate (n 3), results are presented as means ± SEM. Statistical analysis of studies with several groups was performed using ANOVA with Neuman-Keuls post test, unless otherwise indicated. A one-tailed t-test was also used based on the hypothesis that the compound or drug, or the combination, would reduce tumor growth.

Results

Studies in the HT-29 Human Colon Tumor Xenograft Model

1. Study of Activity of t-butyl-Phenyalhistin in the HT-29 Human Colon Tumor Xenograft Study The results of this study are presented in FIG. 17 and Table 14. The combination therapy group indicated a marked synergy between the novel compound and CPT-11. The individual tumor weights demonstrate the effectiveness of the cotherapy treatment (FIG. 18). The TGI for the combination group surpasses the NCI criterion for a positive effect, whereas the TGI for CPT-11 monotherapy did not reach this level.

TABLE 14

Summary of Studies Performed in the HT-29 Human Colon Tumor Model

| Study Description | | NPI-Compound | | Chemotherapeutic Agent | | Combination | Exceed NCI | |
|---|---|---|---|---|---|---|---|---|
| Number Status | Endpoint | Number, mg/kg ip | Result TGI % | Name, Dose | Result TGI % | Results TGI % | Criterion (TGI 58%) | Comments |
| 2139 | TGI | t-butyl-phenylahistin 30 q3dx5 | No Effect | CPT-11 100 ip qwx3 | 32.7 | 77.7 *, # | | Combination Synergy |

*p < 0.05 vs Control;
**p < 0.01 vs Control;
p < 0.05 vs CPT-11 Alone;
p < 0.01 vs CPT-11 Alone;
+ = Number of Deaths 2. Summary of the Effects of t-butyl-Phenylahistin in Combination with CPT-11 in the HT-29 Human Colon Tumor Xenograft Model When combined with CPT-11, t-butyl-phenylahistin enhanced the effect of CPT-11, the standard chemotherapeutic agent, to a level well in excess of the NCI criterion of a TGI 58% for a positive effect. The results generated in the study are very comparable for both the in-life observations and for the weights of the tumors excised at autopsy.

Studies in the DU-145 Human Prostate Tumor Xenograft Model

Figure 9A:
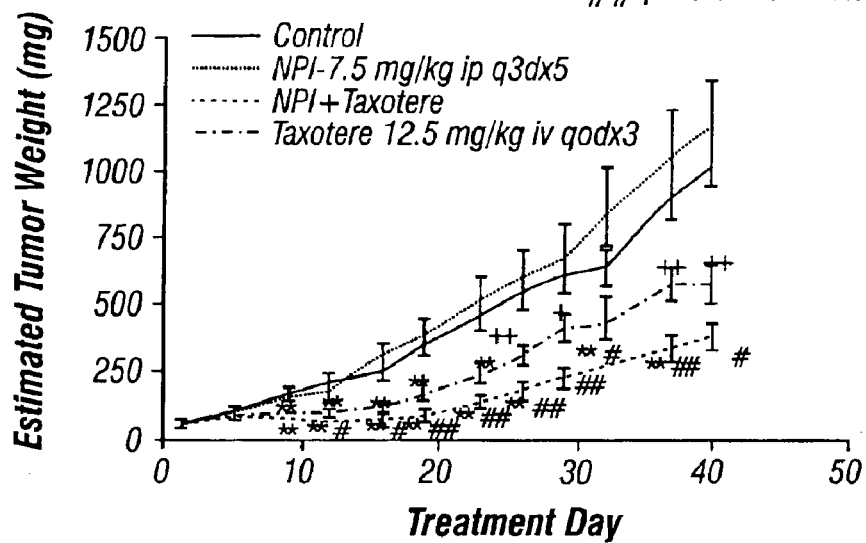
FIG. 9 depicts the effects of t-butyl-phenylahistin alone and in combination with Taxotere on the estimated tumor growth based on observations made during the in-life portion of the DU-145 Human Prostate Tumor Xenograft Model.
Figure 9B:
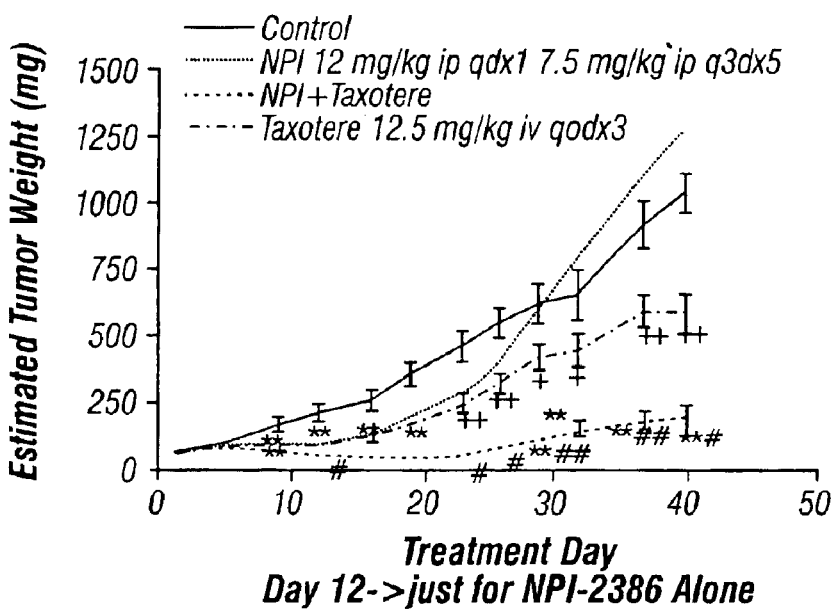
Figure 9C:
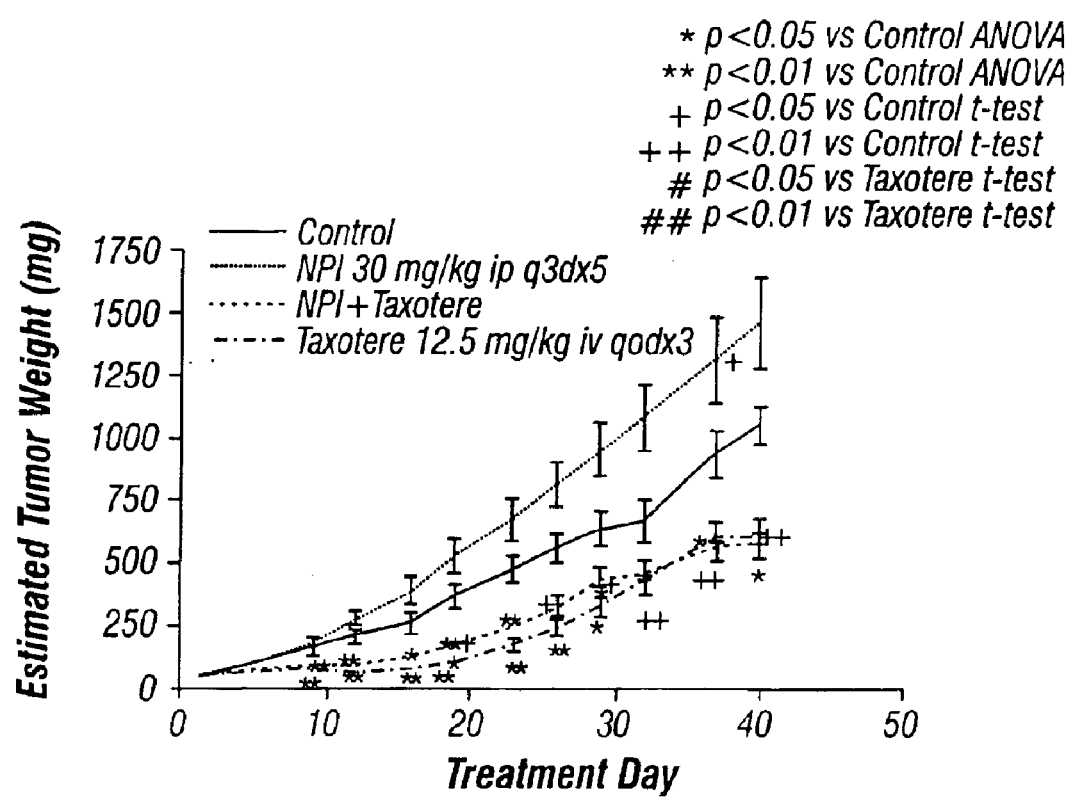

The study involved an assessment of t-butyl-phenylahistin alone and in combination with taxotere.
1. Activity of t-butyl-phenylahistin Alone or in Combination with Taxotere in the DU-145 Human Prostate Xenograft Model A study comparing t-butyl-phenylahistin alone and in combination with taxotere was initiated. The results are shown in FIG. 9.

The excised tumor weights at autopsy confirmed the observations made during the in-life segment of the study. The tumor growth inhibition indices indicated a marked inhibition of tumor growth. Taxotere alone did not reach the NCI established criterion for a positive effect (TGA 58%).
2. Studies in the MCF-7 Human Breast Tumor Xenograft Model This study considered the effects of t-butyl-phenylahistin in the MCF-7 human breast tumor xenograft model. The doses of the compound were administered on Days 1, 2, 3, 4, and 7; Taxotere was administered on Days 1, 3 and 7.

Figure 10A:
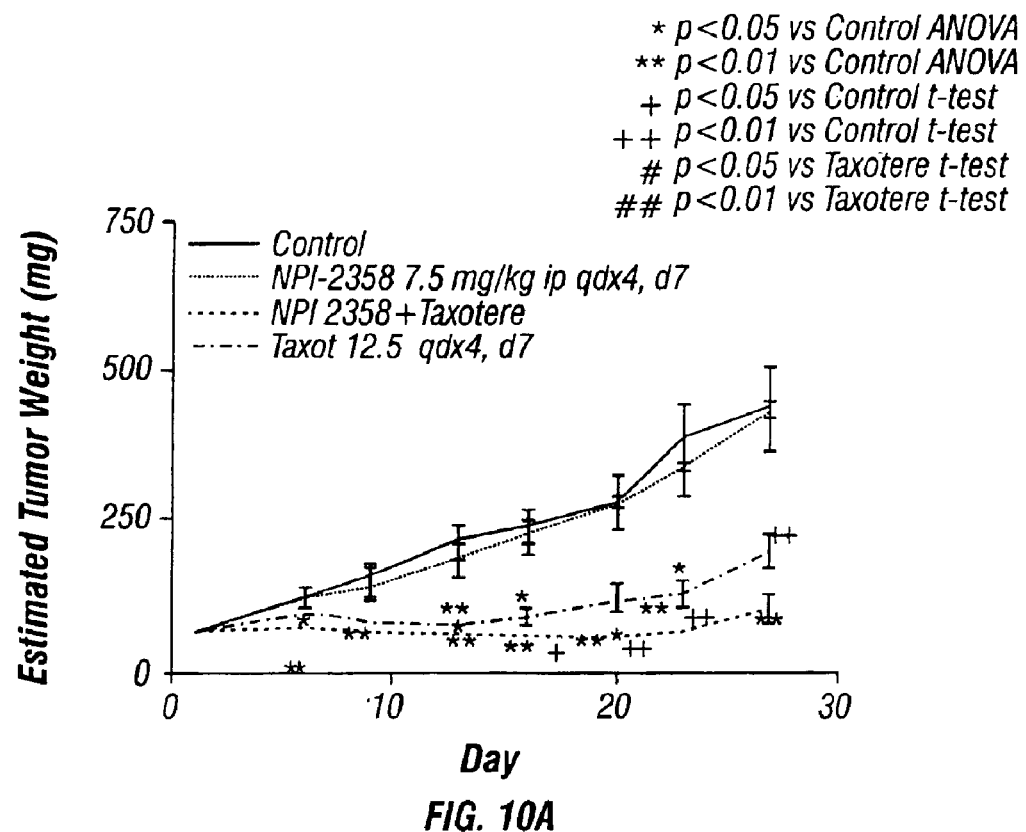
FIG. 10 depicts the effects of t-butyl-phenylahistin alone and in combination with Taxotere in MCF-7 Human Breast Tumor Xenograft model.
Figure 10B:
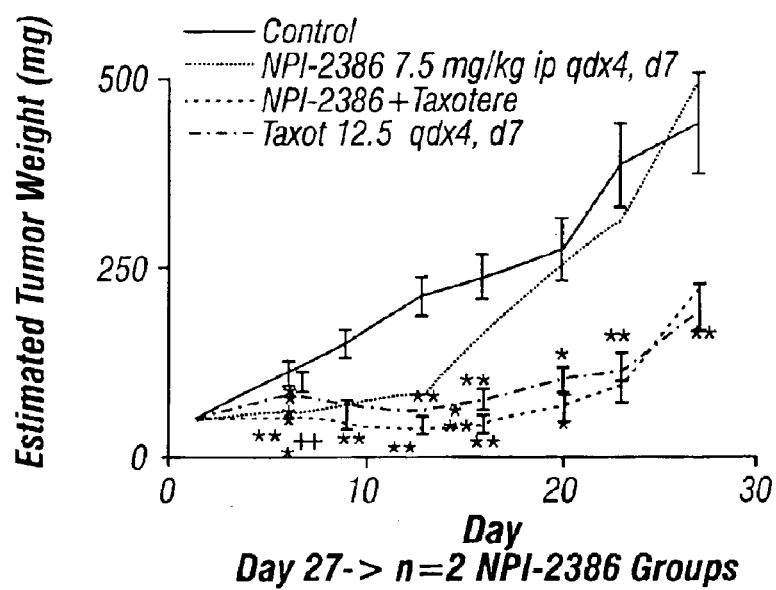
Figure 10C:
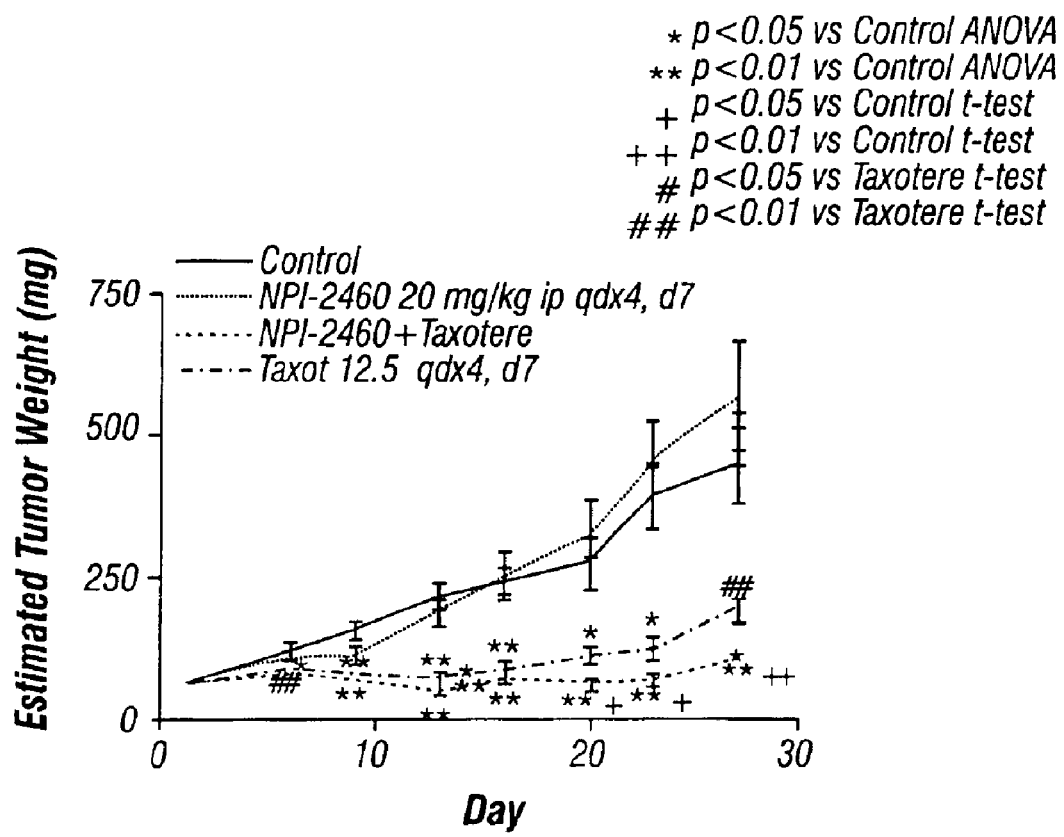
Figure 11A:
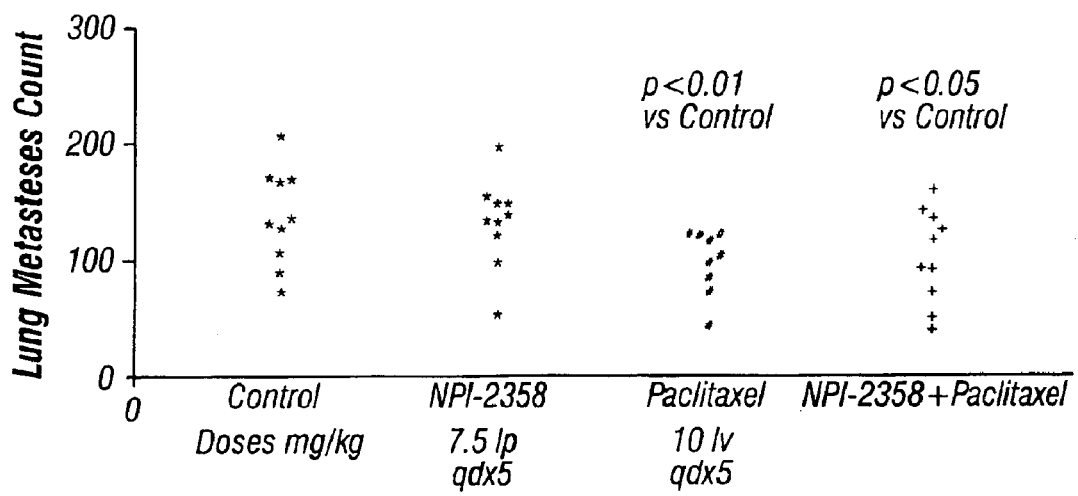
FIG. 11 depicts effects of t-butyl-phenylahistin alone and in combination with Paclitaxel in the Murine Melanoma B16F10 Metastatic Tumor Model.
Figure 11B:
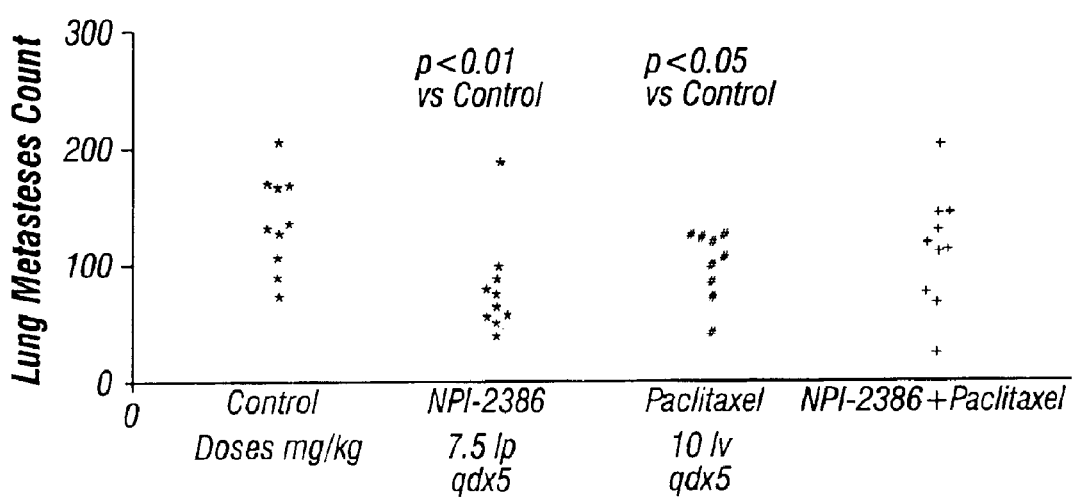
Figure 11C:
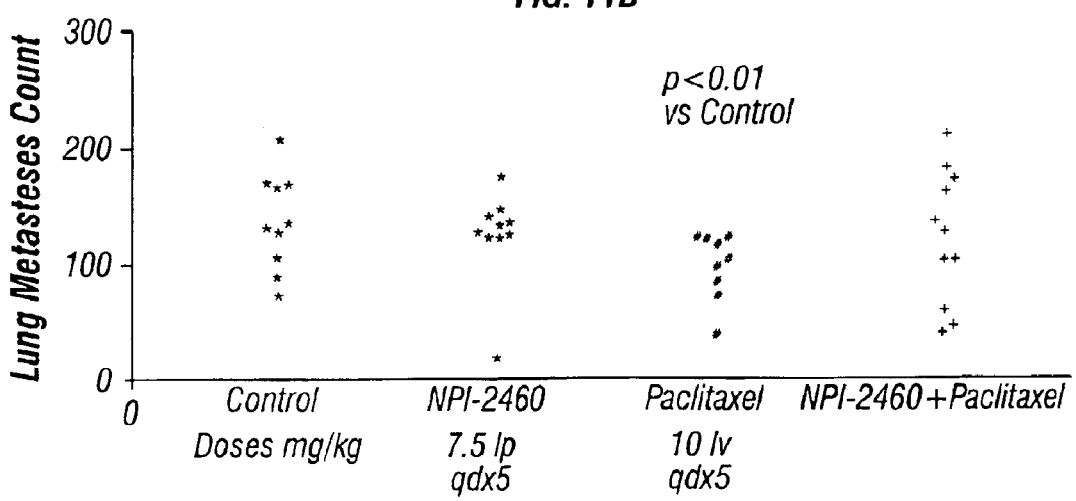

The selected novel compound has early onset, statistically significant effects when used in combination with taxotere in this model, apparently almost completely blocking estimated tumor growth (FIG. 10). t-butyl-phenylahistin exhibited a significant potentiation of taxotere.
3. Studies in the Murine Melanoma B16 F10 Metastatic Tumor Model This study examined the effect of t-butyl-phenylahistin alone and in combination with paclitaxel on the number of metastases appearing on the surface of the lung 16 days after the intravenous injection of B16 F10 melanoma cells to the mouse. This model is not a xenograft model; however, it does not involve a high degree of vascularization into the tumor mass.

This study does not itself establish that combination therapy is more effective than monotherapy, it does indicate that t-butyl-phenylahistin is most effective in highly vascularized tumors (FIG. 12).

EXAMPLE 30

Assays for Activity Against Pathogenic Fungi

Comparative activity of a phenylahistin or its analog against a pathogenic fungus, relative to known antifungal compounds recited above, for use in determining the phenylahistin or its analog's AF/IS value is measured directly against the fungal organism, e.g. by microtiter plate adaptation of the NCCLS broth macrodilution method described in *Diagn Micro and Infect Diseases* 21:129–133 (1995). Antifungal activity can also be determined in whole-animal models of fungal infection. For instance, one may employ the steroid-treated mouse model of pulmonary mucormycosis (Goldaill, L. Z. & Sugar, A. M. 1994 *J Antimicrob Chemother* 33:369–372). By way of illustration, in such studies, a number of animals are given no phenylahistin or its analog, various doses of phenylahistin or its analog (and/or combinations with one or more other antifungal agents), or a positive control (e.g. Amphotericin B), respectively, beginning before, at the time of, or subsequent to infection with the fungus. Animals may be treated once every 24 hours with the selected dose of phenylahistin or its analog, positive control, or vehicle only. Treatment is continued for a predetermined number of days, e.g. up to ten days. Animals are observed for some time after the treatment period, e.g. for a total of three weeks, with mortality being assessed daily. Models can involve systemic, pulmonary, vaginal and other models of infection with or without other treatments (e.g. treatment with steroids) designed to mimic a human subject susceptible to infection.

To further illustrate, one method for determining the in vivo therapeutic efficacies ($ED_{50}$, e.g. expressed in mg phenylahistin or its analog/kg subject), is a rodent model system. For example, a mouse is infected with the fungal pathogen such as by intravenous infection with approximately 10 times the 50% lethal dose of the pathogen ($10^6$ *C. albicans* cells /mouse). Immediately after the fungal infection, phenylahistin compounds are given to the mouse at a predetermined dosed volume. The $ED_{50}$ is calculated by the method of Van der Waerden (*Arch Exp Pathol Pharmakol* 195:389–412, 1940) from the survival rate recorded on 20th day post-infection. Generally, untreated control animals die 7 to 13 days post-infection.

In another illustrative embodiment, *C. albicans* Wisconsin (C43) and *C. tropicalis* (C112), grown on Sabouraud dextrose agar (SDA) slants for 48 h at 28° C., are suspended in saline and adjusted to 46% transmission at 550 nm on a spectrophotometer. The inoculum is further adjusted by hemacytometer and confirmed by plate counts to be approximately 1 or $5 \times 10^7$ CFU/ml. CF-1 mice are infected by injection 1 or $5 \times 10^6$ CFU into the tail vein. Antifungal agents are administered intravenously or subcutaneously in ethanol:water (10:90), 4 h post infection and once daily thereafter for 3 or 4 more days. Survival is monitored daily. The $ED_{50}$ can be defined as that dose which allows for 50% survival of mice.

EXAMPLE 31

Evaluating Antimicotic Activity

Benzimidazoles and griseofulvin are anti-tubulin agents capable of binding to fungal microtubules. Once bound, these compounds interfere with cell division and intracellular transport in sensitive organisms, resulting in cell death. Commercially, benzimidazoles are used as fungicidal agents in veterinary medicine and plant disease control. A wide variety of fungal species, including *Botrytis cinerea, Beauveria bassiana, Helminthosporium solani, Saccharomyces cerevisiae* and *Aspergillus* are susceptible to these molecules. Toxicity concerns and increasing drug resistance, however, have negatively impacted their usage. Griseofulvin is used clinically to treat ringworm infections of the skin, hair and nails, caused by *Trichophyton* sp., *Microsporum* sp., and *Epidermophyton floccosum*. Its antifungal spectrum, however, is restricted to this class of fungal organisms. Genotoxicity is also a significant side effect. Terbinafine, while an alternative first-line treatment, is more costly. Further, clinical resistance recently has been observed in *Trichophyton rubrum* (the major causative agent for all dermatophyte infections).

In *Candida albicans*, microtubule/microfilament formation is affected where cells are exposed to the microtubule inhibitors nocodazole and chloropropham. These results further validate the exploration of cytoskeleton inhibitors as effective antimycotic agents. Accordingly, several of the compounds disclosed herein were evaluated for antimycotic activity.

Specifically, disclosed compounds were evaluated alongside commercially available microtubulin inhibitors as well as recognized antifungal agents. The test compounds and controls used in this study: (−)-Phenylahistin and t-butyl phenylahistin, Colchicine (commercial microtubulin inhibitor tested versus 3 *Candida* isolates), Benomyl (commercial microtubulin inhibitor tested versus 3 *Candida* isolates), Griseofulvin (commercial microtubulin inhibitor and antibiotic control for testing versus 6 dermatophyte isolates), Amphotericin B (antibiotic control for testing versus 3 *Candida* isolates), Itraconazole (antibiotic control for testing versus 2 *Aspergillus* isolates).

Microorganisms against which these compounds were tested included: *Candida albicans, Candida glabrata, Aspergillus fumigatus, Trichophyton rubrum, Trichophyton mentagrophytes, Epidermophyton floccosum*. With the exception of *Candida glabrata* (one isolate), two isolates of each species were tested.

Antifungal susceptibility testing was accomplished according to the methods outlined in the National Committee for Clinical Laboratory Standards, M38-A "Reference Method for Broth Dilution Antifungal Susceptibility Testing of Conidium-Forming Filamentous Fungi; Approved Standard." This includes testing in RPMI-1640 with glutamine and without bicarbonate, an inoculum size of $0.4$–$5 \times 10^4$, and incubation at 30 or 35° C. for 48 hours. The minimum inhibitory concentration (MIC) was defined as the lowest concentration that resulted in an 80% reduction in turbidity as compared to a drug-free control tube. Drug concentrations were 0.03–16 µg/ml for the investigational compounds, 0.015–8 µg/ml for itraconazole and griseofulvin.

The minimum inhibitory concentration (MIC) at which a compound prevented the growth of the target microorganism was assessed according to the modified version of the NCCLS protocol. Minimum inhibitory concentrations (MIC) were determined at the first 24-hour interval where growth could be observed in the drug-free control tube. The defined MIC was the lowest concentration that exhibited an 80% reduction in turbidity as compared to the growth control. The minimum lethal concentration (MLC) was determined by plating 0.1 µl from the MIC concentration and each concentration above the MIC. The MLC was called at the first concentration that exhibited five or fewer colonies of fungal growth representing a 99.95% kill. When a MIC was obtained, a minimum fungicidal concentration (MFC) was determined to assess the fungistatic/fungicidal nature of the compound. This procedure entails diluting drug-treated cell samples (removed from test wells containing compound at and above the MIC) to compound concentrations significantly below the inhibitory concentration and depositing them on agar plates. The compound is scored as fungistatic if the cells are able to resume growth and fungicidal if no regrowth is possible because the compound had killed the organisms.

Compounds disclosed herein were shown to be effective against two *Trichophyton* species. *T. rubrum* is the principal causative agent for human dermatophytic infections, and would be the key organism to target in the development of a clinical agent.

Compound t-butylphenylahistin at least was equivalent in potency compared to griseofulvin, a current, standard pharmaceutical agent used for treating dermatophytic infections.

Compound (−)-Phenylahistin also was potent when tested versus *T. rubrum* and even more potent versus the sensitive *T. mentagrophytes* isolate.

In those instances when an MFC could be determined, the results indicate that these compounds are fungistatic in nature (see Tables 19 and 20).

TABLE 17

Antifungal Activity of Phenylahistins

MICs and MFCs, µg/ml

| Compound | C. albicans 90028 MIC | C. albicans 90028 MFC | C. albicans 10231 MIC | C. albicans 10231 MFC | C. glabrata MIC | C. glabrata MFC | A. fumigatus isolate #1 MIC | A. fumigatus isolate #1 MFC | A. fumigatus isolate #2 MIC | A. fumigatus isolate #2 MFC |
|---|---|---|---|---|---|---|---|---|---|---|
| (−)-Phenylahistin | >70 | ND** | >70* | ND | >70 | ND | >16 | ND | >16 | ND |
| t-butyl phenylahistin | >32 | ND | >32 | ND | >32 | ND | >16 | ND | <0.03 | 0.125 |
| amphotericin B | 0.5 | 0.5 | 0.5 | 0.5 | 1 | 1 | ND | ND | ND | ND |
| griseofulvin | ND | ND | ND | ND | ND | ND | ND | ND | 0.5 | ND |
| itraconazole | ND | ND | ND | ND | ND | ND | 1 | ND | ND | ND |
| colchicine | >128 | ND | >128 | ND | >128 | ND | ND | ND | ND | ND |
| benomyl | 64 | >512 | 64 | >512 | 64 | >512 | ND | ND | ND | ND |

TABLE 18

Antifungal Activity of Phenylahistins

MICs and MFCs, µg/ml

| Compound | T. rubrum isolate #1 MIC | T. rubrum isolate #1 MFC | T. rubrum isolate #2 MIC | T. rubrum isolate #2 MFC | T. mentagrophytes isolate #1 MIC | T. mentagrophytes isolate #1 MFC | T. mentagrophytes isolate #2 MIC | T. mentagrophytes isolate #2 MFC | E. floccosum isolate #1 MIC | E. floccosum isolate #1 MFC | E. floccosum isolate #2 MIC | E. floccosum isolate #2 MFC |
|---|---|---|---|---|---|---|---|---|---|---|---|---|
| NPI2350 | >16 | ND | 0.16 | >16 | 16 | >16 | >16 | ND | >16 | ND | >16 | ND |
| NPI2460 | <0.03 | 0.125 | <0.03 | <0.03 | 4 | >16 | >16 | ND | >16 | ND | >16 | ND |
| amphotericin B | ND | ND | ND | ND | ND | ND | ND | ND | ND | ND | ND | ND |
| griseofulvin | 0.5 | ND | <0.015 | ND | 1 | ND | 2 | ND | 2 | ND | 4 | ND |
| itraconazole | ND | ND | ND | ND | ND | ND | ND | ND | ND | ND | ND | ND |
| colchicine | ND | ND | ND | ND | ND | ND | ND | ND | ND | ND | ND | ND |
| benomyl | ND | ND | ND | ND | ND | ND | ND | ND | ND | ND | ND | ND |

The examples described above are set forth solely to assist in the understanding of the invention. Thus, those skilled in the art will appreciate that the disclosed methods and compounds encompass and may otherwise provide further derivatives of phenylahistins.

One skilled in the art would readily appreciate that the present invention is well adapted to obtain, for example, the ends and advantages mentioned, as well as others inherent. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

As noted above, all patents and publications mentioned in the specification are indicative of the levels of those skilled in the art to which the invention pertains. All patents and publications are hereby incorporated by reference herein to the extent allowable by law, such that each individual patent and publication may be treated as specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

What is claimed is:

1. A method of treating at least one fungal infection in a mammal afflicted with at least one fungal infection which comprises administering an antifungally effective amount of a compound sufficient for such treating or preventing, and wherein the compound has the following structure:

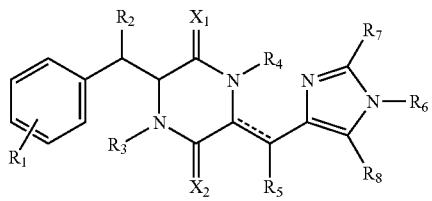

wherein:
$R_1$, $R_2$, $R_5$, $R_7$, and $R_8$ are each separately selected from the group consisting of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups, $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups, $X_1$ and $X_2$ are separately selected from the group consisting of an oxygen atom, and a sulfur atom, and the dashed bond represents a bond selected from the group consisting of a carbon-carbon single bond and a carbon-carbon double bond.

2. The method of claim 1, wherein the fungal infection is selected from the group consisting of an Aspergillosis infection, blastomycosis infection, Candidiasis infection, Coccidioidomycosis infection, Cryptococcosis infection, Histopolasmosis infection, Paracoccidioidomycosis, Sporotrichosisand, and Mucormycosis infection.

3. The method of claim 2, wherein the Aspergillosis infection is invasive pulmonary aspergillosis.

4. The method of claim 2, wherein the Mucormycosis infection is craniofacial mucormycosis or pulmonary mucormycosis.

5. The method of claim 2, wherein the Candidiasis infection is retrograde candidiasis of the urinary tract.

6. A pharmaceutical composition for treating fungal infection comprising an antifungally effective amount of a pharmaceutically acceptable carrier and a compound having the structure:

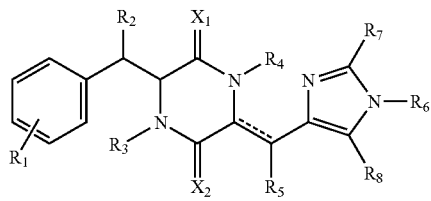

wherein:
$R_1$, $R_2$, $R_5$, $R_7$, and $R_8$ are each separately selected from the group consisting of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, substituted nitro, phenyl, and substituted phenyl groups, $R_3$, $R_4$, and $R_6$ are each separately selected from the group consisting of a hydrogen atom, a halogen atom, and saturated $C_1$–$C_{12}$ alkyl, unsaturated $C_1$–$C_{12}$ alkenyl, cycloalkyl, alkoxy, cycloalkoxy, aryl, substituted aryl, heteroaryl, substituted heteroaryl, amino, substituted amino, nitro, and substituted nitro groups, $X_1$ and $X_2$ are separately selected from the group consisting of an oxygen atom, and a sulfur atom, and the dashed bond represents a bond selected from the group consisting of a carbon-carbon single bond and a carbon-carbon double bond.

7. The composition of claim 6, wherein the fungal infection is selected from the group consisting of an Aspergillosis infection, blastomycosis infection, Candidiasis infection, Coccidioidomycosis infection, Cryptococcosis infection, Histopolasmosis infection, Paracoccidioidomycosis, Sporotrichosisand, and Mucormycosis infection.

8. The composition of claim 7, wherein the Aspergillosis infection is invasive pulmonary aspergillosis.

9. The composition of claim 7, wherein the Mucormycosis infection is craniofacial mucormycosis or pulmonary mucormycosis.

10. The composition of claim 7, wherein the Candidiasis infection is retrograde candidiasis of the urinary tract.

* * * * *

UNITED STATES PATENT AND TRADEMARK OFFICE
CERTIFICATE OF CORRECTION

PATENT NO. : 7,026,322 B2  
APPLICATION NO. : 10/632688  
DATED : April 11, 2006  
INVENTOR(S) : Hayashi et al.

Page 1 of 1

It is certified that error appears in the above-identified patent and that said Letters Patent is hereby corrected as shown below:

Title page,  
Inventors Item (75), Delete "Kawasaki" and insert -- Shiga --  
Item (56) References Cited, Other Publications, column 2, line 12, after "Produced" insert -- by --  
Above Item (74) Primary Examiner, column 2, line 1, delete "Balasurbramanian" and insert -- Balasubramanian --

Title Page, Item (56) References Cited, Page 2, Other Publications  
Column 1, line 8, delete "Structure" and insert --Structures --  
Column 1, line 19, delete "MIT" and insert "MTT"  
Column 2, line 17, delete "Cyclic" and insert -- Cycling --

Column 1, line 8, after "2001" insert -- , --  
Column 5, line 58 (Approx.), delete "B16F10" and insert -- B16 F10 --  
Column 12, line 63, delete "deveopment" and insert -- development --  
Column 14, line 30, delete "transplantaion" and insert -- transplantation --  
Column 15, line 19, delete "intollerant" and insert -- intolerant --  
Column 23, line 13, delete "C;" and insert -- C.; --  
Column 27, line 56, delete "et al," and insert -- et al., --  
Column 27, line 67, delete "6.6+1.7" and insert -- 6.6$\pm$1.7 --  
Column 29, line 15, delete "et al," and insert -- et al., --  
Column 29, line 24, delete "et al," and insert -- et al., --  
Column 29, line 55, delete "J" and insert -- J. --  
Column 39, line 29, delete "$C_{20}H_{24}N_4O\ _2$" and insert -- $C_{20}H_{24}N_4O_2$ --  
Column 43, line 45, delete "Intravenously" and insert -- Intravenously, --

Signed and Sealed this

Twenty-sixth Day of September, 2006

JON W. DUDAS  
*Director of the United States Patent and Trademark Office*